United States Patent
Ong et al.

(10) Patent No.: US 9,725,451 B2
(45) Date of Patent: Aug. 8, 2017

(54) MEROPENEM DERIVATIVES AND USES THEREOF

(71) Applicant: Kala Pharmaceuticals, Inc., Waltham, MA (US)

(72) Inventors: Winston Zapanta Ong, Stoneham, MA (US); Pawel Wojciech Nowak, Woodcliff Lake, NJ (US); Jinsoo Kim, Brighton, MA (US); Elizabeth M Enlow, Waltham, MA (US); James Bourassa, Somerville, MA (US); Yen Cu, Cambridge, MA (US); Alexey Popov, Waltham, MA (US); Hongming Chen, Belmont, MA (US)

(73) Assignee: Kala Pharmaceuticals, Inc., Waltham, MA (US)

( * ) Notice: Subject to any disclaimer, the term of this patent is extended or adjusted under 35 U.S.C. 154(b) by 10 days.

(21) Appl. No.: 14/777,018

(22) PCT Filed: Mar. 14, 2014

(86) PCT No.: PCT/US2014/028627
§ 371 (c)(1),
(2) Date: Sep. 15, 2015

(87) PCT Pub. No.: WO2014/144285
PCT Pub. Date: Sep. 18, 2014

(65) Prior Publication Data
US 2016/0039823 A1     Feb. 11, 2016

Related U.S. Application Data

(60) Provisional application No. 61/789,335, filed on Mar. 15, 2013.

(51) Int. Cl.
| | |
|---|---|
| *A61K 31/407* | (2006.01) |
| *C07D 477/20* | (2006.01) |
| *C07D 487/04* | (2006.01) |
| *A61K 45/06* | (2006.01) |
| *A61K 9/50* | (2006.01) |
| *A61K 9/51* | (2006.01) |

(52) U.S. Cl.
CPC .......... *C07D 477/20* (2013.01); *A61K 9/5015* (2013.01); *A61K 9/5031* (2013.01); *A61K 9/5123* (2013.01); *A61K 9/5146* (2013.01); *A61K 31/407* (2013.01); *A61K 45/06* (2013.01); *C07D 487/04* (2013.01)

(58) Field of Classification Search
CPC .............................. C07D 477/20; A61K 31/407
See application file for complete search history.

(56) References Cited

U.S. PATENT DOCUMENTS

| | | | |
|---|---|---|---|
| 6,410,525 | B1 | 6/2002 | Matsui |
| 6,491,903 | B1 | 12/2002 | Forster et al. |
| 2004/0176350 | A1 | 9/2004 | Matsui |
| 2005/0065141 | A1 | 3/2005 | Odink |
| 2011/0172200 | A1 | 7/2011 | Prezelj et al. |
| 2013/0316006 | A1 | 11/2013 | Popov et al. |

FOREIGN PATENT DOCUMENTS

| | | |
|---|---|---|
| WO | 9315078 A1 | 8/1993 |
| WO | 2012063085 | 5/2012 |

OTHER PUBLICATIONS

Bhat et al, J. Pharm. Sci. Jun. 1996, 85, pp. 624-630.
Khanvilkar et al, Adv. Drug Delivery Rev. Jun. 11, 2001, 48(2-3), pp. 173-193.
Shunkichi Tanaka et al: "Novel prodrugs of meropenem with two lipophilic promoieties: synthesis and pharmacokinetics", The Journal of Antibiotics, vol. 64, No. 3, Mar. 1, 2011, pp. 233-242.
Wei X et al: "Biodegradable poly(-caprolactone)-poly(ethylene glycol) copolymers as drug delivery system", International Journal of Pharmaceutics, vol. 381, No. 1, Oct. 20, 2009, pp. 1-18.
Extended European Search Report and Search Opinion of EP14762750, corresponding to PCT/US2014/028627, dated Jul. 21, 2016.
International Preliminary Report on Patentability and Written Opinion of the International Searching Authority corresponding to PCS/US2014/028627 dated Jul. 31, 2014.
Teitelbaum et al., Synthesis, pH-dependent, and plasma stability of meropenem prodrugs for potential use against drug-resistant tuberculosis, 21 Bioorganic & Medicinal Chemistry 5605-5617 (2013).
International Search report mailed on Jul. 31, 2014, in corresponding PCT Application No. PCT/US2014/028627.

*Primary Examiner* — Rebecca Anderson
*Assistant Examiner* — Karen Cheng
(74) *Attorney, Agent, or Firm* — K&L Gates LLP; Louis C. Cullman; Michelle Glasky Bergman

(57) ABSTRACT

The present invention provides novel derivative of β-lactam antibiotics, such as meropenem. The inventive compounds include compounds of Formula (I), and pharmaceutically acceptable salts, solvates, hydrates, polymorphs, co-crystals, tautomers, stereoisomers, isotopically labeled derivatives, and prodrugs thereof. Also provided are particles (e.g., nanoparticles) and pharmaceutical compositions thereof that are mucus penetrating. The inventive particles and pharmaceutical compositions may be useful in delivering an inventive compound to the respiratory tract of a subject. The invention further provides methods of using and kits including the inventive compounds, particles thereof, and/or pharmaceutical compositions thereof for treating and/or preventing a pulmonary disease (e.g., a respiratory tract infection).

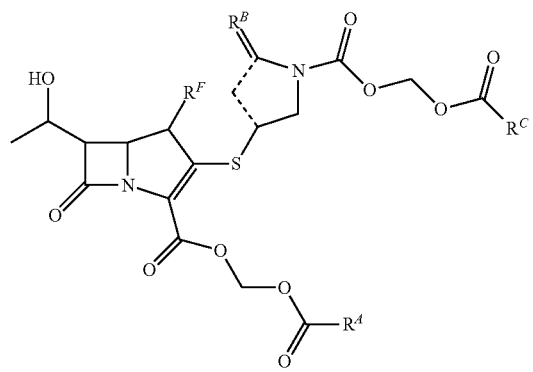

(I)

67 Claims, 7 Drawing Sheets

MEROPENEM DERIVATIVES AND USES THEREOF

RELATED APPLICATIONS

The present application claims priority under 35 U.S.C. §119(e) to U.S. Provisional Patent Application No. 61/789,335, filed Mar. 15, 2013, and entitled "Meropenem Derivatives and Uses Thereof", which is incorporated herein by reference.

GOVERNMENT FUNDING

This invention was made with government support under Grant No. 1R43HL106899-01 awarded by the National Heart, Lung, and Blood Institute of the National Institutes of Health. The government has certain rights in the invention.

BACKGROUND OF THE INVENTION

Bacterial infection in the lung and its complications are major causes of morbidity and mortality, especially in patients suffering from cystic fibrosis. Current mode of treatments for these infections requires delivery of antibiotics to the lung tissue. These delivery techniques are either invasive and require hospitalization or trained medical personnel (e.g., intravenous or intramuscular injections), suffer from poor bioavailability (e.g., oral doses), and may have other drawbacks such as adverse effects associated with systemic drug exposure. Local administration of therapeutics via inhalation is a preferred mode of delivery, since it is non-invasive, convenient, does not require hospitalization, and reduces systemic exposure and its potential related adverse side-effects. However, delivery of therapeutic agents such as antibiotics via inhalation is generally ineffective due to low delivery efficiency and high clearance. A more effective method for drug delivery of anti biotics to the lung via inhalation is needed.

Meropenem, a β-lactam antibiotic, is currently one of the most potent antibiotics available for intravenous therapy against a range of pathogenic bacteria, such as *Pseudomonas aeruginosa* ($MIC_{90}$ is about 8 µg/mL), the most frequent pathogen acquired by subjects with cystic fibrosis with lung airway infections. A conventional pharmaceutical composition of meropenem is not suitable for oral administration because of poor absorption. Although meropenem can be developed as an inhalable product, its high water solubility (>1 mg/mL) restricts the possible means of administration, such that a nebulized solution is the only option. The dose of therapeutic agent when administered in a nebulized solution is limited by its solubility, such that there is a specific maximum drug load per dose. Dosed as a solution (e.g., by nebulizer) the drug likely will clear quite rapidly from the lungs into systemic circulation, leaving limited local exposure in the lungs, and thus frequent dosing would be required. Furthermore, nebulization is a difficult and time-consuming procedure that, when used chronically (e.g., administered daily for over 30 days), significantly decreases patient life quality.

Meropenem may benefit from new methods and pharmaceutical compositions for inhalational administration, such as development into a dry-powder inhalable (DPI) drug product, which is a preferred mode of therapeutic delivery over nebulization. Delivery by DPI achieves greater drug load per dose than that of a nebulized solution. In addition, this delivery method circumvents the inconveniences to patients that are associated with nebulization. To achieve this, a particle-based formulation of meropenem must be developed by producing an improved water-insoluble form and formulation of meropenem. To effectively deliver the drug particles to the lung tissues, the particles must also overcome the mucus barrier. The mucus layer present at various points of entry into the body, including the eyes, nose, lungs, gastrointestinal tract, and female reproductive tract, serves to protect the body against pathogens, allergens, and debris by effectively trapping and quickly removing them via mucus turnover. For effective delivery of therapeutic particles via mucus membranes, the particles must be able to readily penetrate the mucus layer to avoid mucus adhesion and rapid mucus clearance. However, it is often difficult for particles administered via inhalation to be delivered to a tissue of the respiratory tract (e.g., lung, trachea, or bronchus) in effective amounts due to rapid clearance and/or other reasons. Thus, new pharmaceutical compositions and formulations to deliver therapeutic agents, such as meropenem, to the lung with a high drug concentration per dose and effective penetration through the mucus barrier are needed.

SUMMARY OF THE INVENTION

Drug delivery to the respiratory tract is especially difficult. Conventional drug delivery methods of water-soluble drugs (e.g., oral or injectional administration) have many drawbacks. For example, the delivery of the antibiotic meropenem to the respiratory tract for the treatment of a bacterial infection (e.g., nosocomial pneumonia, severe community-acquired pneumonia, and cystic fibrosis) is difficult, and meropenem has only been administered intravenously. A conventional pharmaceutical composition of meropenem is not suitable for oral administration because an oral dose of meropenem results in poor absorption. Inhalational administration may be able to effectively deliver the therapeutic agent to the target tissue; however, meropenem is a water-soluble drug that could only be locally administered to the respiratory epithelium via nebulization, and it will likely be cleared rapidly from the lungs, thereby requiring frequent and larger dosing. A more preferred mode of local delivery to the respiratory tract or lungs is via a dry-powder inhalable (DPI) drug product, which would be comprised of a carrier particle-based formulation containing smaller particles of an insoluble form of meropenem associated with a pharmaceutically acceptable carrier particle.

Mucus found in various tissues (e.g., respiratory tract, gastrointestinal tract, eye, genito-urinary tract) of a subject is a viscoelastic and adhesive substance that traps most foreign objects (e.g., microorganisms, particles, dust). For effective drug delivery, particles that are immobilized in the mucus are quickly eliminated by mucus clearance mechanisms; therefore, they are not able to deliver their payload effectively. For a particle to effectively deliver the payload, it must quickly penetrate the mucus and/or avoid mucus clearance mechanisms. Accordingly, modifying mucoadhesive materials with a coating to reduce the mucoadhesiveness of the particle, and decreasing the size of the particle to below that of the mucus gel pore may allow for efficient delivery of the particles.

The present invention successfully addresses the problems associated with formulating and delivering meropenem and other β-lactam antibiotics to the respiratory system of a subject for the treatment of various respiratory tract infections. In one aspect, the present invention first provides novel water-insoluble derivatives of β-lactam antibiotics, such as derivatives of meropenem (1).

Meropenem (1)

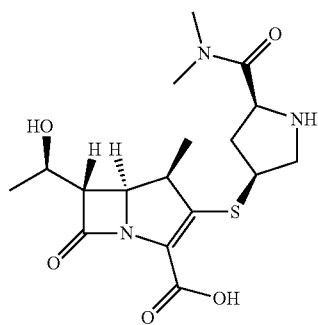

In certain embodiments, the invention provides compounds of Formula (I):

(I)

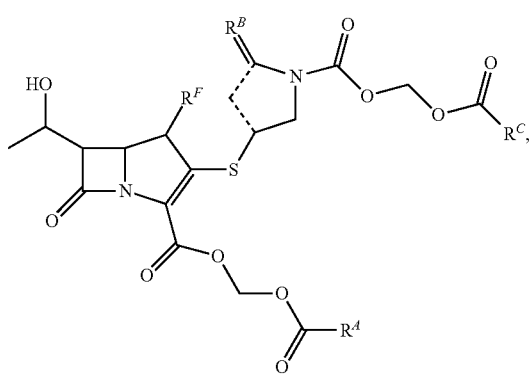

and pharmaceutically acceptable salts, solvates, hydrates, polymorphs, co-crystals, tautomers, stereoisomers, and isotopically labeled derivatives thereof, wherein $R^A$, $R^B$, $R^C$, and $R^F$ are as described herein. Compared to the parent β-lactam antibiotics, the inventive derivatives may show lower hydrophilicity and/or aqueous solubility. The derivatives, when administered in a conventional pharmaceutical composition to a subject, may show improved bioavailability (e.g., oral bioavailability) than the parent β-lactam antibiotics. Moreover, the derivative may be more easily processed into mucus-penetrating particles (MPPs) and/or mucus-penetrating crystals (MPCs) suitable for inhalational administration to the respiratory tract of the subject. These advantages of the derivatives over the parent β-lactam antibiotics may be attributed to the lower hydrophilicity and/or aqueous solubility of the derivative. In certain embodiments, the inventive compounds are crystalline. The derivatives are typically converted in vivo to provide the parent β-lactam antibiotic. A particular example of a compound of the invention is a compound of Formula (I-A-1):

(I-A-1)

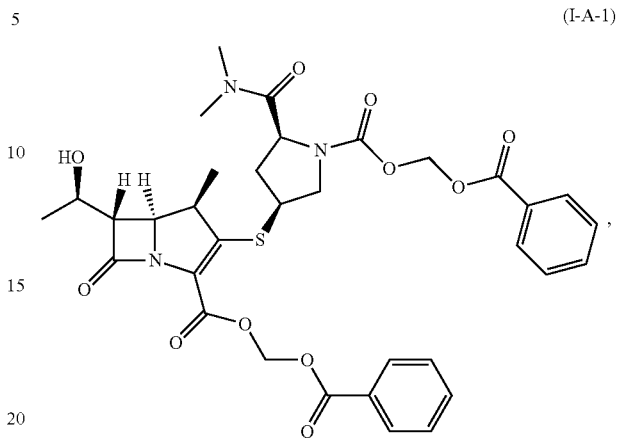

and solvates, hydrates, polymorphs, co-crystals, tautomers, stereoisomers, and isotopically labeled derivatives thereof. In vivo the compound of Formula (I-A-1) hydrolyzes to yield the parent antibiotic meropenem. In one aspect, the compound of Formula (I-A-1) is crystalline. In another aspect, the present invention provides methods of preparing the inventive compounds. The inventive compounds may be synthesized by acylating the polar moieties (e.g., amino and carboxyl groups) of a β-lactam antibiotic to yield a product that is more hydrophobic than the parent β-lactam antibiotic. In certain embodiments, the methods of preparing the inventive compounds include reacting a compound of Formula (i-A), or a salt, tautomer, stereoisomer, or isotopically labeled derivative thereof, with a compound of Formula (i-B) to provide a compound of Formula (i-C), or a salt, tautomer, stereoisomer, or isotopically labeled derivative thereof:

(i-A)

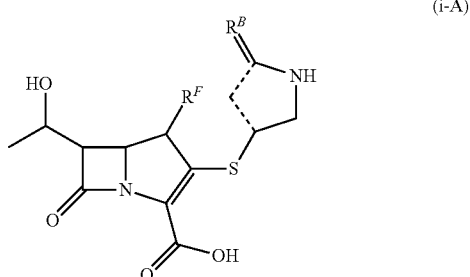

(i-B)

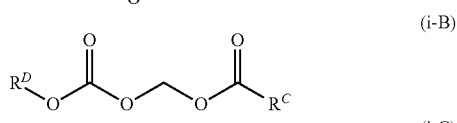

(i-C)

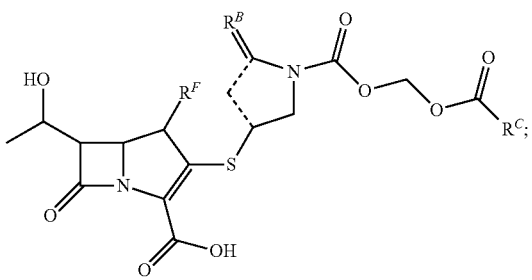

reacting the compound of Formula (i-C), or the salt, tautomer, stereoisomer, or isotopically labeled derivative thereof, in the presence of a base with a compound of Formula (i-D) to provide the compound of Formula (I), or a pharmaceutical acceptable salt, tautomer, stereoisomer, or isotopically labeled derivative thereof:

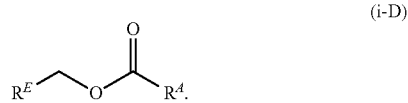

(i-D)

In another aspect, the present invention provides particles comprising a compound of Formula (I). In one aspect, the present invention provides particles comprising a compound of Formula (I) that is crystalline. In certain embodiments, the particles are mucus penetrating. The particles of the invention may include a coating surrounding a core. The core may contain primarily a compound of the invention, or the core may be a polymeric core with the compound encapsulated in the polymer. In certain embodiments, the inventive particles of a compound of invention are nanoparticles (e.g., particles having an average diameter of at least about 10 nm and less than about 1 μm). The inventive particles may be useful in delivering the pharmaceutical agent to a subject. In certain embodiments, the particles of the invention are capable of delivering the pharmaceutical agent to the respiratory tract of a subject. In some embodiments, the inventive particles comprising a compound of the invention are associated with larger carrier particles in a DPI drug product. Therefore, the inventive particles (whether administered directly or in association with larger carrier particles in a DPI drug product that delivers the inventive particles to the lung), by penetrating the mucus of the respiratory tract and delivering the pharmaceutical agent (e.g., a compound of the invention) thereto, may be useful in treating a respiratory tract disease.

Another aspect of the invention relates to pharmaceutical compositions comprising an inventive compound and/or a plurality of inventive particles. In certain embodiments, the pharmaceutical compositions are useful in delivering a pharmaceutical agent (e.g., a compound of the invention) to a subject. The inventive pharmaceutical compositions may also be useful in treating and/or preventing a respiratory tract disease of a subject, such as a respiratory tract infection (e.g., influenza, bronchitis, or pneumonia).

Another aspect of the invention relates to pharmaceutical compositions for delivery by a dry powder inhaler, wherein the pharmaceutical composition comprises an inhalable dry powder comprising a plurality of inventive particles that are mucus penetrating, and pharmaceutically acceptable carrier particles.

In another aspect, the present invention provides kits comprising an inventive compound, a plurality of inventive particles, and/or an inventive pharmaceutical composition. The kits of the invention may further include instructions or prescribing information for administering the compound, particles, or pharmaceutical composition to a subject.

Another aspect of the invention relates to methods of treating and/or preventing a respiratory tract disease in a subject in need thereof. In certain embodiments, the respiratory disease being treated and/or prevented is an upper respiratory tract disease (e.g., influenza). In certain embodiments, the respiratory disease being treated and/or prevented is a lower respiratory tract disease (e.g., a pulmonary disease). In certain embodiments, the pulmonary disease being treated and/or prevented is a pulmonary disease (e.g., cystic fibrosis or a pulmonary infection, such as pneumonia). In some embodiments, the subject is a human. In some embodiments, the subject is a human with cystic fibrosis and a pulmonary infection.

Another aspect of the invention relates to methods of increasing the delivery of a compound of the invention to a tissue (e.g., the respiratory tract) of a subject.

In yet another aspect, the present invention provides methods of increasing the coverage uniformity of the inventive particles over the surface of a target tissue of the respiratory tract. The present invention also provides methods of increasing the coverage uniformity of a pharmaceutical agent over the surface of a target tissue of the respiratory tract, wherein the pharmaceutical agent is included in inventive particles.

Another aspect of the invention relates to methods of increasing the concentration of a compound of the invention in a tissue (e.g., the respiratory tract) of a subject. Another aspect of the invention relates to methods of increasing the duration time of a compound of the invention in the respiratory tract of a subject.

In certain embodiments, the inventive methods include administering to a subject a compound, particle, and/or pharmaceutical composition of the invention. In certain embodiments, the compound, particle, or pharmaceutical composition is administered inhalationally. In certain embodiments, the compound or particles comprising compound is formulated to be mucus-penetrating. In another embodiment, the pharmaceutical composition comprises compound or particles comprising compound that are mucus-penetrating.

The details of particular embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

Compounds of the invention can comprise one or more asymmetric centers, and thus can exist in various isomeric forms, e.g., enantiomers and/or diastereomers. For example, the compounds of the invention can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw Hill, NY, 1962); and Wilen, Tables of Resolving Agents and Optical Resolutions p. 268 (E. L. Eliel, Ed., Univ. of Notre Dame Press, Notre Dame, Ind. 1972). The invention additionally encompasses compounds of the invention as individual isomers substantially free of other isomers, and alternatively, as mixtures of various isomers.

When a range of values is listed, it is intended to encompass each value and sub range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties.

The term "heteroaliphatic", as used herein, refers to aliphatic moieties that contain one or more heteroatoms (e.g., oxygen, sulfur, nitrogen, phosphorus, and silicon) in place of carbon atoms. For example, a $C_{1-12}$ heteroaliphatic moiety includes 1-12 carbon atoms and at least one heteroatom. A heteroaliphatic moiety may also be saturated or unsaturated and may include any number of unsaturated bonds (e.g., double and triple bonds) as valency permits.

Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., CH$_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a nonaromatic cyclic hydrocarbon group having from 3 to 10 ring carbon atoms ("$C_{3-10}$ carbocyclyl") and zero heteroatoms in the nonaromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or Spiro ring system such as a bicyclic system ("bicyclic carbocyclyl") and can be saturated or can be partially unsaturated, "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. Iii certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl 2,5-dione. Exemplary 5 membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix—ene, e.g., alkylene, alkenylene, alkynylene, carbocyclylene, heterocyclylene, arylene, and heteroarylene.

As used herein, the term "optionally substituted" refers to substituted or unsubstituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_1$-C$_{10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

The term "counterion" refers to an anionic or cationic counterion. An "anionic counterion" is a negatively charged atom or group associated with a cationic atom or group in order to maintain electronic neutrality. Exemplary anionic counterions include halide anions (e.g., F$^-$, Cl$^-$, Br$^-$, and I$^-$), NO$_3$$^-$, ClO$_4$$^-$, OH$^-$, H$_2$PO$_4$$^-$, HSO$_4$$^-$, sulfonate anions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate anions (e.g., acetate, ethanoate, propanoate, benzoate, glycerate, lactate, tartrate, glycolate, and the like). A "cationic counterion" is a positively charged atom or group associated with an anionic atom or group in order to maintain electronic neutrality. Exemplary cationic counterions include inorganic cations (e.g., metal cations (e.g., alkali metal cations, alkali earth metal cations, and transition metal cations)) and organic cations (e.g., ammonium cations, sulfonium cations, phosphonium cations, and pyridinium cations). A counterion may be monovalent, divalent, trivalent, tetravalent, pentavalent, or hexavalent.

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamatec, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O) SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N (R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O) (OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$ $R^{aa}$, —$C(=NR^{bb})OR^{aa}$, —$C(=NR^{bb})N(R^{bb})_2$, —$S(=O)$ $R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "electron withdrawing group" refers to an atom (including ionic and isotopic forms of the atom) or a group of a compound that reduces the electron density from a nearby atom and/or group of the compound. The nearby atom and/or chemical group may be directly attached to the electron withdrawing group or may be attached to the electron withdrawing group through one or more atoms and/or groups. An electron withdrawing group may reduce the electron density of a nearby atom and/or group through conjugation, hyperconjugation and/or induction. An electron withdrawing group may comprise one or more electronegative atoms, unsaturated bonds, and/or formal positive charge. Examples of electron withdrawing groups are well known in the art, such as those listed in *Advanced Organic Chemistry*, J. March, 4$^{th}$ Ed.; John Wiley & Sons, New York; 1992. For example, electron withdrawing groups include, but are not limited to, halogen, partially or fully halogenated aliphatic, partially or fully halogenated carbocyclyl, —$N(R^{hh})_3^+$, —$CN$, —$NO_2$, —$C(=NR^{hh})R^{hh}$, —$C(=NR^{hh})OR^{hh}$, —$C(=NR^{hh})N(R^{hh})_2$, —$C(=O)R^{hh}$, —$C(=O)OR^{hh}$, —$C(=O)N(R^{hh})_2$, —$S(=O)R^{hh}$, —$S(=O)OR^{hh}$, —$S(=O)N(R^{hh})_2$, —$S(=O)_2R^{hh}$, —$S(=O)_2OR^{hh}$, —$S(=O)_2N(R^{hh})_2$, —$OS(=O)R^{hh}$, —$OS(=O)OR^{hh}$, —$OS(=O)N(R^{hh})_2$, —$OS(=O)_2R^{hh}$, —$OS(=O)_2OR^{hh}$, and —$OS(=O)_2N(R^{hh})_2$, wherein each instance of $R^{hh}$ is independently $R^{aa}$ as described herein, substituted or unsubstituted aliphatic, substituted or unsubstituted heteroaliphatic, substituted or unsubstituted carbocyclyl, substituted or unsubstituted heterocyclyl, substituted or unsubstituted aryl, or substituted or unsubstituted heteroaryl. Examples of electron withdrawing groups also include aryl substituted with one or more substituents and heteroaryl substituted with one or more substituents, wherein at least one of the one or more substituents is halogen, partially or fully halogenated aliphatic, partially or fully halogenated carbocyclyl, —$N(R^{hh})_3^+$, —$CN$, —$NO_2$, —$C(=NR^{hh})R^{hh}$, —$C(=NR^{hh})OR^{hh}$, —$C(=NR^{hh})N$ $(R^{hh})_2$, —$C(=O)R^{hh}$, —$C(=O)OR^{hh}$, —$C(=O)N(R^{hh})_2$, —$S(=O)R^{hh}$, —$S(=O)OR^{hh}$, —$S(=O)N(R^{hh})_2$, —$S(=O)_2R^{hh}$, —$S(=O)_2OR^{hh}$, —$S(=O)_2N(R^{hh})_2$, —$OS(=O)R^{hh}$, —$OS(=O)OR^{hh}$, —$OS(=O)N(R^{hh})_2$, —$OS(=O)_2R^{hh}$, —$OS(=O)_2OR^{hh}$, or —$OS(=O)_2N(R^{hh})_2$, wherein each instance of $R^{hh}$ is as described herein.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxyamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

As used herein, the term "pharmaceutically acceptable" means that which is, within the scope of sound medical judgment, suitable for use in contact with the tissues of humans and lower animals without undue toxicity, irritation, allergic response, and the like, and are commensurate with a reasonable benefit/risk ratio.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of a compound include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of a compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R \cdot xH_2O$, wherein R is a compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

The term "tautomers" refer to compounds that are interchangeable forms of a particular compound structure, and that vary in the displacement of hydrogen atoms and electrons. Thus, two structures may be in equilibrium through the movement of $\pi$ electrons and an atom (usually H). For example, enols and ketones are tautomers because they are rapidly interconverted by treatment with either acid or base. Another example of tautomerism are the aci- and nitro-forms of phenylnitromethane, that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental pharmaceutical composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of a compound have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on a compound are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals, aggregates, composites, pulverized, milled or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having a characteristic dimension of less than about 1 micrometer and at least about 1 nanometer, where the characteristic dimension of the particle is the smallest cross-sectional dimension of the particle. A crystalline nanoparticle is referred to as a "nanocrystal."

The term "microparticle" refers to a particle having a characteristic dimension of less than about 1 millimeter and at least about 1 micrometer, where the characteristic dimension of the particle is the smallest cross-sectional dimension of the particle.

As used herein, the term "carrier particles" means particles of any pharmaceutically acceptable inert material or combination thereof used in inhalable dry powders or dry powder inhaler drug product. Carrier particles include those made of excipients well known in the art, including those composed of one or more materials selected from sugar alcohols; polyols, such as sorbitol, mannitol and xylitol, and crystalline sugars, including monosaccharides and disaccharides, such as lactose (e.g., anhydrous lactose or α-lactose monohydrate); organic salts such as sodium lactate and other organic compounds such as urea; inorganic salts such as sodium chloride and calcium carbonate; polysaccharides, for example starch and its derivatives; and oligosaccharides, for example cyclodextrins and dextrins. In one aspect, preferred carrier particles are those made of lactose, and more preferably those made of α-lactose monohydrate. For a DPI drug product, carrier particles are associated with particles of a pharmaceutical agent, such as inventive particles comprising a compound of Formula (I) that are mucus penetrating. In certain aspects, a DPI drug product consists of inventive particles are nanoparticles having reduced mucoadhesion and pharmaceutically acceptable carrier particles.

The term "nanostructure" refers to a structure having at least one region or characteristic dimension with a dimension of less than about 1000 nm, e.g., less than about 400 nm, less than about 300 nm, less than about 200 nm, less than about 100 nm, or less than about 50 nm. Typically, the region or characteristic dimension will be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), and the like. Nanostructures can be substantially homogeneous in material properties, or in certain embodiments can be heterogeneous (e.g. heterostructures). Nanostructures can be, e.g., substantially crystalline, substantially monocrystalline, polycrystalline, amorphous, or a combination thereof. In one aspect, each of the three dimensions of the nanostructure has a dimension of less than about 1000 nm, e.g., or even less than about 400 nm, less than about 300 nm, less than about 200 nm, less than about 100 nm, or less than about 50 nm. Nanostructures can comprise one or more surface ligands (e.g., surfactants).

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein. The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal. When not used with respect to a nanostructure, the term "monocrystalline" to materials that are composed of substantially a single crystallite of substantially the same size and orientation.

"Nanocrystal" is a nanostructure that is substantially monocrystalline. A nanocrystal thus has at least one region or characteristic dimension with a dimension of less than about 1000 nm, e.g., less than about 400 nm, less than about 300 nm, less than about 200 nm, less than about 100 nm, or less than about 50 nm. Typically, the region or characteristic dimension will be along the smallest axis of the structure. Examples of such structures include nanowires, nanorods, nanotubes, branched nanowires, nanotetrapods, nanotripods, nanobipods, nanocrystals, nanodots, quantum dots, nanoparticles, nanoribbons, and the like. Nanostructures can be substantially homogeneous in material properties, or in certain embodiments can be heterogeneous (e.g. heterostructures). Optionally, a nanocrystal can comprise one or more surface ligands (e.g., surfactants). The nanocrystal is optionally substantially single crystal in structure (a "single crystal nanostructure" or a "monocrystalline nanostructure"). While nanostructures for use in the present invention can be fabricated from essentially any convenient material or material, preferably the nanostructure is prepared from an inorganic material, e.g., an inorganic conductive or semiconductive material. A conductive or semi-conductive nanostructure often displays 1-dimensional quantum confinement, e.g., an electron can often travel along only one dimension of the structure. Nanocrystals can be substantially homogeneous in material properties, or in certain embodiments can be heterogeneous (e.g., heterostructures). The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. The nanocrystals can be fabricated from essentially any convenient material or materials.

The term "polycrystalline" refers to materials that are composed of many crystallites of varying size and orientation. When used with respect to nanostructures, the term "polycrystalline" refers to a crystalline nanostructure that is not monocrystalline.

A "biocompatible" material refers to a material that does not typically induce an adverse response when inserted or injected into a subject. The adverse response includes significant inflammation and/or acute rejection of the material by the immune system of the subject, for instance, via a T-cell-mediated response. It is recognized that "biocompatibility" is a relative term and that some degree of immune response is to be expected even for materials that are highly compatible with living tissues of the subject. However, as used herein, "biocompatibility" refers to the acute rejection of a material by at least a portion of the immune system, i.e., a material that lacks biocompatibility (i.e. being non-biocompatible) in a subject provokes an immune response in the subject that is severe enough such that the rejection of the material by the immune system cannot be adequately controlled and often is of a degree such that the material must be removed from the subject in order for the subject to be as well as it was before the non-biocompatible material was introduced into the subject. One test to determine biocompatibility of a material is to expose the material to cells (e.g., fibroblasts or epithelial cells) in vitro; the material is considered biocompatible if it does not result in significant cell death at moderate concentrations, e.g., at concentrations of about 50 micrograms/$10^6$ cells. In certain embodiments, there is no significant cell death if less than about 20% of the cells are dead, even if phagocytosed or otherwise uptaken by the cells. In some embodiments, a material is biocompatible if contacting it with cells in vitro results in less than 20% cell death and if the administration of the material in vivo does not induce unwanted inflammation or other adverse responses. In certain embodiments, a biocompatible material is biodegradable. A non-limiting example of biocompatible materials is biocompatible polymers (including biocompatible copolymers).

A "biodegradable" material refers to a material that is able to degrade chemically and/or biologically (e.g., by hydrolysis or enzymatic activity), within a physiological environment, such as within the body or when introduced to cells. For instance, the material may be one that hydrolyzes spontaneously upon exposure to water (e.g., within a subject) and/or may degrade upon exposure to heat (e.g., at temperatures of about 37° C.). Degradation of a material may occur at varying rates, depending on the material used. For example, the half-life of the material (the time at which 50% of the material is degraded into smaller components) may be on the order of days, weeks, months, or years. The material may be biologically degraded, e.g., by enzymatic activity or cellular machinery, for example, through exposure to a lysozyme. In some embodiments, the material may be broken down into smaller components that cells can either reuse or dispose of without significant toxic effect on the cells (e.g., fewer than about 20% of the cells are killed when the components are added to cells in vitro). Non-limiting examples of biodegradable materials are biodegradable polymers (including biodegradable copolymers). Examples of biodegradable polymers include, but are not limited to, poly(ethylene glycol)-poly(propylene oxide)-poly(ethylene glycol) triblock copolymers, poly(vinyl alcohol) (PVA), poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters), and copolymers thereof (e.g., poly(lactide-co-glycolide) (PLGA)).

As used herein, the terms "pharmaceutical composition" and "formulation" are used interchangeably.

As used herein, the terms "pharmaceutical agent" and "drug" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys)); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish.

As defined herein, the term "target tissue" refers to any biological tissue of a subject (including a group of cells, a body part, or an organ) or a part thereof, including blood and/or lymph vessels, which is the object to which a compound, particle, and/or pharmaceutical composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented.

The terms "administer," "administering," or "administration," as used herein, refers to implanting, absorbing, ingesting, injecting, inhaling, or otherwise introducing a compound, particle, and/or pharmaceutical composition of the invention into or onto a subject.

As used herein, the terms "treatment," "treat," and "treating" refer to reversing, alleviating, delaying the onset of, or inhibiting the progress of a "pathological condition" (e.g., a disease, disorder, or condition, or a sign or symptom thereof) described herein, such as a bacterial infection. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of exposure to a pathogen). Treatment may also be continued after symptoms have resolved, for example, to delay or prevent recurrence.

As used herein, the terms "condition," "disease," and "disorder" are used interchangeably.

An "effective amount" of a pharmaceutical agent (e.g., a compound of the invention) described herein refers to an amount sufficient to elicit the desired biological response, i.e., treating the condition. As will be appreciated by those of ordinary skill in this art, the effective amount of a pharmaceutical agent described herein may vary depending on such factors as the desired biological endpoint, the pharmacokinetics of the pharmaceutical agent, the condition being treated, the mode of administration, and the age and health of the subject. An effective amount encompasses therapeutic and prophylactic treatment. For example, in treating a bacterial infection, an effective amount of a pharmaceutical agent may inhibit the growth of the bacteria and/or kill the bacteria.

A "therapeutically effective amount" of a pharmaceutical agent (e.g., a compound of the invention) described herein is an amount sufficient to provide a therapeutic benefit in the treatment of a condition or to delay or minimize one or more symptoms associated with the condition. A therapeutically effective amount of a pharmaceutical agent means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a pharmaceutical agent (e.g., a compound of the invention) described herein is an amount sufficient to prevent a condition, or one or more symptoms associated with the condition or prevent its recurrence. A prophylactically effective amount of a pharmaceutical agent means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments, or organelles (such as obtained by lysing cells and separating the components thereof by centrifugation or otherwise). Other examples of biological samples include blood, serum, urine, semen, sputum, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

A "protein" or "peptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. A protein may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The present application refers to various issued patents, published patent applications, journal articles, and other publications, all of which are incorporated herein by reference.

The details of one or more embodiments of the invention are set forth herein. Other features, objects, and advantages of the invention will be apparent from the Detailed Description, the Figures, the Examples, and the Claims.

BRIEF DESCRIPTION OF THE DRAWINGS

Non-limiting embodiments of the present invention will be described by way of example with reference to the accompanying figure, which are schematic and are not intended to be drawn to scale. In the figures, each identical or nearly identical component illustrated is typically represented by a single numeral. For purposes of clarity, not every component is labeled, nor is every component of each embodiment of the invention shown where illustration is not necessary to allow those of ordinary skill in the art to understand the invention. In the figures.

DETAILED DESCRIPTION OF CERTAIN EMBODIMENTS OF THE INVENTION

Figure 1:
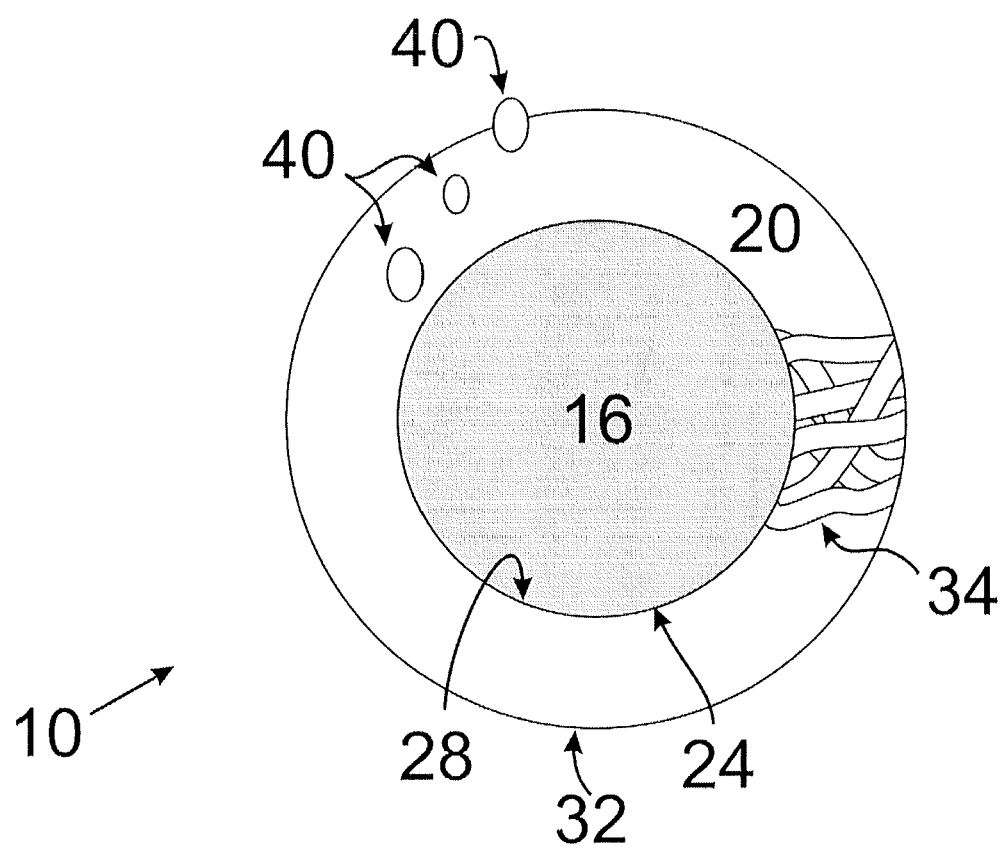
FIG. 1 is a schematic drawing of a mucus-penetrating particle (MPP) comprising a core and a coating.

The present invention provides novel compounds of Formula (I), and pharmaceutically acceptable salts, solvates, hydrates, polymorphs, co-crystals, tautomers, stereoisomers, and isotopically labeled derivatives thereof. The compounds of the invention are derivatives of β-lactam antibiotics. In certain embodiments, the β-lactam antibiotics are carbapenems (e.g., meropenem (1), doripenem (2), ertapenem (3), and imipenem (4) shown below). The derivative typically has a lower aqueous solubility and/or hydrophilicity than the parent β-lactam antibiotic and may be converted in vivo to yield the parent β-lactam antibiotics. Compared to the parent β-lactam antibiotic, the derivative, when administered in a conventional pharmaceutical composition to a subject, may show improved bioavailability (e.g., oral bioavailability). Moreover, the derivative may be more easily processed into mucus-penetrating particles (MPPs) and/or mucus-penetrating crystals (MPCs) suitable for inhalational administration to the respiratory tract of the subject. These advantages of the derivative over the parent β-lactam antibiotic may be due to the lower aqueous solubility and/or hydrophilicity of the derivative.

In one aspect of the present invention, the duration of a β-lactam antibiotic (such as meropenem) is improved by a compound of Formula (I) of the present invention, which has low aqueous solubility and thus is not rapidly absorbed systemically after local deliver to the target tissue (e.g., the lungs). In a further embodiment of the invention, to reduce clearance by mucus, an inventive compound of Formula (I) is formulated as mucus penetrating particles that do not bind to mucus, and once delivered to the lungs (e.g., either in a solution or in an inhalable dry powder formulation that uses larger carrier particles), mucus penetrating particles of the inventive compound dissolve into the compound molecules, which are then rapidly cleaved into the parent β-lactam compound, e.g., meropenem.

The present invention further provides pharmaceutical compositions and kits comprising the inventive compounds. Methods of using and preparing the inventive compounds, pharmaceutical compositions, and kits are also provided by the invention.

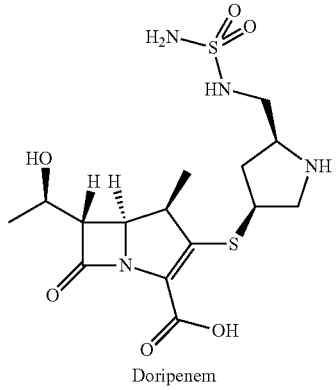

Doripenem (2)

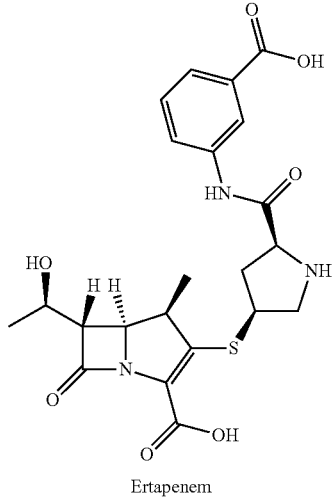

Ertapenem (3)

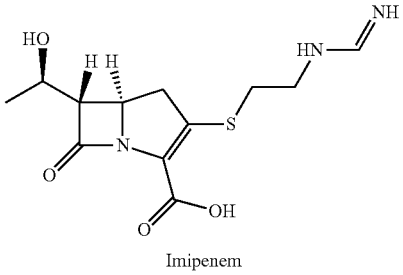

Imipenem (4)

Also provided by the present invention are particles that may penetrate mucus, pharmaceutical compositions thereof, kits, and methods of using and preparing the particles, and pharmaceutical compositions thereof. The pharmaceutical compositions, kits, and methods may involve modifying the surface coatings of particles, such as particles of pharmaceutical agents that have a low aqueous solubility. Such pharmaceutical compositions, kits, and methods can be used to achieve efficient transport of particles comprising the inventive compounds through mucus barriers in a subject.

In certain embodiments, the compounds, particles, pharmaceutical compositions, kits, and methods of the invention are useful for applications in the respiratory tract, such as treating and/or preventing a pulmonary disease (e.g., a respiratory tract infection).

The particles (e.g., nanoparticles and microparticles) of the invention comprise a compound of the invention. The particles of the invention also include a surface-altering agent that modifies the surface of the particles to reduce the adhesion of the particles to mucus and/or to facilitate penetration of the particles through mucus.

The present invention also provides pharmaceutical compositions comprising the inventive particles. In certain embodiments, the pharmaceutical compositions of the invention can be inhalationally administered to the respiratory tract of a subject, such as the upper respiratory tract (e.g., nose and nasal passages, paranasal sinuses, and throat or pharynx), respiratory airways (e.g., voice box or larynx, trachea, bronchi, and bronchioles), and lungs (e.g., respiratory bronchioles, alveolar ducts, alveolar sacs, and alveoli). Inhalable pharmaceutical compositions are advantageous over pharmaceutical compositions that are administered intravenously, intramuscularly, or orally. First, patients are sometimes required to be hospitalized during intravenous or intramuscular administration. Second, intravenous or intramuscular injections are considered by many to be invasive. Third, patients undergoing intravenous, intramuscular, or oral therapy often experience adverse effects associated with systemic drug exposure. In contrast, inhalable pharmaceutical compositions can be administered as in-home therapy, thereby eliminating the additional hospitalization costs associated with intravenous or intramuscular therapy. In addition, inhalable pharmaceutical compositions minimize systemic drug exposure, which frequently decreases adverse reactions.

Delivering drugs to the respiratory tract inhalationally is challenging. Soluble drugs are absorbed rapidly into circulation, and away from target tissue in the lungs, and insoluble drugs are typically trapped by the rapidly cleared mucus layer and hence are rapidly cleared. Therefore, conventional inhalable pharmaceutical compositions currently used to treat pulmonary diseases are often administered at high doses and/or high frequency in order to achieve and sustain efficacy. Such frequent and/or high dosing greatly reduces patient compliance and increases the risk of local adverse effects.

Pharmaceutical compositions of the invention are advantageous over existing inhalable pharmaceutical compositions that are marketed or in late-stage clinical development, such as TOBI®, CAYSTON®, TIP®, and ARIKACE®. These inhalable pharmaceutical compositions are solutions and the drug is absorbed rapidly systemically, and they do not include nanoparticles of drug that mucus-penetrating. In contrast, pharmaceutical compositions of the invention comprise particles of an insoluble compound of the invention that are able to more readily penetrate the mucus layer of the respiratory tract tissue to avoid or minimize mucus adhesion and/or rapid mucus clearance. Therefore, the pharmaceutical compositions of the invention may be more effective in delivering antibiotics to mucus-lined epithelium and may be retained longer in the mucus-containing tissues such as the respiratory tract. As a result, the pharmaceutical compositions of the invention may be administered at a lower dose and/or less frequently than currently marketed pharmaceutical compositions to achieve similar or superior results. Moreover, the relatively low and/or infrequent dosage of the pharmaceutical compositions may result in fewer or less severe side effects, a more desirable toxicity profile, and/or improved patient compliance.

Compounds

β-Lactam antibiotics, such as carbapenems (e.g., meropenem (1), doripenem (2), ertapenem (3), and imipenem (4)), are useful in treating various infectious diseases. They are particularly effective at treating a broad spectrum (including gram-positive, gram-negative, and anaerobic bacteria) of bacterial infections. Prodrugs of beta-lactam antibiotics have been developed to increase absorption, therefore improving oral bioavailability. See, e.g., U.S. Pat. No. 6,410,525 and U.S. Patent Application Publication US 2004/ 0176350, each of which is incorporated by reference in its entirety. Examples of clinically approved drugs that have benefited from the improved oral bioavailability of prodrugs include cefditoren pivoxil, pivampicillin, bacampicillin, and pivmecillinam.

In one aspect, the present invention provides derivatives of β-lactam antibiotics. The derivatives may show higher oral bioavailability than the parent β-lactam compounds. The derivatives may also show lower aqueous solubility and/or higher hydrophobicity than the parent β-lactam antibiotic. Compared to the parent compound, the derivatives with a lower aqueous solubility and/or higher hydrophobicity may be more easily processed into mucus-penetrating particles, crystals, and pharmaceutical composition. The derivative, upon or after being administered to a subject as it is or in the form of mucus-penetrating particles or pharmaceutical compositions comprising the same, may be converted in vivo to provide the parent β-lactam compound.

In certain embodiments, the present invention provides compounds of Formula (I):

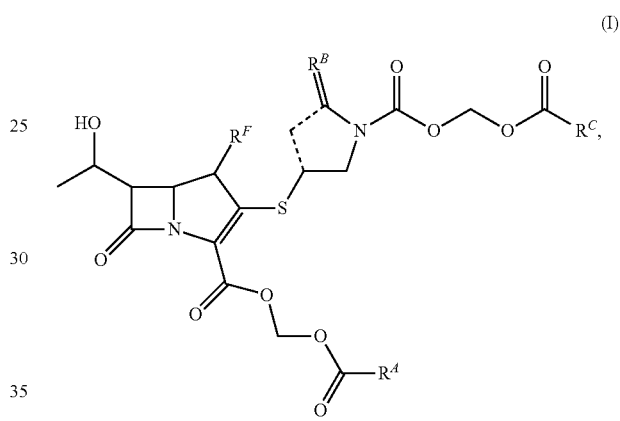

and pharmaceutically acceptable salts, solvates, hydrates, polymorphs, co-crystals, tautomers, stereoisomers, and isotopically labeled derivatives thereof;

wherein:

------ is a single bond or null;

$=\!=\!=$ is a single or double bond;

$R^A$ is substituted or unsubstituted aliphatic, substituted or unsubstituted heteroaliphatic, substituted or unsubstituted carbocyclyl, substituted or unsubstituted heterocyclyl, substituted or unsubstituted aryl, or substituted or unsubstituted heteroaryl;

$R^B$ is $-C(=O)-N(Me)_2$, $-CH_2-NH-S(=O)_2-NH_2$,

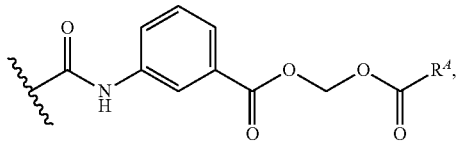

=NH, or

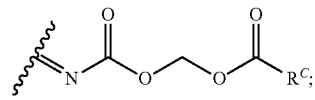

$R^C$ is substituted or unsubstituted aliphatic, substituted or unsubstituted carbocyclyl, substituted or unsubstituted aryl, or substituted or unsubstituted heteroaryl;

$R^F$ is hydrogen or methyl; and provided that when $R^A$ is an unsubstituted $C_4$ aliphatic, then $R^C$ is an unsubstituted $C_6$-$C_{12}$ aliphatic, a substituted aliphatic, substituted or unsubstituted carbocyclyl, substituted or unsubstituted aryl, or substituted or unsubstituted heteroaryl.

In another embodiment, the present invention provides compounds of Formula (I):

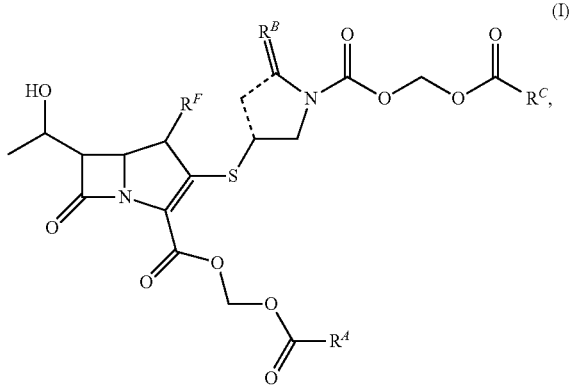

and pharmaceutically acceptable salts, solvates, hydrates, polymorphs, co-crystals, tautomers, stereoisomers, and isotopically labeled derivatives thereof;
wherein:
------ is a single bond or null;
═══ is a single or double bond;
$R^A$ is substituted or unsubstituted aliphatic, substituted or unsubstituted heteroaliphatic, substituted or unsubstituted carbocyclyl, substituted or unsubstituted heterocyclyl, substituted or unsubstituted aryl, or substituted or unsubstituted heteroaryl;
$R^B$ is —C(═O)—N(Me)$_2$, —CH$_2$—NH—S(═O)$_2$—NH$_2$,

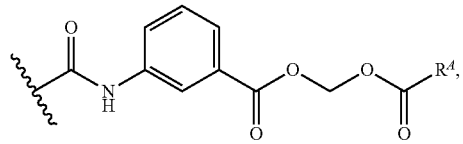

═NH, or

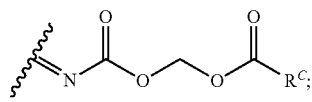

$R^C$ is substituted or unsubstituted aliphatic, substituted or unsubstituted carbocyclyl, substituted or unsubstituted aryl, or substituted or unsubstituted heteroaryl;
$R^F$ is hydrogen or methyl; and
provided that when $R^A$ is an unsubstituted $C_{1-4}$ aliphatic, then $R^C$ is an unsubstituted $C_6$-$C_{12}$ aliphatic, a substituted aliphatic, substituted or unsubstituted carbocyclyl, substituted or unsubstituted aryl, or substituted or unsubstituted heteroaryl.

In certain embodiments, the present invention provides compounds of Formula (I), and pharmaceutically acceptable salts thereof.

In certain embodiments, ------ is a single bond. In certain embodiments, ------ is null.

In certain embodiments, ═══ is a single bond. In certain embodiments, ═══ is a double bond.

A compound of Formula (I) includes substituent $R^A$. In certain embodiments, $R^A$ is substituted aliphatic. In certain embodiments, $R^A$ is unsubstituted aliphatic. The aliphatic group may be branched or unbranched. The aliphatic group may also be saturated or unsaturated and may include any number of double and/or triple bonds as valency permits. In certain embodiments, $R^A$ is substituted $C_{1-12}$ aliphatic. In certain embodiments, $R^A$ is unsubstituted $C_{1-3}$ aliphatic. In certain embodiments, $R^A$ is unsubstituted $C_{1-12}$ aliphatic. In certain embodiments, $R^A$ is unsubstituted $C_{5-12}$ aliphatic. In certain embodiments, $R^A$ is a straight-chained $C_{1-12}$ aliphatic. In certain embodiments, $R^A$ is substituted $C_{1-6}$ aliphatic. In certain embodiments, $R^A$ is unsubstituted $C_{1-6}$ aliphatic. In certain embodiments, $R^A$ is substituted alkyl. In certain embodiments, $R^A$ is unsubstituted alkyl. In certain embodiments, $R^A$ is $C_{1-12}$ alkyl. In certain embodiments, $R^A$ is straight-chained $C_{1-12}$ alkyl. In certain embodiments, $R^A$ is $C_{1-6}$ alkyl. In certain embodiments, $R^A$ is straight-chained $C_{1-6}$ alkyl. In certain embodiments, $R^A$ is methyl. In certain embodiments, $R^A$ is substituted methyl. In certain embodiments, $R^A$ is —CH$_2$F. In certain embodiments, $R^A$ is —CHF$_2$. In certain embodiments, $R^A$ is —CF$_3$. In certain embodiments, $R^A$ is Bn. In certain embodiments, $R^A$ is ethyl. In certain embodiments, $R^A$ is substituted ethyl. In certain embodiments, $R^A$ is —(CH$_2$)$_2$Ph. In certain embodiments, $R^A$ is propyl. In certain embodiments, $R^A$ is butyl. In certain embodiments, $R^A$ is pentyl. In certain embodiments, $R^A$ is hexyl. In certain embodiments, $R^A$ is heptyl. In certain embodiments, $R^A$ is octyl. In certain embodiments, $R^A$ is nonyl. In certain embodiments, $R^A$ is decyl. In certain embodiments, $R^A$ is undecyl. In certain embodiments, $R^A$ is dodecyl. In certain embodiments, $R^A$ is substituted alkenyl. In certain embodiments, $R^A$ is unsubstituted alkenyl. In certain embodiments, $R^A$ is vinyl. In certain embodiments, $R^A$ is substituted alkynyl. In certain embodiments, $R^A$ is unsubstituted alkynyl. In certain embodiments, $R^A$ is ethynyl.

In certain embodiments, $R^A$ is substituted carbocyclyl. In certain embodiments, $R^A$ is unsubstituted carbocyclyl. In certain embodiments, $R^A$ is monocyclic carbocyclyl. In certain embodiments, $R^A$ is substituted or unsubstituted 3- to 7-membered monocyclic carbocyclyl. In certain embodiments, $R^A$ is substituted or unsubstituted cylcopropyl. In certain embodiments, $R^A$ is substituted or unsubstituted cylcobutyl. In certain embodiments, $R^A$ is substituted or unsubstituted cyclopentyl. In certain embodiments, $R^A$ is substituted or unsubstituted cyclohexyl. In certain embodiments, $R^A$ is substituted or unsubstituted cycloheptyl. In certain embodiments, $R^A$ is fused, bridged, or spiro bicyclic carbocyclyl. In certain embodiments, $R^A$ is substituted or unsubstituted 6- to 14-membered bicyclic carbocyclyl.

In certain embodiments, $R^A$ is substituted aryl. In certain embodiments, $R^A$ is unsubstituted aryl. In certain embodiments, $R^A$ is substituted or unsubstituted 6- to 14-membered aryl. In certain embodiments, $R^A$ is unsubstituted phenyl. In certain embodiments, $R^A$ is substituted phenyl. In certain embodiments, $R^A$ is monosubstituted phenyl. In certain embodiments, $R^A$ is ortho-monosubstituted phenyl. In certain embodiments, $R^A$ is meta-monosubstituted phenyl. In certain embodiments, $R^A$ is para-monosubstituted phenyl. In certain embodiments, $R^A$ is disubstituted phenyl. In certain embodiments, $R^A$ is trisubstituted phenyl. In certain embodiments, $R^A$ is tetrasubstituted phenyl. In certain embodiments, $R^A$ is pentasubstituted phenyl. In certain embodiments, $R^A$ is phenyl substituted with one to five substituents independently selected from the group consisting of halogen, substituted or unsubstituted acyl, substituted or unsubstituted aliphatic, substituted or unsubstituted heteroaliphatic, substituted or unsubstituted carbocyclyl, substituted or unsubstituted heterocyclyl, substituted or unsubstituted aryl, or substituted or unsubstituted heteroaryl. In certain embodiments, $R^A$ is phenyl substituted with one to five substituents independently selected from the group consisting of halogen, substituted or unsubstituted $C_{1-12}$ aliphatic, and substituted or unsubstituted $C_{1-12}$ heteroaliphatic including 1-4 heteroatoms independently selected from the group consisting of oxygen, sulfur, and nitrogen. In certain embodiments, $R^A$ is unsubstituted naphthyl. In certain embodiments, $R^A$ is substituted naphthyl.

In certain embodiments, $R^A$ is substituted or unsubstituted heteroaryl. In certain embodiments, $R^A$ is monocyclic, bicyclic (e.g., fused bicyclic), or tricyclic heteroaryl. In certain embodiments, $R^A$ is substituted or unsubstituted, monocyclic, 5- to 7-membered heteroaryl, wherein one, two, or three atoms in the ring of the heteroaryl are independently nitrogen, oxygen, or sulfur. In certain embodiments, $R^A$ is substituted or unsubstituted, bicyclic, 10- to 14-membered heteroaryl, wherein one, two, three, four, or five atoms in the ring of the heteroaryl are independently nitrogen, oxygen, or sulfur.

Each of meropenem (1), doripenem (2), ertapenem (3), and imipenem (4) includes a substituent (i.e., —C(=O)—N(Me)$_2$, —CH$_2$—NH—S(=O)$_2$—NH$_2$,

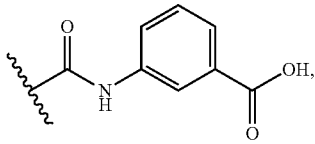 [SMILES: *C(=O)Nc1cccc(C(=O)O)c1]

and =NH, respectively) on the carbon atom α- to the amino moiety of these β-lactam antibiotics. Compounds of Formula (I) also include a substituent $R^B$. In certain embodiments, $R^B$ is of the formula: —C(=O)—N(Me)$_2$. In certain embodiments, $R^B$ is of the formula: —CH$_2$—NH—S(=O)$_2$—NH$_2$. In certain embodiments, $R^B$ is of the formula:

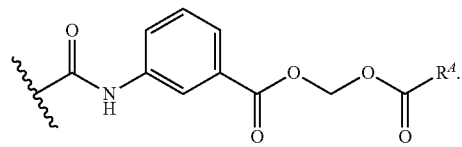

In certain embodiments, $R^B$ is of the formula:

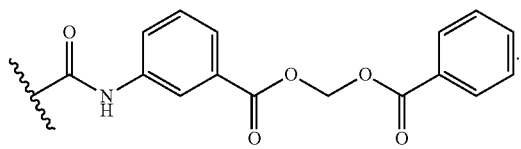 [SMILES: *C(=O)Nc1cccc(C(=O)OCOC(=O)c2ccccc2)c1]

In certain embodiments, $R^B$ is of the formula: =NH. In certain embodiments, $R^B$ is of the formula:

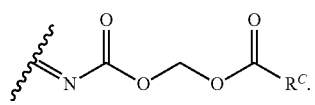

Meropenem (1), doripenem (2), ertapenem (3), and imipenem (4) include —C(=O)—N(Me)$_2$, —CH$_2$—NH—S(=O)$_2$—NH$_2$,

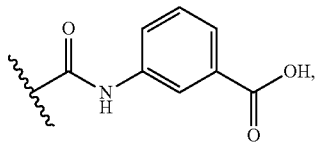 [SMILES: *C(=O)Nc1cccc(C(=O)O)c1]

and =NH respectively.

A compound of Formula (I) includes a substituent $R^C$. In certain embodiments, $R^C$ is substituted aliphatic. In certain embodiments, $R^C$ is unsubstituted aliphatic. The aliphatic group may be branched or unbranched. The aliphatic group may also be saturated or unsaturated and may include any number of double and/or triple bonds as valency permits. In certain embodiments, $R^C$ is substituted $C_{1-12}$ aliphatic. In certain embodiments, $R^C$ is unsubstituted $C_{1-12}$ aliphatic. In certain embodiments, $R^C$ is a straight-chained $C_{1-12}$ aliphatic. In certain embodiments, $R^C$ is substituted $C_{1-6}$ aliphatic. In certain embodiments, $R^C$ is unsubstituted $C_{1-6}$ aliphatic. In certain embodiments, $R^C$ is unsubstituted $C_{6-12}$ aliphatic. In certain embodiments, $R^C$ is substituted alkyl. In certain embodiments, $R^C$ is unsubstituted alkyl. In certain embodiments, $R^C$ is $C_{1-12}$ alkyl. In certain embodiments, $R^C$ is straight-chained $C_{1-12}$ alkyl. In certain embodiments, $R^C$ is $C_{1-6}$ alkyl. In certain embodiments, $R^C$ is straight-chained $C_{1-6}$ alkyl. In certain embodiments, $R^C$ is methyl. In certain embodiments, $R^C$ is substituted methyl. In certain embodiments, $R^C$ is —CH$_2$F. In certain embodiments, $R^C$ is —CHF$_2$. In certain embodiments, $R^C$ is —CF$_3$. In certain embodiments, $R^C$ is Bn. In certain embodiments, $R^C$ is ethyl. In certain embodiments, $R^C$ is substituted ethyl. In certain embodiments, $R^C$ is —(CH$_2$)$_2$Ph. In certain embodiments, $R^C$ is propyl. In certain embodiments, $R^C$ is butyl. In certain embodiments, $R^C$ is pentyl. In certain embodiments, $R^C$ is hexyl. In certain embodiments, $R^C$ is heptyl. In certain embodiments, $R^C$ is octyl. In certain embodiments, $R^C$ is nonyl. In certain embodiments, $R^C$ is decyl. In certain embodiments, $R^C$ is undecyl. In certain embodiments, $R^C$ is dodecyl. In certain embodiments, $R^C$ is substituted alkenyl. In certain embodiments, $R^C$ is unsubstituted alkenyl. In certain embodiments, $R^C$ is vinyl. In certain embodiments, $R^C$ is substituted alkynyl. In certain embodiments, $R^C$ is unsubstituted alkynyl. In certain embodiments, $R^C$ is ethynyl.

In certain embodiments, $R^C$ is substituted carbocyclyl. In certain embodiments, $R^C$ is unsubstituted carbocyclyl. In certain embodiments, $R^C$ is monocyclic carbocyclyl. In certain embodiments, $R^C$ is substituted or unsubstituted 3- to 7-membered monocyclic carbocyclyl. In certain embodiments, $R^C$ is substituted or unsubstituted cylcopropyl. In certain embodiments, $R^C$ is substituted or unsubstituted cylcobutyl. In certain embodiments, $R^C$ is substituted or unsubstituted cyclopentyl. In certain embodiments, $R^C$ is substituted or unsubstituted cyclohexyl. In certain embodiments, $R^C$ is substituted or unsubstituted cycloheptyl. In certain embodiments, $R^C$ is fused, bridged, or spiro bicyclic carbocyclyl. In certain embodiments, $R^C$ is substituted or unsubstituted 6- to 14-membered bicyclic carbocyclyl.

In certain embodiments, $R^C$ is substituted aryl. In certain embodiments, $R^C$ is unsubstituted aryl. In certain embodiments, $R^C$ is substituted or unsubstituted 6- to 14-membered aryl. In certain embodiments, $R^C$ is unsubstituted phenyl. In certain embodiments, $R^C$ is substituted phenyl. In certain embodiments, $R^C$ is monosubstituted phenyl. In certain embodiments, $R^C$ is ortho-monosubstituted phenyl. In certain embodiments, $R^C$ is meta-monosubstituted phenyl. In certain embodiments, $R^C$ is para-monosubstituted phenyl. In certain embodiments, $R^C$ is disubstituted phenyl. In certain embodiments, $R^C$ is trisubstituted phenyl. In certain embodiments, $R^C$ is tetrasubstituted phenyl. In certain embodiments, $R^C$ is pentasubstituted phenyl. In certain embodiments, $R^C$ is phenyl substituted with one to five substituents independently selected from the group consisting of halogen, substituted or unsubstituted acyl, substituted or unsubstituted aliphatic, substituted or unsubstituted heteroaliphatic, substituted or unsubstituted carbocyclyl, substituted or unsubstituted heterocyclyl, substituted or unsubstituted aryl, or substituted or unsubstituted heteroaryl. In certain embodiments, $R^C$ is phenyl substituted with one to five substituents independently selected from the group consisting of halogen, substituted or unsubstituted $C_{1-12}$ aliphatic, and substituted or unsubstituted $C_{1-12}$ heteroaliphatic including 1-4 heteroatoms independently selected from the group consisting of oxygen, sulfur, and nitrogen. In certain embodiments, $R^C$ is unsubstituted naphthyl. In certain embodiments, $R^C$ is substituted naphthyl.

In certain embodiments, $R^C$ is substituted or unsubstituted heteroaryl. In certain embodiments, $R^C$ is monocyclic, bicyclic (e.g., fused bicyclic), or tricyclic heteroaryl. In certain embodiments, $R^C$ is substituted or unsubstituted, monocyclic, 5- to 7-membered heteroaryl, wherein one, two, or three atoms in the ring of the heteroaryl are independently nitrogen, oxygen, or sulfur. In certain embodiments, $R^C$ is substituted or unsubstituted, bicyclic, 10- to 14-membered heteroaryl, wherein one, two, three, four, or five atoms in the ring of the heteroaryl are independently nitrogen, oxygen, or sulfur.

In certain embodiments, $R^A$ and $R^C$ are each substituted 6- to 14-membered aryl. In certain embodiments, $R^A$ and $R^C$ are each unsubstituted 6- to 14-membered aryl. In certain embodiments, $R^A$ and $R^C$ are each substituted phenyl. In certain embodiments, $R^A$ and $R^C$ are each unsubstituted phenyl. In certain embodiments, $R^A$ and $R^C$ are each substituted $C_{1-6}$ alkyl. In certain embodiments, $R^A$ and $R^C$ are each unsubstituted $C_{1-6}$ alkyl. In certain embodiments, $R^A$ and $R^C$ are each substituted, 3- to 7-membered, monocyclic carbocyclyl. In certain embodiments, $R^A$ and $R^C$ are each unsubstituted, 3- to 7-membered, monocyclic carbocyclyl. In certain embodiments, $R^A$ is unsubstituted, 3- to 7-membered, monocyclic carbocyclyl; and $R^C$ is unsubstituted $C_{1-6}$ alkyl. In certain embodiments, $R^C$ is unsubstituted, 3- to 7-membered, monocyclic carbocyclyl; and $R^A$ is unsubstituted $C_{1-6}$ alkyl.

In certain embodiments, $R^F$ is hydrogen. In certain embodiments, $R^F$ is methyl.

In certain embodiments, the compound of Formula (I) is of Formula (I-A):

(I-A)

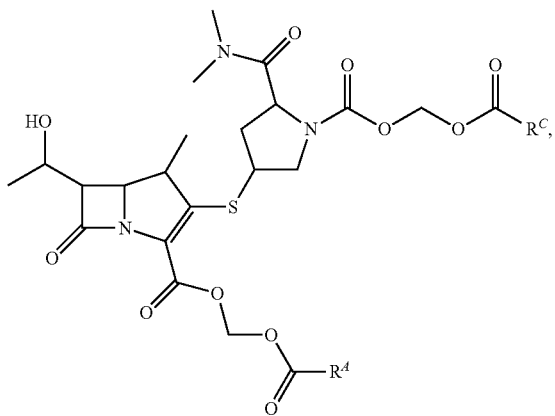

or a pharmaceutically acceptable salt, solvate, hydrate, polymorph, co-crystal, tautomer, stereoisomer, or isotopically labeled derivative thereof.

In certain embodiments, the compound of Formula (I) is of Formula (I-A-1):

(I-A-1)

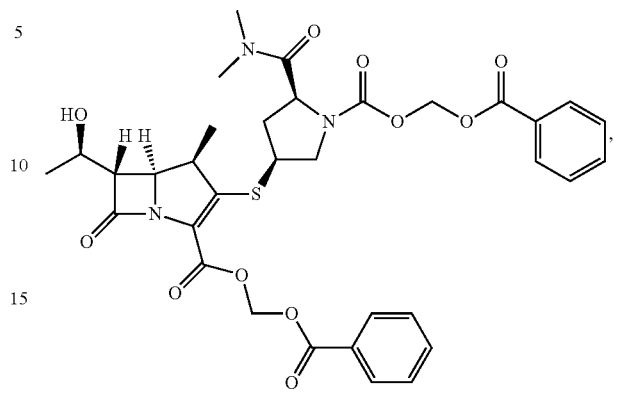

or a pharmaceutically acceptable salt, solvate, hydrate, polymorph, co-crystal, tautomer, stereoisomer, or isotopically labeled derivative thereof.

In certain embodiments, the compound of Formula (I) is of Formula (I-B):

(I-B)

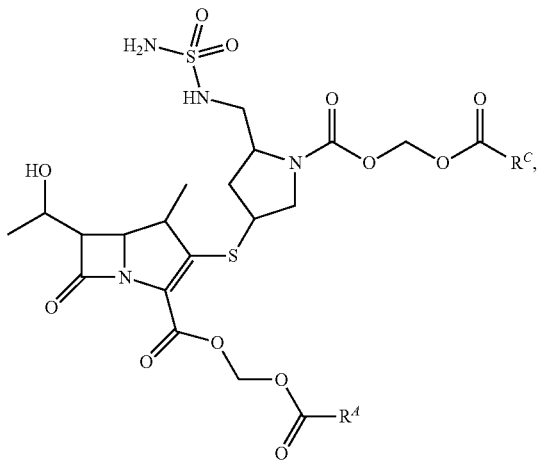

or a pharmaceutically acceptable salt, solvate, hydrate, polymorph, co-crystal, tautomer, stereoisomer, or isotopically labeled derivative thereof.

In certain embodiments, the compound of Formula (I) is of Formula (I-B-1):

(I-B-1)

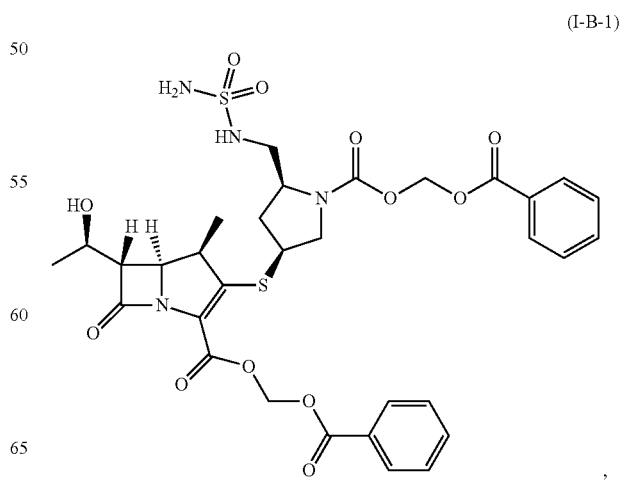

or a pharmaceutically acceptable salt, solvate, hydrate, polymorph, co-crystal, tautomer, stereoisomer, or isotopically labeled derivative thereof.

In certain embodiments, the compound of Formula (I) is of Formula (I-C):

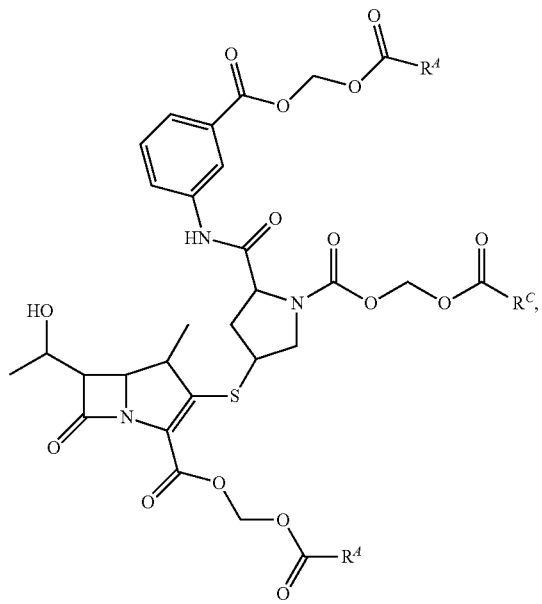
(I-C)

or a pharmaceutically acceptable salt, solvate, hydrate, polymorph, co-crystal, tautomer, stereoisomer, or isotopically labeled derivative thereof.

In certain embodiments, the compound of Formula (I) is of Formula (I-C-1):

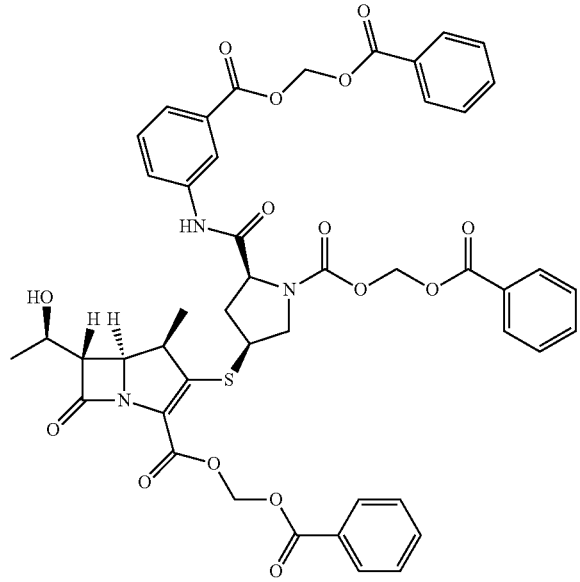
(I-C-1)

or a pharmaceutically acceptable salt, solvate, hydrate, polymorph, co-crystal, tautomer, stereoisomer, or isotopically labeled derivative thereof.

In certain embodiments, the compound of Formula (I) is of Formula (I-D):

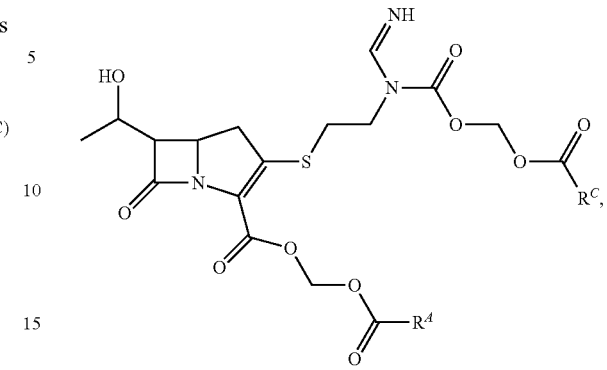
(I-D)

or a pharmaceutically acceptable salt, solvate, hydrate, polymorph, co-crystal, tautomer, stereoisomer, or isotopically labeled derivative thereof.

In certain embodiments, the compound of Formula (I) is of Formula (I-D-1):

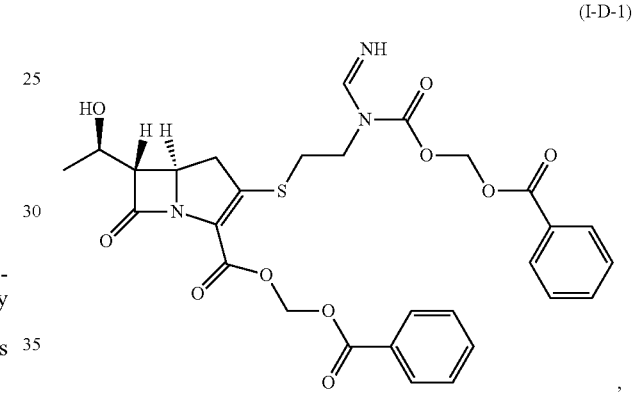
(I-D-1)

or a pharmaceutically acceptable salt, solvate, hydrate, polymorph, co-crystal, tautomer, stereoisomer, or isotopically labeled derivative thereof.

In certain embodiments, the compound of Formula (I) is of Formula (I-E):

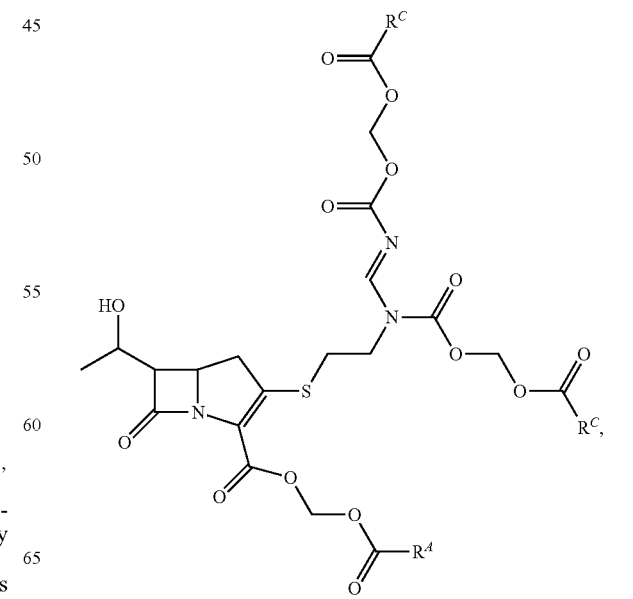
(I-E)

or a pharmaceutically acceptable salt, solvate, hydrate, polymorph, co-crystal, tautomer, stereoisomer, or isotopically labeled derivative thereof.

In certain embodiments, the compound of Formula (I) is of Formula (I-E-1):

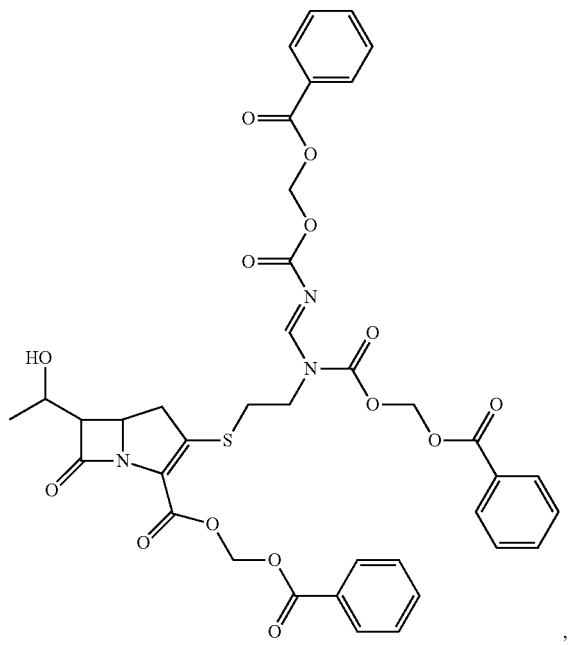

(I-E-1)

or a pharmaceutically acceptable salt, solvate, hydrate, polymorph, co-crystal, tautomer, stereoisomer, or isotopically labeled derivative thereof.

Compounds of the invention may be crystalline. In certain embodiments, the compounds of the invention are monocrystalline. In certain embodiments, the compounds of the invention are polycrystalline.

Compounds of the invention may also have a relatively low aqueous solubility (i.e., a solubility in water, optionally with one or more buffers). In certain embodiments, the aqueous solubility of the compound of the invention is lower than that of the parent β-lactam compound, or pharmaceutically acceptable salts thereof. For example, compounds of the invention may have an aqueous solubility of less than about or equal to about 3 mg/mL, less than about 1 mg/mL, less than about 0.3 mg/mL, less than about 0.1 mg/mL, less than about 0.03 mg/mL, less than about 0.01 mg/mL, less than about 1 μg/mL, less than about 0.1 μg/mL, less than about 0.01 μg/mL, less than about 1 ng/mL, less than about 0.1 ng/mL, or less than about 0.01 ng/mL at 25° C. In some embodiments, the compounds of the invention have an aqueous solubility of at least about 1 μg/mL, at least about 10 μg/mL, at least about 0.1 ng/mL, at least about 1 ng/mL, at least about 10 ng/mL, at least about 0.1 μg/mL, at least about 1 μg/mL, at least about 3 μg/mL, at least about 0.01 mg/mL, at least about 0.03 mg/mL, at least about 0.1 mg/mL, at least about 0.3 mg/mL, at least about 1.0 mg/mL, or at least about 3 mg/mL at 25° C. Combinations of the above-noted ranges are possible (e.g., an aqueous solubility of at least about 10 pg/mL and less than about 1 mg/mL). Other ranges are also possible. The compounds of the invention may have these or other ranges of aqueous solubilities at any point throughout the pH range (e.g., at about pH 7 or from pH 1 to pH 14).

Compounds of the invention may be suitable for being processed into mucus-penetrating pharmaceutical compositions (e.g., particles or crystals). In certain embodiments, the compounds of the invention are suitable for milling (e.g., nano-milling). In certain embodiments, the compounds of the invention are suitable for precipitation (e.g., microprecipitation, nanoprecipitation, crystallization, or controlled crystallization). In certain embodiments, the compounds of the invention are suitable for emulsification. In certain embodiments, the compounds of the invention are suitable for freeze-drying.

The suitability of the compounds of the invention may be due to the relatively low aqueous solubility of the compounds.

Compounds of the invention, as derivatives of the parent β-lactam compounds, may convert (e.g., be hydrolyzed) to provide the parent β-lactam compounds. In certain embodiments, the compounds of the invention are hydrolyzed to provide compounds of Formula (II):

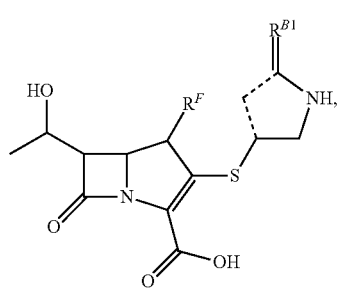

(II)

and pharmaceutically acceptable salts, solvates, hydrates, polymorphs, co-crystals, tautomers, stereoisomers, and isotopically labeled derivatives thereof; wherein:

------, ====, and $R^F$ are as described herein; and $R^{B1}$ is —C(=O)—N(Me)$_2$, —CH$_2$—NH—S(=O)$_2$—NH$_2$,

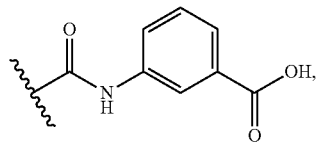 [SMILES: *C(=O)Nc1cccc(C(=O)O)c1]

or =NH.

The conversion of the compounds of the invention may occur in vitro, ex vitro, or in vivo. The conversion of the compounds of the invention may occur at any point from 0 to 100° C. (e.g., at about 37 OC or from 20 to 40° C.) and at any pH (e.g., at about pH 7 or from pH 1 to pH 14). In certain embodiments, the conversion of the compounds of the invention occurs under physiological conditions. The compounds of the invention may be biologically converted, e.g., by enzymatic activity or cellular machinery. The compounds of the invention may also be chemically converted, e.g., not by enzymatic activity or cellular machinery. The half-life of the compounds of the invention (the time at which 50% of the compounds of the invention are converted into compounds of Formula (II) and/or other compounds) may be on the order of minutes, hours (e.g., about 1 hour, about 2 hours, about 6 hours, and about 12 hours), days (e.g., about 1 day, about 2 days, about 3 days, and about 5 days), and weeks. The compounds of the invention may convert to yield other compounds in addition to the parent β-lactam compounds. In certain embodiments, the other compounds are those cells can either reuse or dispose of without significant toxic effect on the cells (i.e., fewer than about 20% of the cells are killed when contacted with the other compounds).

Methods of Preparing the Inventive Compounds

In another aspect, the present application provides methods of preparing the compounds of the invention. The inventive compounds are derivatives of certain β-lactam antibiotics (e.g., meropenem (1), doripenem (2), and ertapenem (3)). Compared to the parent β-lactam antibiotics, the inventive compounds may be more hydrophobic and/or less water-soluble. The compounds of the invention may be synthesized by converting the polar moieties, especially, groups that may be protonated or deprotonated to carry positive or negative charges at certain pH ranges (e.g., amino and carboxyl groups), of a parent β-lactam antibiotic to less polar groups (e.g., carbamates and esters). It is also desired that the less polar groups are capable of being converted (e.g., being hydrolyzed) into the polar moieties in vivo. In certain embodiments, the methods of preparing the compounds include reacting a compound of Formula (i-A), or a salt, tautomer, stereoisomer, or isotopically labeled derivative thereof, with a compound of Formula (i-B) to provide a compound of Formula (i-C), or a salt, tautomer, stereoisomer, or isotopically labeled derivative thereof:

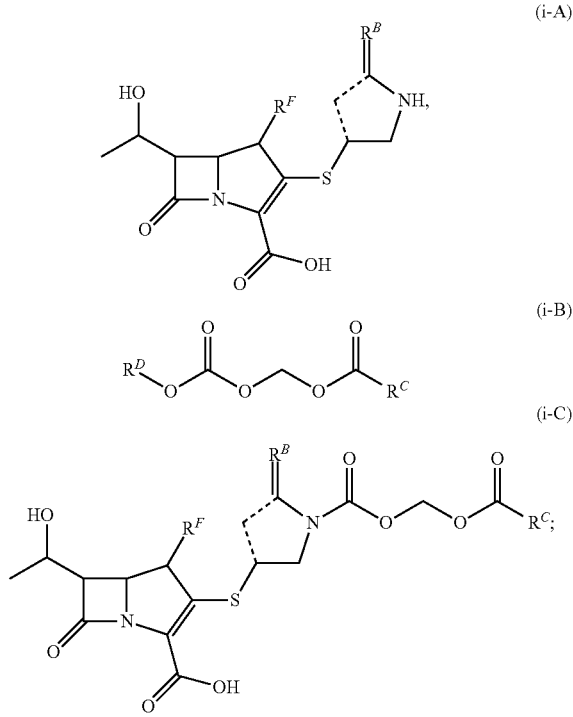

reacting the compound of Formula (i-C), or the salt, tautomer, stereoisomer, or isotopically labeled derivative thereof, with a base and a compound of Formula (i-D) to provide the compound of Formula (I), or a pharmaceutical acceptable salt, solvate, hydrate, polymorph, co-crystal, tautomer, stereoisomer, or isotopically labeled derivative thereof:

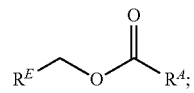

wherein:
$R^A$, $R^B$, $R^C$, and $R^F$ are as described herein;
$R^D$ is an electron-withdrawing group; and
$R^E$ is a leaving group.

A compound of Formula (i-A), or a salt, tautomer, stereoisomer, or isotopically labeled derivative thereof, include an amino group and one (when $R^B$ is —C(=O)—N(Me)$_2$ or —CH$_2$—NH—S(=O)$_2$—NH$_2$) or two (when $R^B$ is

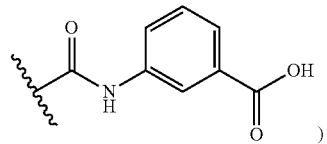

)

carboxyl groups, Compared to the carboxyl group(s), the amino group of a compound of Formula (i-A) is more nucleophilic and may react with an electrophile, such as an ester (e.g., a carbonate, such as a compound of Formula (i-B), or a salt, tautomer, stereoisomer, or isotopically labeled derivative thereof) to form a substitution reaction intermediate (i-C), or a salt, tautomer, stereoisomer, or isotopically labeled derivative thereof, while the carboxyl group(s) remains unreacted. In certain embodiments, the inventive methods include reacting a compound of Formula (i-A), or a salt, tautomer, stereoisomer, or isotopically labeled derivative thereof, with a substantially stoichiometric amount of a compound of Formula (i-B).

A base is employed in the inventive methods of preparing the compounds of the invention. In certain embodiments, the base is an inorganic base. In certain embodiments, the inorganic base is ammonia. In certain embodiments, the inorganic base is ammonium carbonate. In certain embodiments, the inorganic base is ammonium hydroxide. In certain embodiments, the inorganic base is an alkali metal phosphate tribasic. In certain embodiments, the inorganic base is Li$_3$PO$_4$, Na$_3$PO$_4$, K$_3$PO$_4$, Rb$_3$PO$_4$, or Cs$_3$PO$_4$. In certain embodiments, the inorganic base is an alkali metal phosphate dibasic. In certain embodiments, the inorganic base is Li$_2$HPO$_4$, Na$_2$HPO$_4$, K$_2$HPO$_4$, Rb$_2$HPO$_4$, or Cs$_2$HPO$_4$. In certain embodiments, the inorganic base is an alkali metal phosphate monobasic. In certain embodiments, the inorganic base is LiH$_2$PO$_4$, NaH$_2$PO$_4$, KH$_2$PO$_4$, RbH$_2$PO$_4$, or CsH$_2$PO$_4$. In certain embodiments, the inorganic base is an alkali metal carbonate. In certain embodiments, the inorganic base is Li$_2$CO$_3$, Na$_2$CO$_3$, K$_2$CO$_3$, Rb$_2$CO$_3$, or Cs$_2$CO$_3$. In certain embodiments, the inorganic base is an alkali metal bicarbonate. In certain embodiments, the inorganic base is LiHCO$_3$, NaHCO$_3$, KHCO$_3$, RbHCO$_3$, or CsHCO$_3$. In certain embodiments, the inorganic base is an alkali metal hydroxide. In certain embodiments, the inorganic base is LiOH, NaOH, KOH, RbOH, or CsOH. In certain embodiments, the inorganic base is an alkaline earth metal carbonate. In certain embodiments, the inorganic base is BeCO$_3$, MgCO$_3$, CaCO$_3$, SrCO$_3$, or BaCO$_3$. In certain embodiments, the inorganic base is an alkaline earth metal bicarbonate. In certain embodiments, the inorganic base is Be(HCO$_3$)$_2$, Mg(HCO$_3$)$_2$, Ca(HCO$_3$)$_2$, Sr(HCO$_3$)$_2$, or Ba(HCO$_3$)$_2$. In certain embodiments, the inorganic base is an alkaline earth metal hydroxide. In certain embodiments, the inorganic base is Be(OH)$_2$, Mg(OH)$_2$, Ca(OH)$_2$, Sr(OH)$_2$, or Ba(OH)$_2$. In certain embodiments, the base is an organic base. In certain embodiments, the organic base is an aliphatic amine. In certain embodiments, the organic base is an aromatic amine. In certain embodiments, the organic base is a primary amine. In certain embodiments, the organic base is a secondary amine. In certain embodiments, the organic base is a tertiary amine. In certain embodiments, the organic base is triethyl amine, N,N-diisopropylethylamine, or 1,8-diazabicyclo[5.4.0]undec-7-ene (DBU). In certain embodiments, the organic base is substituted pyridine. In certain embodiments, the organic base is 2,6-lutidine or 4-dimethylaminopyridine (DMAP). In certain embodiments, the organic base is unsubstituted pyridine.

Compounds of Formula (i-B) include an electron-withdrawing group as $R^D$. All electron-withdrawing groups described herein and known in the art are contemplated as being within the scope of the invention. In certain embodiments, $R^D$ is phenyl substituted with one or more substituents, wherein at least one substituent is halogen, partially or fully halogenated aliphatic, cyclopropyl, partially or fully halogenated carbocyclyl, —N($R^{D1}$)$_3^+$, —CN, —NO$_2$, —C(=N$R^{D1}$)$R^{D1}$, —C(=N$R^{D1}$)O$R^{D1}$, —C(=N$R^{D1}$)N($R^{D1}$)$_2$, —C(=O)$R^{D1}$, —C(=O)O$R^{D1}$, —C(=O)N($R^{D1}$)$_2$, —S(=O)$R^{D1}$, —S(=O)O$R^{D1}$, —S(=O)N($R^{D1}$)$_2$, —S(=O)$_2$$R^{D1}$, —S(=O)$_2$O$R^{D1}$, S(=O)$_2$N($R^{D1}$)$_2$, —OS(=O)$R^{D1}$, —OS(=O)O$R^{D1}$, —OS(=O)N($R^{D1}$)$_2$, —OS(=O)$_2$$R^{D1}$, —OS(=O)$_2$O$R^{D1}$, or —OS(=O)$_2$N($R^{D1}$)$_2$, wherein each instance of $R^{D1}$ is independently substituted or unsubstituted aliphatic, substituted or unsubstituted heteroaliphatic, substituted or unsubstituted carbocyclyl, substituted or unsubstituted heterocyclyl, substituted or unsubstituted aryl, or substituted or unsubstituted heteroaryl. In certain embodiments, $R^D$ is phenyl substituted with one or more substituents, wherein at least one substituent is —NO$_2$. In certain embodiments, $R^D$ is of the formula:

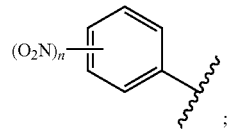

and n is 1 or 2. In certain embodiments, $R^D$ is of the formula:

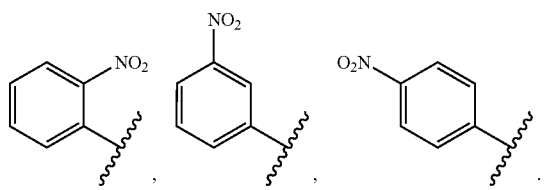 [SMILES: *c1ccccc1[N+](=O)[O-] ; *c1cccc([N+](=O)[O-])c1 ; *c1ccc([N+](=O)[O-])cc1]

In certain embodiments, $R^D$ is phenyl substituted with one or more substituents, wherein at least one substituent is —CN. In certain embodiments, $R^D$ is of the formula:

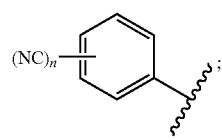

and n is 1, 2, or 3. In certain embodiments, $R^D$ is of the formula:

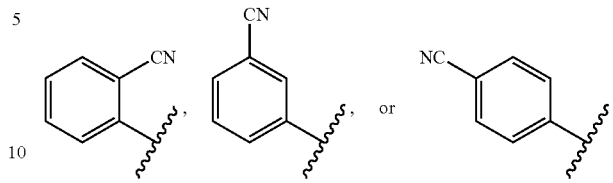

Compounds of Formula (i-D) include a leaving group as $R^E$. All leaving groups described herein and known in the art are contemplated as being within the scope of the invention. In certain embodiments, $R^E$ is halogen. In certain embodiments, $R^E$ is F. In certain embodiments, $R^E$ is Cl. In certain embodiments, $R^E$ is Br. In certain embodiments, $R^E$ is I (iodine). In certain embodiments, $R^E$ is —OS(=O)$_w$$R^{E1}$. In certain embodiments, w is 1. In certain embodiments, w is 2. In certain embodiments, $R^E$ is —OMs. In certain embodiments, $R^E$ is —OTf. In certain embodiments, $R^E$ is —OTs. In certain embodiments, $R^E$ is —OBs. In certain embodiments, $R^E$ is 2-nitrobenzenesulfonyloxy. In certain embodiments, $R^E$ is —O$R^{E1}$. In certain embodiments, $R^E$ is —OMe. In certain embodiments, $R^E$ is —OCF$_3$. In certain embodiments, $R^E$ is —OPh. In certain embodiments, $R^E$ is —OC(=O)$R^{E1}$. In certain embodiments, $R^E$ is —OC(=O)Me. In certain embodiments, $R^E$ is —OC(=O)CF$_3$. In certain embodiments, $R^E$ is —OC(=O)Ph. In certain embodiments, $R^E$ is —OC(=O)Cl. In certain embodiments, $R^E$ is —OC(=O)O$R^{E1}$. In certain embodiments, $R^E$ is —OC(=O)OMe. In certain embodiments, $R^E$ is —OC(=O)O(t-Bu). In certain embodiments, $R^{E1}$ is substituted aliphatic. In certain embodiments, $R^{E1}$ is unsubstituted aliphatic. In certain embodiments, $R^{E1}$ is substituted alkyl. In certain embodiments, $R^{E1}$ is unsubstituted alkyl. In certain embodiments, $R^{E1}$ is $C_{1-6}$ alkyl. In certain embodiments, $R^{E1}$ is methyl. In certain embodiments, $R^{E1}$ is ethyl. In certain embodiments, $R^{E1}$ is propyl. In certain embodiments, $R^{E1}$ is butyl. In certain embodiments, $R^{E1}$ is substituted alkenyl. In certain embodiments, $R^{E1}$ is unsubstituted alkenyl. In certain embodiments, $R^{E1}$ is vinyl. In certain embodiments, $R^{E1}$ is substituted alkynyl. In certain embodiments, $R^{E1}$ is unsubstituted alkynyl. In certain embodiments, $R^{E1}$ is ethynyl. In certain embodiments, $R^{E1}$ is substituted heteroaliphatic. In certain embodiments, $R^{E1}$ is unsubstituted heteroaliphatic. In certain embodiments, $R^{E1}$ is substituted carbocyclyl. In certain embodiments, $R^{E1}$ is unsubstituted carbocyclyl. In certain embodiments, $R^{E1}$ is substituted heterocyclyl. In certain embodiments, $R^{E1}$ is unsubstituted heterocyclyl. In certain embodiments, $R^{E1}$ is substituted aryl. In certain embodiments, $R^{E1}$ is unsubstituted aryl. In certain embodiments, $R^{E1}$ is substituted phenyl. In certain embodiments, $R^{E1}$ is unsubstituted phenyl. In certain embodiments, $R^{E1}$ is substituted heteroaryl. In certain embodiments, $R^{E1}$ is unsubstituted heteroaryl. In certain embodiments, $R^{E1}$ is substituted pyridyl. In certain embodiments, $R^{E1}$ is unsubstituted pyridyl.

The steps of the methods of preparing the compounds of the invention may be performed under any suitable conditions. A suitable condition is a combination of physical and chemical parameters under which an inventive compound of the invention or intermediate thereto may be formed using the inventive methods. A suitable condition may include a suitable solvent, such as an organic solvent (e.g., e.g., acetone, acetonitrile (ACN), N,N-dimethylformamide (DMF), N,N-dimethylacetamide (DMA), dimethysulfoxide (DMSO), N-methyl-2-pyrrolidone (NMP), 2-pyrrolidone, tetrahydrofuran (THF), or a mixture thereof), an inorganic solvent (e.g., water)), or a mixture thereof. In certain embodiments, the suitable solvent is DMF.

A suitable condition may also include a suitable temperature under which one or more steps of a method of preparing the compounds of the invention are performed. In certain embodiments, the suitable temperature is at least about 0° C., at least about 20° C., at least about 25° C., at least about 40° C., at least about 60° C., at least about 80° C., or at least about 100° C. In certain embodiments, the suitable temperature is lower than about 100° C., lower than about 80° C., lower than about 60° C., lower than about 40° C., lower than about 25° C., lower than about 20° C., or lower than about 0° C. Combinations of the above-referenced ranges are also possible (e.g., a suitable temperature of at least about 0° C. and lower than about 40° C.). Other ranges are also possible. In certain embodiments, the suitable temperature is about 20° C. A suitable temperature may be a variable temperature during one or more steps of a method of preparing the compounds.

A suitable condition may also include a suitable pressure under which one or more steps of the inventive methods are performed. In certain embodiments, the suitable pressure is about 1 atmosphere. A suitable pressure may also be higher or lower than 1 atmosphere.

A suitable condition may also include a suitable atmosphere under which one or more steps of the inventive methods of preparing the compounds of the invention are performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that one or more steps of a method of preparing the compounds of the invention last. In certain embodiments, the suitable time duration is in the order of minutes, hours, or days.

A suitable condition may also include irradiation with microwave and/or stirring. One or more intermediates (e.g., a compound of Formula (i-C), or a salt, tautomer, stereoisomer, or isotopically labeled derivative thereof) resulting from a step of a method of preparing the compounds of the invention may be isolated and/or purified, and the isolated and/or purified intermediates may be reacted in a next step of the method. The isolated and/or purified intermediates may be substantially pure or may contain one or more other components, such as reagents and solvents employed in the step yielding the intermediates and byproducts. The one or more intermediates may also be reacted in the next step without being isolated and/or purified.

Pharmaceutical Compositions, Kits, and Uses

The present invention provides pharmaceutical compositions comprising a compound of the invention, such as a compound of Formula (I), or a pharmaceutically acceptable salt, solvate, hydrate, polymorph, co-crystal, tautomer, stereoisomer, or isotopically labeled derivative thereof, and optionally a pharmaceutically acceptable excipient.

The present invention also provides pharmaceutical compositions comprising a plurality of particles of the invention, which may be mucus-penetrating and may include a pharmaceutical agent (e.g., a compound of the invention). The inventive pharmaceutical compositions may be useful to deliver the pharmaceutical agent to the respiratory tract of a subject and to treat and/or prevent a respiratory tract disease of the subject.

In another embodiment, the present invention further provides a formulation, in the form of inhalable dry powder, comprising a compound of Formula (I), or a pharmaceutically acceptable salt, solvate, hydrate, polymorph, co-crystal, tautomer, stereoisomer, and isotopically labeled derivative thereof, wherein the compound is formulated with pharmaceutically acceptable carrier particles, and optionally, one or more additional pharmaceutically acceptable excipients. In one embodiment, the compound of Formula (I) is formulated as a plurality of nanoparticles that have reduced mucoadhesion.

Figure 2:
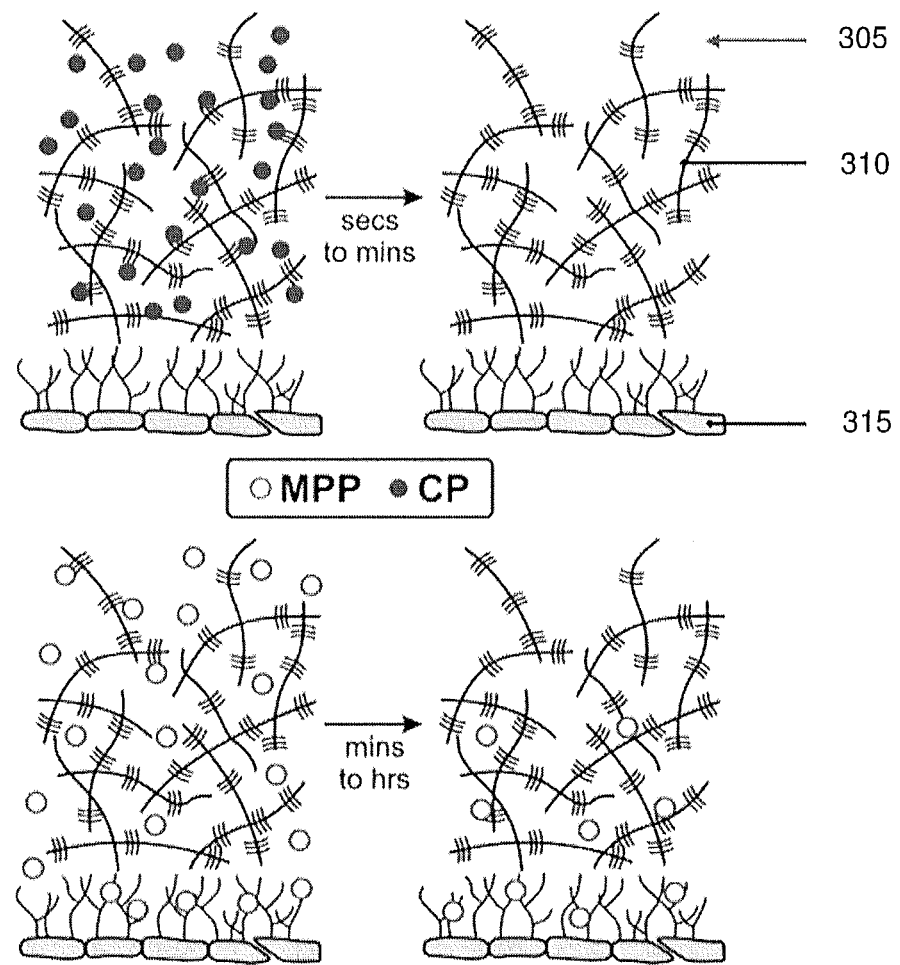
FIG. 2 is a schematic drawing showing MPPs and conventional particles in a mucus layer of the respiratory tract of a subject after inhalational administration of the particles. The MPPs readily penetrate the outer mucus layer toward the glycocalyx while the conventional particles (CPs) are immobilized in the outer layer of mucus. The clearance of the outer layer by the subject's natural clearance mechanisms may be accompanied by removal of the pharmaceutical composition, whereas MPPs are retained in the less rapidly cleared glycocalyx, leading to prolonged residence at the surface of the respiratory tract.

As shown illustratively in FIG. 2, the outer layer of a respiratory tract of a subject is comprised of secreted mucins 310 which may be cleared rapidly by mucin turnover, whose primary role is to trap and eliminate allergens, pathogens, and debris (including drug particles) from the aqueous layer 305 of the respiratory tract. The inner layer (thickness up to 500 nm) is formed by mucins tethered to epithelium 315 (glycocalyx), which protects the underlying tissue from abrasive stress and are cleared less rapidly. Without wishing to be bound by theory, it is believed that conventional particles (CPs, e.g., non-MPPs) are trapped in the outer mucus layer and are readily cleared from the surface of the respiratory tract. Thus, the conventional particles may be cleared before the drugs contained in the particles can be transported to other portions of the respiratory tract (e.g., by diffusion or other mechanisms). In contrast, the particles of the invention (e.g., MPPs) may avoid adhesion to secreted mucins, and thus may penetrate the peripheral mucus layer and reach the slow-clearing glycocalyx, thereby prolonging particle retention and sustaining drug release (FIG. 2). This suggests that the particles of the invention may deliver drugs to underlying tissues of the respiratory tract much more efficiently than CPs trapped in outer mucus.

The present invention also provides methods of increasing the coverage uniformity of the inventive particles and/or of pharmaceutical agents included in the particles over the surface of a target tissue of the respiratory tract. The pharmaceutical compositions of the invention may create an even coverage of particles and/or pharmaceutical agent over a large area of the surface of the respiratory tract, where a conventional formulation without the coatings described herein may not spread as evenly due to their immobilization in mucus, Therefore, the pharmaceutical compositions of the invention may enhance efficacy by more uniform coverage. This in turn, with or without higher concentrations, may enhance penetration through mucus. The present invention provides particles, and pharmaceutical compositions comprising the same, that are mucus-penetrating and can address the issues associated with delivery of a pharmaceutical agent to the mucus of and/or a target tissue of the respiratory tract of a subject. The particles may avoid adhesion to the mucus and/or may be more evenly spread across the surface of the respiratory tract, thereby avoiding the respiratory tract's clearance mechanisms and prolonging their residence time in the mucus, which may be useful in delivering a pharmaceutical agent to the mucus of the respiratory tract and in treating and/or preventing a respiratory tract disease caused by pathogenic microorganisms in the mucus. For example, the particles in mucus may readily diffuse, e.g., driven by the Brownian motion of the particles and optionally a concentration gradient, to another area of the mucus, such as where the concentration of the particles is lower (e.g., mucus freshly generated by the respiratory tract). Moreover, the mobile particles may effectively penetrate through mucus to reach a target tissue of the respiratory tract underneath the mucus, and therefore, may be useful in delivering a pharmaceutical agent to the target tissue and in treating and/or preventing a respiratory tract disease that is caused by pathogenic microorganisms in the target tissue.

In some embodiments, the particles of the invention have a core-shell type configuration. The core may comprise any suitable material such as a solid pharmaceutical agent or a salt thereof having a relatively low aqueous solubility, a polymeric carrier, a lipid, and/or a protein. The core may also comprise a gel or a liquid. The core may be coated with a coating or shell comprising a surface-altering agent that facilitates mobility of the particle in mucus. As described in more detail below, the surface-altering agent may comprise a polymer (e.g., a synthetic or a natural polymer) having pendant hydroxyl groups on the backbone of the polymer. The molecular weight and/or degree of hydrolysis of the polymer may be chosen to impart certain transport characteristics to the particles, such as increased transport through mucus. In certain embodiments, the surface-altering agent may comprise a triblock copolymer comprising a (hydrophilic block)-(hydrophobic block)-(hydrophilic block) configuration. The molecular weights of each one of the blocks may be chosen to impart certain transport characteristics to the particles, such as increased transport through mucus. In some embodiments, at least one particle of the invention includes a core and a coating surrounding the core. A particle including a core and a coating on the core is referred to as a "coated particle." In certain embodiments, at least one particle of the invention includes a core but not a coating on the core. A particle including a core but not a coating on the core is referred to as an "uncoated particle."

Non-limiting examples of particles are now provided. As shown in the illustrative embodiment of FIG. 1, a particle 10 includes a core 16 (which may be in the form of a particle, referred to herein as a core) and a coating 20 surrounding the core. In some embodiments, a substantial portion of the core is formed of one or more solid pharmaceutical agents (e.g., a compound of the invention) that can lead to certain beneficial and/or therapeutic effects. The core may be, for example, a nanocrystal (i.e., a nanocrystalline particle) of a pharmaceutical agent. In certain embodiments, the core includes a polymeric carrier, optionally with one or more pharmaceutical agents encapsulated or otherwise associated with the core. In certain embodiments, the core includes a lipid, protein, gel, liquid, and/or another suitable material to be delivered to a subject. The core includes a surface 24 to which one or more surface-altering agents can be attached. In some embodiments, core 16 is surrounded by coating 20, which includes an inner surface 28 and an outer surface 32. The coating may be formed, at least in part, of one or more surface-altering agents 34, such as a polymer (e.g., a block copolymer and/or a polymer having pendant hydroxyl groups), which may associate with surface 24 of the core. Surface-altering agent 34 may be associated with the core particle by, for example, being covalently attached to the core particle, non-covalently attached to the core particle, adsorbed to the core, or attached to the core through ionic interactions, hydrophobic and/or hydrophilic interactions, electrostatic interactions, van der Waals interactions, or combinations thereof. In some embodiments, the surface-altering agents, or portions thereof, are chosen to facilitate transport of the particle through or into a mucosal barrier (e.g., mucus or a mucosal membrane). In certain embodiments described herein, one or more surface-altering agents 34 are oriented in a particular configuration in the coating.

In some embodiments, in which a surface-altering agent is a triblock copolymer, such as a triblock copolymer having a (hydrophilic block)-(hydrophobic block)-(hydrophilic block) configuration, a hydrophobic block may be oriented towards the surface of the core, and hydrophilic blocks may be oriented away from the core surface (e.g., towards the exterior of the particle). The hydrophilic blocks may have characteristics that facilitate transport of the particle through a mucosal barrier, as described in more detail below.

Particle 10 may optionally include one or more components 40 such as targeting moieties, proteins, nucleic acids, and bioactive agents which may optionally impart specificity to the particle. For example, a targeting agent or molecule (e.g., a protein, nucleic acid, nucleic acid analog, carbohydrate, or small molecule), if present, may aid in directing the particle to a specific location in the subject's body. The location may be, for example, a tissue, a particular cell type, or a subcellular compartment. One or more components 40, if present, may be associated with the core, the coating, or both; e.g., they may be associated with surface 24 of the core, inner surface 28 of the coating, outer surface 32 of the coating, and/or embedded in the coating. The one or more components 40 may be associated through covalent bonds or absorption, or attached through ionic interactions, hydrophobic, and/or hydrophilic interactions, electrostatic interactions, van der Waals interactions, or combinations thereof. In some embodiments, a component may be attached (e.g., covalently) to one or more of the surface-altering agents of the particle using methods known to those skilled in the art.

It should be understood that components and configurations other than those shown in FIG. 1 or described herein may be suitable for certain particles and pharmaceutical compositions, and that not all of the components shown in FIG. 1 are necessarily present in some embodiments.

In some embodiments, particle 10, when introduced into a subject, may interact with one or more components in the subject such as mucus, cells, tissues, organs, particles, fluids (e.g., blood), microorganisms, and portions or combinations thereof. In some embodiments, the coating of particle 10 can be designed to include surface-altering agents or other components with properties that allow favorable interactions (e.g., transport, binding, and adsorption) with one or more materials from the subject. For example, the coating may include surface-altering agents or other components having a certain hydrophilicity, hydrophobicity, surface charge, functional group, specificity for binding, and/or density to facilitate or reduce particular interactions in the subject. One example is choosing a hydrophilicity, hydrophobicity, surface charge, functional group, specificity for binding, and/or density of one or more surface-altering agents to reduce the physical and/or chemical interactions between the particle and mucus of the subject, so as to enhance the mobility of the particle through mucus. Other examples are described in more detail below.

In some embodiments, once a particle is successfully transported into and/or across a mucosal barrier (e.g., mucus or a mucosal membrane) in a subject, further interactions between the particle and the subject may take place. Interactions may take place through the coating and/or the core and may involve, for example, the exchange of materials (e.g., pharmaceutical agents, therapeutic agents, proteins, peptides, polypeptides, nucleic acids, and nutrients) from the one or more components of the subject to particle 10, and/or from particle 10 to the one or more components of the subject. In some embodiments, in which the core comprises a pharmaceutical agent, the conversion, breakdown, release, and/or transport of the pharmaceutical agent from the particle can lead to certain beneficial and/or therapeutic effects in the subject. Therefore, the particles of the invention can be used for the treatment and/or prevention of certain diseases. When the diseases are caused by pathogenic microorgansims, similar interactions between the particle and the microorgansims may also take place.

Examples for the use of the particles of the invention are provided below in the context of being suitable for administration to a mucosal barrier (e.g., mucus or a mucosal membrane) in a subject. It should be appreciated that while many of the embodiments herein are described in this context, and in the context of providing a benefit for diseases that involve transport of materials across a mucosal barrier, the invention is not limited as such, and the particles, pharmaceutical compositions, and kits of the invention may be used to treat and/or prevent other diseases.

In some embodiments, the pharmaceutical compositions of the invention comprise MPPs that include a compound of the invention and optionally at least one additional pharmaceutical agent, each of which is associated with polymer carriers via encapsulation or other processes. In other embodiments, the pharmaceutical compositions of the invention comprise MPPs without any polymeric carriers or with minimal use of polymeric carriers. Polymer-based MPPs may have one or more inherent limitations in some embodiments. In particular, in light of drug delivery applications, these limitations may include one or more of the following. A) Low drug encapsulation efficiency and low drug loading: encapsulation of drugs into polymeric particles is often inefficient, as generally less than 10% of the total amount of drug used gets encapsulated into particles during manufacturing; additionally, drug loadings above 50% are rarely achieved. B) Convenience of usage: pharmaceutical compositions based on drug-loaded polymeric particles, in general, typically need to be stored as dry powder to avoid premature drug release and thus require either point-of-use re-constitution or a sophisticated dosing device. C) Biocompatibility: accumulation of slowly degrading polymer carriers following repeated dosing and their toxicity over the long term present a major concern for polymeric drug carriers. D) Chemical and physical stability: polymer degradation may compromise stability of encapsulated drugs. In many encapsulation processes, the drug undergoes a transition from a solution phase to a solid phase, which is not well-controlled in terms of physical form of the emerging solid phase (i.e., amorphous vs. crystalline vs. crystalline polymorphs); this is a concern for multiple aspects of pharmaceutical composition performance, including physical and chemical stability and release kinetics. E) Manufacturing complexity: manufacturing, especially scalability, of drug-loaded polymeric MPPs is a fairly complex process that may involve multiple steps and a considerable amount of toxic organic solvents. Therefore, by avoiding or minimizing the need to encapsulate pharmaceutical agents into polymeric carriers, certain limitations of polymeric MPPs with respect to drug loading, convenience of usage, biocompatibility, stability, and/or complexity of manufacturing, may be addressed. The methods and compositions described herein may facilitate clinical development of the mucus-penetrating particle technology.

It should be appreciated, however, that in other embodiments, pharmaceutical agents may be associated with polymer carriers via encapsulation or other processes. Thus, the description provided herein is not limited in this respect. For instance, despite the above-mentioned drawbacks of certain mucus-penetrating particles including a polymeric carrier, in certain embodiments such particles may be preferred. For example, it may be preferable to use polymer carriers for controlled release purposes and/or for encapsulating certain pharmaceutical agents that are difficult to formulate into particles. As such, in some embodiments described herein, particles that include a polymer carrier are described.

In some embodiments, the pharmaceutical compositions of the invention involve the use of poly(vinyl alcohols) (PVAs) to aid particle transport in mucus. The pharmaceutical compositions may involve making MPPs or MPCs by, for example, an emulsification process in the presence of specific PVAs. In certain embodiments, the pharmaceutical compositions and methods involve making MPPs or MPCs from pre-fabricated particles by non-covalent coating with specific PVAs. In some embodiments, the pharmaceutical compositions and methods involve making MPPs in the presence of specific PVAs without any polymeric carriers or with minimal use of polymeric carriers. It should be appreciated, however, that in other embodiments, polymeric carriers can be used.

PVA is a water-soluble non-ionic synthetic polymer. Due to its surface active properties, PVA is widely used in the food and drug industries as a stabilizing agent for emulsions and, in particular, to enable encapsulation of a wide variety of compounds by emulsification techniques. PVA has the "generally recognized as safe" (GRAS) status with the Food and Drug Administration (FDA), and has been used in auricular, intramuscular, intraocular, intravitreal, iontophoretic, ophthalmic, oral, topical, and transdermal drug products and/or drug delivery systems.

In certain previous studies, many have described PVA as a mucoadhesive polymer, suggesting that incorporating PVA in the particle formulation process leads to particles that are strongly mucoadhesive. Surprisingly, and contrary to the established opinion that PVA is a mucoadhesive polymer, it is discovered that pharmaceutical compositions of the invention utilizing specific PVA grades in fact aid particle transport in mucus and are not mucoadhesive in certain applications of the invention. Specifically, MPPs can be prepared by tailoring the degree of hydrolysis and/or molecular weight of the PVA, which was previously unknown. This discovery significantly broadens the arsenal of techniques and ingredients applicable for manufacturing MPPs.

In other embodiments, the pharmaceutical compositions of the invention and the methods of making the particles and pharmaceutical compositions of the invention involve PVAs in conjunction with other polymers or do not involve PVAs at all. For example, PEG and/or PLURONICS® may be included in the pharmaceutical compositions of the invention and methods of making the particles and pharmaceutical compositions of the invention, in addition to or in replace of PVAs. Other polymers, such as those described herein, may also be used.

Core of the Particles

A particle of the invention includes a core. As described herein in reference to FIG. 1, particle 10 may include a core 16. The core of the inventive particles may be formed of any suitable material, such as an organic material, inorganic material, polymer, lipid, protein, or combinations thereof. In some embodiments, the core is a solid. The solid may be, for example, a crystalline, semi-crystalline, or amorphous solid, such as a crystalline, semi-crystalline, or amorphous solid pharmaceutical agent (e.g., a compound of the invention), or a salt thereof. In certain embodiments, the core is a gel or liquid (e.g., an oil-in-water or water-in-oil emulsion).

One or more pharmaceutical agents may be present in the core. The pharmaceutical agent may be present in the core in any suitable amount, e.g., at least about 80 wt % and less than about 100 wt % of the core). Other ranges are also possible.

Particles that are formed by encapsulating pharmaceutical agents into polymeric carriers typically have a low loading of the pharmaceutical agent (e.g., less than about 50 wt % of the core of the particles). In contrast, in certain embodiments, the loading of the pharmaceutical agent in the core of the inventive particles is high (e.g., at least about 50 wt % of the core). A high drug loading is an advantage for drug delivery, since a high drug loading often means that fewer numbers of particles may be needed to achieve a desired effect. As described herein, in other embodiments in which a relatively high amount of a polymer or other material forms the core, the loading of the pharmaceutical agent in the core is low (e.g., less than about 50 wt % of the core).

The core may comprise a solid material having various aqueous solubilities and/or various solubilities in a coating solution (a solution in which the solid material is being coated with a surface-altering agent). For example, the solid material may have an aqueous solubility (or a solubility in a coating solution) of at least about 10 pg/mL and less than about or equal to about 1 mg/mL). Other ranges are also possible. The solid material may have these or other ranges of aqueous solubilities at any point throughout the pH range (e.g., from pH 1 to pH 14).

In some embodiments, the core may be formed of a material within one of the ranges of solubilities classified by the U.S. Pharmacopeia Convention: e.g., very soluble: >1,000 mg/mL; freely soluble: 100-1,000 mg/mL; soluble: 33-100 mg/mL; sparingly soluble: 10-33 mg/mL; slightly soluble: 1-10 mg/mL; very slightly soluble: 0.1-1 mg/mL; and practically insoluble: <0.1 mg/mL.

In certain embodiments, the core of the particles of the invention is hydrophobic. In certain embodiments, the core is substantially hydrophobic. In certain embodiments, the core is hydrophilic. In certain embodiments, the core is substantially hydrophilic.

The hydrophobicity and hydrophilicity of a material (e.g., a material used to form the core of the particles of the invention) can be determined by measuring the contact angle of a water droplet on a planar surface of the material, e.g., using an instrument such as a contact angle goniometer and a packed powder of the material. In some embodiments, the material used to form the core has a contact angle of at least about 20 degrees, at least about 30 degrees, at least about 40 degrees, at least about 50 degrees, at least about 60 degrees, at least about 70 degrees, at least about 80 degrees, at least about 90 degrees, at least about 100 degrees, at least about 110 degrees, at least about 120 degrees, or at least about 130 degrees. In some embodiments, the material used to form the core has a contact angle of less than about 160 degrees, less than about 150 degrees, less than about 140 degrees, less than about 130 degrees, less than about 120 degrees, less than about 110 degrees, less than about 100 degrees, less than about 90 degrees, less than about 80 degrees, or less than about 70 degrees. Combinations of the above-referenced ranges are also possible (e.g., a contact angle of at least about 30 degrees and less than about 120 degrees). Other ranges are also possible.

Contact angle measurements can be made using a variety of techniques, such as a static contact angle measurement between a pellet of the starting material which will be used to form the core and a bead of water. The material used to form the core is a fine powder. In order to form a surface on which to make measurements, the powder is packed using a 7 mm pellet die set from International Crystal Labs. The material is added to the die and pressure is applied to pack the powder into a pellet. No pellet press or high pressure is used. The pellet is then suspended for testing so that the top and bottom of the pellet (defined as the surface water is added to and the opposite parallel surface respectively) are not in contact with any surface. This is done by not fully removing the pellet from the collar of the die set. The pellet therefore touches the collar on the sides and makes no contact on the top or bottom. For contact angle measurements, water is added to the surface of the pellet until a bead of water with a steady contact angle over 30 seconds is obtained. The water is added into the bead of water by submerging or contacting the tip of the pipette or syringe used for addition to the bead of water. Once a stable bead of water is obtained, an image is taken and the contact angle is measured using standard practices.

In some embodiments, the core includes one or more organic materials, such as a synthetic polymer and/or natural polymer. Examples of synthetic polymers include non-degradable polymers (e.g., polymethacrylate) and degradable polymers (e.g., polylactic acid and polyglycolic acid), and copolymers thereof. Examples of natural polymers include hyaluronic acid, chitosan, and collagen. Other examples of polymers that may be suitable for portions of the core include those suitable for forming coatings on particles, as described herein. In some cases, the one or more polymers present in the core may be used to encapsulate or adsorb one or more pharmaceutical agents.

When a polymer is present in the core, the polymer may be present in the core in any suitable amount, e.g., less than about 100 wt %, less than about 80 wt %, less than about 60 wt %, less than about 50 wt %, less than about 40 wt %, less than about 30 wt %, less than about 20 wt %, less than about 10 wt %, less than about 5 wt %, or less than about 1 wt %. In some cases, the polymer may be present in an amount of at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt % in the core. Combinations of the above-referenced ranges are also possible (e.g., present in an amount of at least about 1 wt % and less than about 20 wt %). Other ranges are also possible. In some embodiments, the core is substantially free of a polymeric component.

In certain embodiments, a core includes a pharmaceutical agent comprising a lipid and/or a protein.

The core may have any suitable shape and/or size. For instance, the core may be substantially spherical, non-spherical, oval, rod-shaped, pyramidal, cube-like, disk-shaped, wire-like, or irregularly shaped. The core may have a largest or smallest cross-sectional dimension of, for example, less than about 10 μm, less than about 3 μm, less than about 1 μm, less than about 500 nm, less than about 400 nm, less than 300 nm, less than about 200 nm, less than about 100 nm, less than about 30 nm, or less than about 10 nm. In some cases, the core may have a largest or smallest cross-sectional dimension of, for example, at least about 10 nm, at least about 30 nm, at least about 100 nm, at least about 200 nm, at least about 300 nm, at least about 400 nm, at least about 500 nm, at least about 1 μm, or at least about 3 μm. Combinations of the above-referenced ranges are also possible (e.g., a largest or smallest cross-sectional dimension of at least about 30 nm and less than about 500 nm). Other ranges are also possible. In some embodiments, the sizes of the cores formed by a process described herein have a Gaussian-type distribution. Unless indicated otherwise, the measurements of the particle sizes or core sizes refer to the smallest cross-sectional dimension.

Techniques to determine sizes (e.g., smallest or largest cross-sectional dimensions) of particles are known in the art. Examples of suitable techniques include dynamic light scattering (DLS), transmission electron microscopy, scanning electron microscopy, electroresistance counting and laser diffraction. Although many methods for determining sizes of particles are known, the sizes described herein (e.g., average particle sizes and thicknesses) refer to ones measured by DLS.

Coating of the Particles

A particle of the invention may include a coating. An inventive particle including a coating may be referred to as a coated particle of the invention. An inventive particle not including a coating may be referred to as an uncoated particle of the invention. As shown in the embodiment illustrated in FIG. 1, core 16 may be surrounded by coating 20 comprising one or more surface-altering agents. In some embodiments, the coating is formed of one or more surface-altering agents or other molecules disposed on the surface of the core. The particular chemical makeup and/or components of the coating and surface-altering agent(s) can be chosen so as to impart certain functionality to the particles, such as enhanced transport through mucosal barriers.

It should be understood that a coating which surrounds a core need not completely surround the core, although such embodiments may be possible. For example, the coating may surround at least about 10%, at least about 30%, at least about 50%, at least about 70%, at least about 90%, or at least about 99% of the surface area of a core. In some cases, the coating substantially surrounds a core. In other cases, the coating completely surrounds a core. In other embodiments, a coating surrounds less than about 100%, less than about 90%, less than about 70%, or less than about 50% of the surface area of a core. Combinations of the above-referenced ranges are also possible (e.g., surrounding at least 70% and less than 100% of the surface area of a core).

The material of the coating may be distributed evenly across a surface of the core in some cases, and unevenly in other cases. For example, the coating may include portions (e.g., holes) that do not include any material. If desired, the coating may be designed to allow penetration and/or transport of certain molecules and components into or out of the coating, but may prevent penetration and/or transport of other molecules and components into or out of the coating. The ability of certain molecules to penetrate and/or be transported into and/or across a coating may depend on, for example, the packing density of the surface-altering agents forming the coating and the chemical and physical properties of the components forming the coating. As described herein, the coating may include one layer of material (i.e., a monolayer) or multilayers of materials. A single type or multiple types of surface-altering agent may be present.

The coating of particles of the invention can have any suitable thickness. For example, the coating may have an average thickness of at least about 1 nm, at least about 3 nm, at least about 10 nm, at least about 30 nm, at least about 100 nm, at least about 300 nm, at least about 400 nm, at least about 1 µm, or at least about 3 µm. In some cases, the average thickness of the coating is less than about 3 µm, less than about 1 µm, less than about 300 nm, less than about 100 nm, less than about 30 nm, less than about 10 nm, or less than about 3 nm. Combinations of the above-referenced ranges are also possible (e.g., an average thickness of at least about 1 nm and less than about 100 nm). Other ranges are also possible. For particles having multiple coatings, each coating may have one of the thicknesses described herein.

The pharmaceutical compositions of the invention may allow for the coating of the particles of the invention with hydrophilic surface-altering moieties without requiring covalent association of the surface-altering moieties to the surface of the core. In some embodiments, the core having a hydrophobic surface is coated with a polymer described herein, thereby causing a plurality of surface-altering moieties to be on the surface of the core without substantially altering the characteristics of the core itself. For example, the surface altering agent may be present on (e.g., adsorbed to) the outer surface of the core. In other embodiments, a surface-altering agent is covalently linked to the core.

In certain embodiments in which the surface-altering agent is adsorbed onto a surface of the core, the surface-altering agent may be in equilibrium with other molecules of the surface-altering agent in solution, optionally with other components (e.g., in a pharmaceutical composition). In some cases, the adsorbed surface-altering agent may be present on the surface of the core at a density described herein. The density may be an average density as the surface altering agent is in equilibrium with other components in solution.

The coating and/or surface-altering agent of the particles of the invention may comprise any suitable material, such as a hydrophobic material, a hydrophilic material, and/or an amphiphilic material. In some embodiments, the coating includes a polymer. In certain embodiments, the polymer is a synthetic polymer (i.e., a polymer not produced in nature). In other embodiments, the polymer is a natural polymer (e.g., a protein, polysaccharide, or rubber). In certain embodiments, the polymer is a surface active polymer. In certain embodiments, the polymer is a non-ionic polymer. In certain embodiments, the polymer is a linear synthetic non-ionic polymer. In certain embodiments, the polymer is a non-ionic block copolymer. The polymer may be a copolymer. In certain embodiments, one repeat unit of the copolymer is relatively hydrophobic and another repeat unit of the copolymer is relatively hydrophilic. The copolymer may be, for example, a diblock, triblock, alternating, or random copolymer. The polymer may be charged or uncharged.

In some embodiments, the coating of the particles of the invention comprises a synthetic polymer having pendant hydroxyl groups on the backbone of the polymer. Examples of the synthetic polymer are as described herein. Without wishing to be bound by theory, a particle including a coating comprising a synthetic polymer having pendant hydroxyl groups on the backbone of the polymer may have reduced mucoadhesion as compared to a control particle due to, at least in part, the display of a plurality of hydroxyl groups on the particle surface. One possible mechanism for the reduced mucoadhesion is that the hydroxyl groups alter the microenvironment of the particle, for example, by ordering water and other molecules in the particle/mucus environment. An additional or alternative possible mechanism is that the hydroxyl groups shield the adhesive domains of the mucin fibers, thereby reducing particle adhesion and speeding up particle transport.

Moreover, the ability of a particle coated with a synthetic polymer having pendant hydroxyl groups on the backbone of the polymer to be mucus penetrating may also depend, at least in part, on the degree of hydrolysis of the polymer. In some embodiments, the hydrophobic portions of the polymer (e.g., portions of the polymer that are not hydrolyzed) allow the polymer to be adhered to the surface of the core (e.g., in the case that the surface of the core is hydrophobic), thus allowing for a strong association between the core and polymer. Surprisingly, it has been found that, in some embodiments involving PVA as the surface-altering agent, too high of a degree of hydrolysis does not allow for sufficient adhesion between the PVA and the core (e.g., in the case of the core being hydrophobic), and thus, the particles coated with such a polymer generally do not exhibit sufficient reduced mucoadhesion. In some embodiments, too low of a degree of hydrolysis does not enhance particle transport in mucus, perhaps due to the lower amounts of hydroxyl groups available for altering the microenvironment of the particle and/or shielding the adhesive domains of the mucin fibers.

A synthetic polymer having pendant hydroxyl groups on the backbone of the polymer may have any suitable degree of hydrolysis (and, therefore, varying amounts of hydroxyl groups). The appropriate level of hydrolysis may depend on additional factors, such as the molecular weight of the polymer, the pharmaceutical composition of the core, and the hydrophobicity of the core. In some embodiments, the synthetic polymer is at least about 30% hydrolyzed, at least about 40% hydrolyzed, at least about 50% hydrolyzed, at least about 60% hydrolyzed, at least about 70% hydrolyzed, at least about 80% hydrolyzed, at least about 90% hydrolyzed, or at least about 95% hydrolyzed. In some embodiments, the synthetic polymer is less than about 100% hydrolyzed, less than about 95% hydrolyzed, less than about 90% hydrolyzed, less than about 80% hydrolyzed, less than about 70% hydrolyzed, or less than about 60% hydrolyzed. Combinations of the above-mentioned ranges are also possible (e.g., a synthetic polymer that is at least about 80% and less than about 95% hydrolyzed). Other ranges are also possible.

The molecular weight of the synthetic polymer described herein (e.g., one having pendant hydroxyl groups on the backbone of the polymer) may be selected so as to reduce the mucoadhesion of a core and to ensure sufficient association of the polymer with the core. In certain embodiments, the molecular weight of the synthetic polymer is at least about 1 kDa, at least about 2 kDa, at least about 5 kDa, at least about 8 kDa, at least about 9 kDa, at least about 10 kDa, at least about 12 kDa, at least about 15 kDa at least about 20 kDa, at least about 25 kDa, at least about 30 kDa, at least about 40 kDa, at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the molecular weight of the synthetic polymer is less than about 1000 kDa, less than about 500 kDa, less than about 200 kDa, less than about, less than about 150 kDa, less than about 130 kDa, less than about 120 kDa, less than about 100 kDa, less than about 85 kDa, less than about 70 kDa, less than about 65 kDa, less than about 60 kDa, less than about 50 kDa, or less than about 40 kDa, less than about 30 kDa, less than about 20 kDa, less than about 15 kDa, or less than about 10 kDa. Combinations of the above-mentioned ranges are also possible (e.g., a molecular weight of at least about 10 kDa and less than about 30 kDa). The above-mentioned molecular weight ranges can also be combined with the above-mentioned hydrolysis ranges to form suitable polymers.

In some embodiments, the synthetic polymer described herein is or comprises PVA. In some embodiments, the synthetic polymer described herein is or comprises partially hydrolyzed PVA. Partially hydrolyzed PVA includes two types of repeating units: vinyl alcohol units and residual vinyl acetate units. The vinyl alcohol units are relatively hydrophilic, and the vinyl acetate units are relatively hydrophobic. In some instances, the sequence distribution of vinyl alcohol units and vinyl acetate units is blocky. For example, a series of vinyl alcohol units may be followed by a series of vinyl acetate units, and followed by more vinyl alcohol units to form a polymer having a mixed block-copolymer type arrangement, with units distributed in a blocky manner. In certain embodiments, the repeat units form a copolymer, e.g., a diblock, triblock, alternating, or random copolymer. Polymers other than PVA may also have these configurations of hydrophilic units and hydrophobic units.

In some embodiments, the hydrophilic units of the synthetic polymer described herein are substantially present at the outer surface of the particles of the invention. For example, the hydrophilic units may form a majority of the outer surface of the coating and may help stabilize the particles in an aqueous solution containing the particles. The hydrophobic units may be substantially present in the interior of the coating and/or at the surface of the core, e.g., to facilitate attachment of the coating to the core.

The molar fraction of the relatively hydrophilic units and the relatively hydrophobic units of the synthetic polymer described herein may be selected so as to reduce the mucoadhesion of a core and to ensure sufficient association of the polymer with the core, respectively. As described herein, the molar fraction of the hydrophobic units of the polymer may be chosen such that adequate association of the polymer with the core occurs, thereby increasing the likelihood that the polymer remains adhered to the core. The molar fraction of the relatively hydrophilic units to the relatively hydrophobic units of the synthetic polymer may be, for example, at least 0.5:1, at least 1:1, at least 2:1, at least 3:1, at least 5:1, at least 10:1, at least 20:1, at least 30:1, at least 50:1, or at least 100:1. In some embodiments, the molar fraction of the relatively hydrophilic units to the relatively hydrophobic units of the synthetic polymer may be, for example, less than 100:1, less than 50:1, less than 30:1, less than 20:1, less than 10:1, less than 5:1, less than 3:1, less than 2:1, or less than 1:1. Combinations of the above-referenced ranges are also possible (e.g., a ratio of at least 1:1 and less than 50:1). Other ranges are also possible.

The molecular weight of the PVA polymer may also be tailored to increase the effectiveness of the polymer to render particles mucus penetrating. Examples of PVA polymers having various molecular weights and degree of hydrolysis are shown in Table 1.

TABLE 1

Molecular weight (MW) and degree of hydrolysis of various poly (vinyl alcohols) (PVAs).[a]

| PVA | MW (kDa) | Hydrolysis degree (%) |
| --- | --- | --- |
| 2K75 | 2 | 75-79 |
| 9K80 | 9-10 | 80 |
| 13K87 | 13-23 | 87-89 |
| 13K98 | 13-23 | 98 |
| 31K87 | 31-50 | 87-89 |
| 31K98 | 31-50 | 98-99 |
| 57K86 | 57-60 | 86-89 |
| 85K87 | 85-124 | 87-89 |
| 85K99 | 85-124 | 99+ |
| 95K95 | 95 | 95 |
| 105K80 | 104 | 80 |
| 130K87 | 130 | 87-89 |

[a]The values of the molecular weight and hydrolysis degree of the PVAs were provided by the manufacturers of the PVAs.

In certain embodiments, the synthetic polymer is represented by the formula:

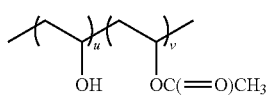

wherein:
u is an integer between 0 and 22730, inclusive; and
v is an integer between 0 and 11630, inclusive.

In some embodiments, the particles of the invention include a coating comprising a block copolymer having a relatively hydrophilic block and a relatively hydrophobic block. In some cases, the hydrophilic blocks may be substantially present at the outer surface of the particle. For example, the hydrophilic blocks may form a majority of the outer surface of the coating and may help stabilize the particle in an aqueous solution containing the particle. The hydrophobic block may be substantially present in the interior of the coating and/or at the surface of the core, e.g., to facilitate attachment of the coating to the core. In some embodiments, the coating comprises a surface-altering agent including a triblock copolymer, wherein the triblock copolymer comprises a (hydrophilic block)-(hydrophobic block)-(hydrophilic block) configuration. Diblock copolymers having a (hydrophilic block)-(hydrophobic block) configuration are also possible. Combinations of block copolymers with other polymers suitable for use as coatings are also possible. Non-linear block configurations are also possible such as in comb, brush, or star copolymers. In some embodiments, the relatively hydrophilic block includes a synthetic polymer having pendant hydroxyl groups on the backbone of the polymer (e.g., PVA).

The molecular weight of the hydrophilic blocks and the hydrophobic blocks of the block copolymers described herein may be selected so as to reduce the mucoadhesion of a core and to ensure sufficient association of the block copolymer with the core, respectively. The molecular weight of the hydrophobic block of the block copolymer may be chosen such that adequate association of the block copolymer with the core occurs, thereby increasing the likelihood that the block copolymer remains adhered to the core.

In certain embodiments, the molecular weight of each block of or combined blocks of the (one or more) relatively hydrophobic blocks of a block copolymer is at least about 0.5 kDa, at least about 1 kDa, at least about 1.8 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the molecular weight of each block of or combined blocks of the (one or more) relatively hydrophobic blocks is less than about 1000 kDa, less than about 500 kDa, less than about 200 kDa, less than about 150 kDa, less than about 140 kDa, less than about 130 kDa, less than about 120 kDa, less than about 110 kDa, less than about 100 kDa, less than about 90 kDa, less than about 80 kDa, less than about 50 kDa, less than about 20 kDa, less than about 15 kDa, less than about 13 kDa, less than about 12 kDa, less than about 10 kDa, less than about 8 kDa, or less than about 6 kDa. Combinations of the above-mentioned ranges are also possible (e.g., at least about 3 kDa and less than about 15 kDa). Other ranges are also possible.

In some embodiments, the combined relatively hydrophilic blocks (e.g., two hydrophilic blocks of a triblock copolymer) of a block copolymer (e.g., a triblock copolymer) constitute at least about 10 wt %, at least about 20 wt %, at least about 30 wt %, at least about 40 wt %, at least about 50 wt %, at least about 60 wt %, or at least about 70 wt % of the block copolymer. In some embodiments, the combined (one or more) relatively hydrophilic blocks of a block copolymer constitute less than about 90 wt %, less than about 80 wt %, less than about 60 wt %, less than about 50 wt %, or less than about 40 wt % of the block copolymer. Combinations of the above-referenced ranges are also possible (e.g., at least about 30 wt % and less than about 70 wt %). Other ranges are also possible.

In some embodiments, the molecular weight of each block of or combined blocks of the (one or more) relatively hydrophilic blocks of the block copolymer may be at least about 0.5 kDa, at least about 1 kDa, at least about 1.8 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In certain embodiments, the molecular weight of each block of or combined blocks of the (one or more) relatively hydrophilic blocks is less than about 1000 kDa, less than about 500 kDa, less than about 200 kDa, less than about 150 kDa, less than about 140 kDa, less than about 130 kDa, less than about 120 kDa, less than about 110 kDa, less than about 100 kDa, less than about 90 kDa, less than about 80 kDa, less than about 50 kDa, less than about 20 kDa, less than about 15 kDa, less than about 13 kDa, less than about 12 kDa, less than about 10 kDa, less than about 8 kDa, less than about 6 kDa, less than about 5 kDa, less than about 3 kDa, less than about 2 kDa, or less than about 1 kDa. Combinations of the above-mentioned ranges are also possible (e.g., at least about 0.5 kDa and less than about 3 kDa). Other ranges are also possible. In embodiments in which two hydrophilic blocks flank a hydrophobic block, the molecular weights of the two hydrophilic blocks may be substantially the same or different.

In certain embodiments, the polymer of the surface-altering agent includes a polyether portion. In certain embodiments, the polymer includes a polyalkylether portion. In certain embodiments, the polymer includes polyethylene glycol (PEG) tails. In certain embodiments, the polymer includes a polypropylene glycol as the central portion. In certain embodiments, the polymer includes polybutylene glycol as the central portion. In certain embodiments, the polymer includes polypentylene glycol as the central portion. In certain embodiments, the polymer includes polyhexylene glycol as the central portion. In certain embodiments, the polymer is a triblock copolymer of one of the polymers described herein. In some embodiments, a diblock or triblock copolymer comprises a synthetic polymer having pendant hydroxyl groups on the backbone of the polymer (e.g., PVA) as one or more of the blocks (with varying degrees of hydrolysis and varying molecular weights as described herein). The synthetic polymer blocks may form the central portion or end portions of the block copolymer.

In certain embodiments, the polymer is a triblock copolymer of a polyalkyl ether (e.g., polyethylene glycol, polypropylene glycol) and another polymer (e.g., a synthetic polymer having pendant hydroxyl groups on the backbone of the polymer (e.g., PVA). In certain embodiments, the polymer is a triblock copolymer of a polyalkyl ether and another polyalkyl ether. In certain embodiments, the polymer is a triblock copolymer of polyethylene glycol and another polyalkyl ether. In certain embodiments, the polymer is a triblock copolymer of polypropylene glycol and another polyalkyl ether. In certain embodiments, the polymer is a triblock copolymer with at least one unit of polyalkyl ether. In certain embodiments, the polymer is a triblock copolymer of two different polyalkyl ethers. In certain embodiments, the polymer is a triblock copolymer including a polyethylene glycol unit. In certain embodiments, the polymer is a triblock copolymer including a polypropylene glycol unit. In certain embodiments, the polymer is a triblock copolymer of a more hydrophobic unit flanked by two more hydrophilic units. In certain embodiments, the hydrophilic units are the same type of polymer. In some embodiments, the hydrophilic units include a synthetic polymer having pendant hydroxyl groups on the backbone of the polymer (e.g., PVA). In certain embodiments, the polymer includes a polypropylene glycol unit flanked by two more hydrophilic units. In certain embodiments, the polymer includes two polyethylene glycol units flanking a more hydrophobic unit. In certain embodiments, the polymer is a triblock copolymer with a polypropylene glycol unit flanked by two polyethylene glycol units. The molecular weights of the two blocks flanking the central block may be substantially the same or different.

In certain embodiments, the polymer is of the formula:

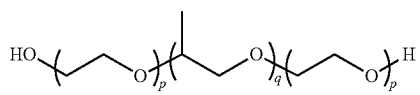

wherein each instance of p is independently an integer between 2 and 1140, inclusive; and q is an integer between 2 and 1730, inclusive. In certain embodiments, each instance of p is independently an integer between 10 and 170, inclusive. In certain embodiments, q is an integer between 5 and 70 inclusive. In certain embodiments, each instance of p is independently at least 2 times of q, 3 times of q, or 4 times of q.

In certain embodiments, the surface-altering agent comprises a (poly(ethylene glycol))-(poly(propylene oxide))-(poly(ethylene glycol)) triblock copolymer (PEG-PPO-PEG triblock copolymer), present in the coating alone or in combination with another polymer such as a synthetic polymer having pendant hydroxyl groups on the backbone of the polymer (e.g., PVA). The molecular weights of the PEG and PPO segments of the PEG-PPO-PEG triblock copolymer may be selected so as to reduce the mucoadhesion of the particles, as described herein. Without wishing to be bound by any theory, the particles of the invention having a coating comprising a PEG-PPO-PEG triblock copolymer may have reduced mucoadhesion as compared to control particles due to, at least in part, the PEG segments on the surface of the particles of the invention. The PPO segment may be adhered to the surface of the core (e.g., in the case of the surface of the core being hydrophobic), thus allowing for a strong association between the core and the triblock copolymer. In some embodiments, the PEG-PPO-PEG triblock copolymer is associated with the core through non-covalent interactions. For purposes of comparison, the control particle may be, for example, a carboxylate-modified polystyrene particle of similar size as the particle of the invention.

In certain embodiments, the surface-altering agent includes a polymer comprising a poloxamer, having the trade name PLURONIC®. PLURONIC® polymers that may be useful in the embodiments described herein include, but are not limited to, F127, F38, F108, F68, F77, F87, F88, F98, L101, L121, L31, L35, L43, L44, L61, L62, L64, L81, L92, N3, P103, P104, P105, P123, P65, P84, and P85. Examples of molecular weights of certain PLURONIC® polymers are shown in Table 2.

TABLE 2

Molecular weight (MW) of PLURONIC® polymers

| PLURONIC | Average MW (Da) | MW of the PPO portion (Da) | PEG wt% | MW of the PEG portion (Da) |
|---|---|---|---|---|
| F127 | 12000 | 3600 | 70 | 8400 |
| L44 | 2000 | 1200 | 40 | 800 |
| L81 | 2667 | 2400 | 10 | 267 |
| L101 | 3333 | 3000 | 10 | 333 |
| P65 | 3600 | 1800 | 50 | 1800 |
| L121 | 4000 | 3600 | 10 | 400 |
| P103 | 4286 | 3000 | 30 | 1286 |
| F38 | 4500 | 900 | 80 | 3600 |
| P123 | 5143 | 3600 | 30 | 1543 |
| P105 | 6000 | 3000 | 50 | 3000 |
| F87 | 8000 | 2400 | 70 | 5600 |
| F68 | 9000 | 1800 | 80 | 7200 |
| P123 | 5750 | 4030 | 30 | 1730 |

Although other ranges may be possible, in some embodiments, the hydrophobic block of the PEG-PPO-PEG triblock copolymer has one of the molecular weights described above (e.g., at least about 3 kDa and less than about 15 kDa), and the combined hydrophilic blocks have a weight percentage with respect to the polymer in one of the ranges described above (e.g., at least about 15 wt %, at least about 20 wt %, at least about 25 wt %, or at least about 30 wt %, and less than about 80 wt %). Certain PLURONIC® polymers that fall within these criteria include, for example, F127, F108, P105, and P103. In certain embodiments, the particles of the invention including PLURONIC® polymers that fall within these criteria are more mucus penetrating than particles including PLURONIC® polymers that did not fall within these criteria. Materials that do not render the particles mucus penetrating also include certain polymers such as polyvinylpyrrolidones (PVP/KOLLIDON), polyvinyl alcohol-polyethylene glycol graft-copolymer (KOLLICOAT IR), and hydroxypropyl methylcellulose (METHOCEL); oligomers such as TWEEN 20, TWEEN 80, SOLUTOL HS 15, TRITON X100, tyloxapol, and CREMOPHOR RH 40; and small molecules such as SPAN 20, SPAN 80, octyl glucoside, cetytrimethylammonium bromide (CTAB), and sodium dodecyl sulfate (SDS).

Although much of the description herein may involve coatings comprising a (hydrophilic block)-(hydrophobic block)-(hydrophilic block) configuration (e.g., a PEG-PPO-PEG triblock copolymer) or coatings comprising a synthetic polymer having pendant hydroxyl groups, it should be appreciated that the coatings are not limited to these configurations and materials and that other configurations and materials are possible.

Furthermore, although many of the embodiments described herein involve a single coating, in other embodiments, a particle may include more than one coating (e.g., at least two, three, four, five, or more coatings), and each coating need not be formed of or comprise a mucus penetrating material. In some embodiments, an intermediate coating (i.e., a coating between the core surface and an outer coating) may include a polymer that facilitates attachment of an outer coating to the core surface. In some embodiments, an outer coating of a particle includes a polymer comprising a material that facilitates the transport of the particle through mucus.

The coating (e.g., an inner coating, intermediate coating, and/or outer coating) of the particles of the invention may include any suitable polymer. In some embodiments, the polymer of the coating is biocompatible and/or biodegradable. In some embodiments, the polymer of the coating comprises more than one type of polymer (e.g., at least two, three, four, five, or more types of polymers). In some embodiments, the polymer of the coating is a random copolymer or a block copolymer (e.g., a diblock or triblock copolymer) as described herein.

Non-limiting examples of suitable polymers of the coating may include polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate.

The molecular weight of the polymer of the coating may vary. In some embodiments, the molecular weight of the polymer of the coating is at least about 0.5 kDa, at least about 1 kDa, at least about 1.8 kDa, at least about 2 kDa, at least about 3 kDa, at least about 4 kDa, at least about 5 kDa, at least about 6 kDa, at least about 8 kDa, at least about 10 kDa, at least about 12 kDa, at least about 15 kDa, at least about 20 kDa, at least about 30 kDa, at least about 40 kDa, or at least about 50 kDa. In some embodiments, the molecular weight of the polymer of the coating is less than about 50 kDa, less than about 40 kDa, less than about 30 kDa, less than about 20 kDa, less than about 12 kDa, less than about 10 kDa, less than about 8 kDa, less than about 6 kDa, less than about 5 kDa, or less than about 4 kDa. Combinations of the above-referenced ranges are possible (e.g., a molecular weight of at least about 2 kDa and less than about 15 kDa). Other ranges are also possible. The molecular weight of the polymer of the coating may be determined using any known technique such as light-scattering and gel permeation chromatography. Other methods are known in the art.

In certain embodiments, the molecular weight of the hydrophobic block of the triblock copolymer of the (hydrophilic block)-(hydrophobic block)-(hydrophilic block) configuration is at least about 2 kDa, and the two hydrophilic blocks constitute at least about 15 wt % of the triblock copolymer.

In certain embodiments, the polymer of the coating is biocompatible. In certain embodiments, the polymer of the coating is biodegradable. All biocompatible polymers and biodegrade polymers are contemplated to be within the scope of the invention. In certain embodiments, a polymer degrades in vivo within a period that is acceptable for the desired application. For example, in an in vivo therapy, the polymer degrades in a period less than about five years, about one year, about six months, about three months, about one month, about two weeks, about one week, about three days, about one day, about six hours, or about one hour upon exposure to a physiological environment with a pH between about 6 and about 8 having a temperature of between about 25 and about 37° C. In some embodiments, the polymer of the coating degrades in a period of between about one hour and several weeks, depending on the desired application.

Although the particles of the invention, and the coating thereof, may each include polymers, in some embodiments, the particles of the invention comprise a hydrophobic material that is not a polymer or pharmaceutical agent. Non-limiting examples of non-polymeric hydrophobic materials include, for example, metals, waxes, and organic materials (e.g., organic silanes and perfluorinated or fluorinated organic materials).

Particles with Reduced Mucoadhesion

Particles of the invention may have reduced mucoadhesiveness. A material in need of increased diffusivity through mucus may be hydrophobic, may include many hydrogen bond donors or acceptors, and/or may be highly charged. In some cases, the material may include a crystalline or amorphous solid material. The material, which may serve as a core, may be coated with a suitable polymer described herein, thereby forming a particle with a plurality of surface-altering moieties on the surface, resulting in reduced mucoadhesion. Particles of the invention as having reduced mucoadhesion may alternatively be characterized as having increased transport through mucus, being mobile in mucus, or mucus-penetrating (i.e., mucus-penetrating particles), meaning that the particles are transported through mucus faster than a negative control particle. The negative control particle may be a particle that is known to be mucoadhesive, e.g., an unmodified particle or core that is not coated with a coating described herein, such as a 200 nm carboxylated polystyrene particle.

Particles of the invention may be adapted for delivery (e.g., inhalational delivery) to mucus or a mucosal surface of a subject. The particles with surface-altering moieties may be delivered to the mucosal surface of a subject, may pass through the mucosal barrier in the subject, and/or prolonged retention and/or increased uniform distribution of the particles at mucosal surfaces, e.g., due to reduced mucoadhesion.

Furthermore, in some embodiments, the particles of the invention having reduced mucoadhesion facilitate better distribution of the particles at the surface of a tissue of a subject and/or have a prolonged presence at the surface of the tissue, compared to particles that are more mucoadhesive. For example, a luminal space such as the gastrointestinal tract is surrounded by a mucus-coated surface. Mucoadhesive particles delivered to such a space are typically removed from the luminal space and from the mucus-coated surface by the subject's natural clearance mechanisms. The particles of the invention with reduced mucoadhesion may remain in the luminal space for relatively longer periods compared to the mucoadhesive particles. This prolonged presence may prevent or reduce clearance of the particles and/or may allow for better distribution of the particles on the surface of the tissue. The prolonged presence may also affect the particle transport through the luminal space, e.g., the particles may distribute into the mucus layer and may reach the underlying epithelium.

In certain embodiments, the core of the particles of the invention coated with the polymer of the coating may pass through mucus or a mucosal barrier in a subject, exhibit prolonged retention, and/or increase uniform distribution of the particles at mucosal surfaces, e.g., such substances are cleared more slowly (e.g., at least about 2 times, about 5 times, about 10 times, or even at least about 20 times more slowly) from a subject's body as compared to a negative control particle of the invention.

The mobility of the particles of the invention in mucus may be characterized in, e.g., the relative velocity and/or diffusivity of the particles. In certain embodiments, the particles of the invention have certain relative velocity, $\langle V_{mean} \rangle_{rel}$, which is defined as follows:

$$\langle V_{mean} \rangle_{rel} = \frac{\langle V_{mean} \rangle_{Sample} - \langle V_{mean} \rangle_{Negative\ control}}{\langle V_{mean} \rangle_{Positive\ control} - \langle V_{mean} \rangle_{Negative\ control}} \quad \text{(Equation 1)}$$

wherein:

$\langle V_{mean} \rangle$ is the ensemble average trajectory-mean velocity;

$V_{mean}$ is the velocity of an individual particle averaged over its trajectory;

the sample is the particle of interest;

the negative control is a 200 nm carboxylated polystyrene particle; and the positive control is a 200 nm polystyrene particle densely PEGylated with 2-5 kDa PEG.

The relative velocity can be measured by a multiple particle tracking technique. For instance, a fluorescent microscope equipped with a CCD camera can be used to capture 15 s movies at a temporal resolution of 66.7 ms (15 frames/s) under 100× magnification from several areas within each sample for each type of particles: sample, negative control, and positive control. The sample, negative control, and positive control may be fluorescent particles to observe tracking. Alternatively non-fluorescent particles may be coated with a fluorescent molecule, a fluorescently tagged surface agent, or a fluorescently tagged polymer. An advanced image processing software (e.g., IMAGE PRO OR METAMORPH) can be used to measure individual trajectories of multiple particles over a time-scale of at least 3.335 s (50 frames).

In some embodiments, the particles of the invention have a relative velocity of greater than or equal to about 0.3, greater than or equal to about 0.5, greater than or equal to about 0.7, greater than or equal to about 1.0, greater than or equal to about 1.5, or greater than or equal to about 2.0 in mucus. In some embodiments, particles of the invention have a relative velocity of less than about 10.0, less than about 6.0, less than about 2.0, less than about 1.5, less than about 1.0, or less than about 0.7 in mucus. Combinations of the above-noted ranges are possible (e.g., a relative velocity of greater than or equal to about 0.5 and less than about 6.0). Other ranges are also possible.

In certain embodiments, the particles of the invention diffuse through mucus or a mucosal barrier at a greater rate or diffusivity than negative control particles or corresponding particles (e.g., particles that are unmodified and/or not coated with a coating described herein). In some embodiments, the particles of the invention pass through mucus or a mucosal barrier at a rate of diffusivity that is at least about 10 times, about 30 times, about 100 times, about 300 times, about 1000 times, about 3000 times, about 10000 times higher than a control particle or a corresponding particle. In some embodiments, the particles of the invention pass through mucus or a mucosal barrier at a rate of diffusivity that is less than about 10000 times higher, less than about 3000 times higher, less than about 1000 times higher, less than about 300 times higher, less than about 100 times higher, less than about 30 times higher, or less than about 10 times higher than negative control particles or corresponding particles. Combinations of the above-referenced ranges are also possible (e.g., at least about 10 times and less than about 1000 times higher than negative control particles or corresponding particles). Other ranges are also possible.

For the purposes of the comparisons described herein, the corresponding particles may be approximately the same size, shape, and/or density as the particles of the invention but lack the coating that makes the particles of the invention mobile in mucus. In some embodiments, the measurement of the geometric mean square displacement and rate of diffusivity of the particles (e.g., the corresponding particles and particles of the invention) is based on a time scale of about 1 second, about 3 seconds, or about 10 seconds. Methods for determining the geometric mean square displacement and rate of diffusivity are known in the art. The particles of the invention may pass through mucus or a mucosal barrier with a geometric mean squared displacement that is at least about 10 times, about 30 times, about 100 times, about 300 times, about 1000 times, about 3000 times, about 10000 times higher than corresponding particles or negative control particles. In some embodiments, the particles of the invention pass through mucus or a mucosal barrier with a geometric mean squared displacement that is less than about 10000 times higher, less than about 3000 times higher, less than about 1000 times higher, less than about 300 times higher, less than about 100 times higher, less than about 30 times higher, or less than about 10 times higher than negative control particles or corresponding particles. Combinations of the above-referenced ranges are also possible (e.g., at least about 10 times and less than about 1000 times higher than negative control particles or corresponding particles). Other ranges are also possible.

In some embodiments, particles of the invention diffuse through a mucosal barrier at a rate approaching the rate or diffusivity at which the particles can diffuse through water.

In some embodiments, the particles of the invention pass through a mucosal barrier at a rate or diffusivity that is less than about 1/100, less than about 1/300, less than about 1/1000, less than about 1/3000, less than about 1/10,000 of the diffusivity that the particles diffuse through water under similar conditions. In some embodiments, particles of the invention pass through a mucosal barrier at a rate or diffusivity that is greater than or equal to about 1/10,000, greater than or equal to about 1/3000, greater than or equal to about 1/1000, greater than or equal to about 1/300, or greater than or equal to about 1/100 of the diffusivity that the particles diffuse through water under similar conditions. Combinations of the above-referenced ranges are also possible (e.g., greater than or equal to about 1/3000 and less than 1/300 the diffusivity that the particles diffuse through water under similar conditions). Other ranges are also possible. The measurement of diffusivity may be based on a time scale of about 1 second, or about 0.5 second, or about 2 seconds, or about 5 seconds, or about 10 seconds.

In some embodiments, the particles of the invention diffuse through human cervicovaginal mucus at a diffusivity that is less than about 1/500 of the diffusivity that the particles diffuse through water. In some embodiments, the measurement of diffusivity is based on a time scale of about 1 second, or about 0.5 second, or about 2 seconds, or about 5 seconds, or about 10 seconds.

In certain embodiments, the particles of the invention travel through mucus, such as human cervicovaginal mucus, at certain absolute diffusivities. For example, the particles of the invention may travel at diffusivities of at least about $1 \times 10^{-4}$ μm/s, about $3 \times 10^{-4}$ μm/s, about $1 \times 10^{-3}$ μm/s, about $3 \times 10^{-3}$ μm/s, about $1 \times 10^{-2}$ μm/s, about $3 \times 10^{-2}$ μm/s, about $1 \times 10^{-1}$ μm/s, about $3 \times 10^{-1}$ μm/s, about 1 μm/s, or about 3 μm/s. In some embodiments, the particles may travel at diffusivities of less than about 3 μm/s, less than about 1 μm/s, less than about $3 \times 10^{-1}$ μm/s, less than about $1 \times 10^{-1}$ μm/s, less than about $3 \times 10^{-2}$ μm/s, less than about $1 \times 10^{-2}$ μm/s, less than about $3 \times 10^{-3}$ μm/s, less than about $1 \times 10^{-3}$ μm/s, less than about $3 \times 10^{-4}$ μm/s, or less than about $1 \times 10^{-4}$ μm/s. Combinations of the above-referenced ranges are also possible (e.g., greater than or equal to about $3 \times 10^{-4}$ μm/s and less than about $1 \times 10^{-1}$ μm/s). Other ranges are also possible. In some cases, the measurement of diffusivity is based on a time scale of about 1 second, or about 0.5 second, or about 2 seconds, or about 5 seconds, or about 10 seconds.

It should be appreciated that while the mobility (e.g., relative velocity and diffusivity) of the particles of the invention may be measured in human cervicovaginal mucus, the mobility may be measured in other types of mucus as well.

In certain embodiments, the particles of the invention comprise surface-altering moieties at a given density. The surface-altering moieties may be the portions of a surface-altering agent that are, for example, exposed to the solvent containing the particles. In one example, the hydrolyzed units/blocks of PVA may be surface-altering moieties of the surface-altering agent PVA. In another example, the PEG segments may be surface-altering moieties of the surface-altering agent PEG-PPO-PEG. In some embodiments, the surface-altering moieties and/or surface-altering agents are present at a density of at least about 0.001 units or molecules per $nm^2$, at least about 0.003, at least about 0.01, at least about 0.03, at least about 0.1, at least about 0.2, at least about 0.3, at least about 1, at least about 3, at least about 10, at least about 30, at least about 100 units or molecules per $nm^2$, or more units or molecules per $nm^2$. In some cases, the surface-altering moieties and/or surface-altering agents are present at a density of less than about 100 units or molecules per $nm^2$, less than about 30, less than about 10, less than about 3, less than about 1, less than about 0.3, less than about 0.2, less than about 0.1, less than about 0.03, or less than about 0.01 units or molecules per $nm^2$. Combinations of the above-referenced ranges are possible (e.g., a density of at least about 0.01 and less than about 1 units or molecules per $nm^2$). Other ranges are also possible. In some embodiments, the density values described herein are an average density as the surface altering agent is in equilibrium with other components in solution.

Those skilled in the art would be aware of methods to estimate the average density of surface-altering moieties (see, for example, Budijono et al., *Colloids and Surfaces A: Physicochem. Eng. Aspects* 2010, 360, 105-110; Joshi et al., *Anal. Chim. Acta* 1979, 104, 153-160). For example, as described herein, the average density of surface-altering moieties can be determined using HPLC quantitation and DLS analysis. A suspension of particles for which surface density determination is of interest is first sized using DLS: a small volume is diluted to an appropriate concentration (e.g., about 100 μg/mL), and the z-average diameter is taken as a representative measurement of particle size. The remaining suspension is then divided into two aliquots. Using HPLC, the first aliquot is assayed for the total concentration of core material and for the total concentration of the surface-altering moiety. Again using HPLC, the second aliquot is assayed for the concentration of free or unbound surface-altering moiety. In order to get only the free or unbound surface-altering moiety from the second aliquot, the particles, and therefore any bound surface-altering moiety, are removed by ultracentrifugation. By subtracting the concentration of the unbound surface-altering moiety from the total concentration of surface-altering moiety, the concentration of bound surface-altering moiety can be determined. Since the total concentration of core material was also determined from the first aliquot, the mass ratio between the core material and the surface-altering moiety can be determined. Using the molecular weight of the surface-altering moiety the number of surface-altering moiety to mass of core material can be calculated. To turn this number into a surface density measurement, the surface area per mass of core material needs to be calculated. The volume of the particle is approximated as that of a sphere with the diameter obtained from DLS allowing for the calculation of the surface area per mass of core material. In this way the number of surface-altering moieties per surface area can be determined.

In certain embodiments, the particles of the invention comprise surface-altering moieties and/or agents that affect the zeta-potential of the particle. The zeta potential of the particle may be, for example, at least about −100 mV, at least about −30 mV, at least about −10 mV, at least about −3 mV, at least about 3 mV, at least about 10 mV, at least about 30 mV, or at least about 100 mV. The zeta potential of the particle may also be, for example, less than about 100 mV, less than about 30 mV, less than about 10 mV, less than about 3 mV, less than about −3 mV, less than about −10 mV, less than about −30 mV, or less than about −100 mV. Combinations of the above-referenced ranges are possible (e.g., a zeta-potential of at least about −30 mV and less than about 30 mV). Other ranges are also possible.

The particles of the invention may have any suitable shape and/or size. In some embodiments, the particle has a shape substantially similar to the shape of the core. In some embodiments, the particle is a nanoparticle. In some embodiments, the particle is a microparticle. A plurality of particles, in some embodiments, may also be characterized by an average size (e.g., an average largest cross-sectional dimension or average smallest cross-sectional dimension for a plurality of particles). A plurality of particles may have an average size of, for example, less than about 10 µm, less than about 3 µm, less than about 1 µm, less than about 500 nm, less than 400 nm, less than 300 nm, less than about 200 nm, less than about 100 nm, less than about 50 nm, less than about 30 nm, or less than about 10 nm. In some cases, a plurality of particles may have an average size of, for example, at least about 10 nm, at least about 30 nm, at least about 50 nm, at least about 100 nm, at least about 200 nm, at least about 300 nm, at least about 400 nm, at least about 500 nm, at least about 1 µm, at least or at least about 3 µm. In one embodiment, a plurality of particles has an average size of less than about 400 nm. Combinations of the above-referenced ranges are also possible (e.g., an average size of at least about 30 nm and less than about 500 nm). Other ranges are also possible. In some embodiments, the sizes of the cores of the particles of the invention have a Gaussian-type distribution. In some embodiments, the sizes of the particles of the invention have a Gaussian-type distribution.

Pharmaceutical Agents

A particle or pharmaceutical composition of the invention may comprise at least one pharmaceutical agent. In certain embodiments, the pharmaceutical agent described herein is a pharmaceutically acceptable salt, solvate, hydrate, polymorph, tautomer, stereoisomer, isotopically labeled derivative, or prodrug of another pharmaceutical agent. In certain embodiments, the pharmaceutical agent is a co-crystal with another substance (e.g., a solvent, protein, or another pharmaceutical agent). The pharmaceutical agent may be present in the core and/or one or more coatings of the particle (e.g., dispersed throughout the core and/or coating). In some embodiments, the pharmaceutical agent may be disposed on the surface of the particle (e.g., on the outer or inner surface of the one or more coatings or on the surface of the core). The pharmaceutical agent may be contained within the particle and/or disposed in a portion of the particle using commonly known techniques (e.g., coating, adsorption, covalent linkage, and encapsulation). In some embodiments, the pharmaceutical agent is present during the formation of the core. In other embodiments, the pharmaceutical agent is not present during the formation of the core. In certain embodiments, the pharmaceutical agent is present during the coating of the core.

In some embodiments, the pharmaceutical agent contained in a particle or pharmaceutical composition of the invention has a therapeutic and/or prophylactic effect in a mucosal tissue to be targeted. Non-limiting examples of mucosal tissues include respiratory (e.g., including nasal, pharyngeal, tracheal, and bronchial membranes), oral (e.g., including the buccal and esophagal membranes and tonsil surface), ophthalmic, gastrointestinal (e.g., including stomach, small intestine, large intestine, colon, rectum), nasal, and genital (e.g., including vaginal, cervical and urethral membranes) tissues. In a preferred embodiment, the target tissue is respiratory (e.g., including nasal, pharyngeal, tracheal, and bronchial membranes).

Any suitable number of pharmaceutical agents may be present in a particle or pharmaceutical composition of the invention. For example, at least 1, at least 2, at least 3, at least 4, at least 5, or more pharmaceutical agents may be present in the particle or pharmaceutical composition of the invention. In certain embodiments, less than 10 pharmaceutical agents are present in the particle or pharmaceutical composition of the invention.

In certain embodiments, the pharmaceutical agent in the particles or pharmaceutical compositions of the invention is a compound of the invention. In certain embodiments, the pharmaceutical agent is one that is known to be mucoadhesive (see, for example, Khanvilkar et al., *Adv. Drug Delivery Rev.* 2001, 48, 173-193; Bhat et al., *J. Pharm. Sci.* 1996, 85, 624-30). Non-limiting examples of the pharmaceutical agent include imaging and diagnostic agents (such as radioopaque agents, labeled antibodies, labeled nucleic acid probes, dyes (e.g., colored or fluorescent dyes), and adjuvants (e.g., radiosensitizers, transfection-enhancing agents, chemotactic agents, and chemoattractants, peptides that modulate cell adhesion and/or cell mobility, cell permeabilizing agents, vaccine potentiators, and inhibitors of multidrug resistance and/or efflux pumps).

The pharmaceutical agent in the particles or pharmaceutical compositions of the invention may be a therapeutic agent, diagnostic agent, imaging agent, agent with a detectable label, nucleic acid, nucleic acid analog, small molecule, peptidomimetic, protein, peptide, lipid, vaccine, viral vector, virus, or surfactant. In certain embodiments, the pharmaceutical agent is an antibiotic agent. In certain embodiments, the antibiotic agent is anti-bacterial agent, anti-viral agent, antifungal agent, antiprotozoan, or antiparasitic agent. In certain embodiments, the antibiotic agent is a lactam antibiotic agent. In certain embodiments, the antibiotic agent is a β-lactam antibiotic agent. In certain embodiments, the β-lactam antibiotic agent is a carbapenem. In certain embodiments, the carbapenem is meropenem. In certain embodiments, the carbapenem is biapenem. In certain embodiments, the carbapenem is ertapenem. In certain embodiments, the carbapenem is doripenem. In certain embodiments, the carbapenem is imipenem. In certain embodiments, the carbapenem is panipenem. In certain embodiments, the β-lactam antibiotic agent is a penicillin (i.e., a penam, e.g., an aminopenicillin (e.g., amoxicillin, an ampicillin (e.g., pivampicillin, hetacillin, bacampicillin, metampicillin, talampicillin), epicillin), a carboxypenicillin (e.g., a carbenicillin (e.g., carindacillin), ticarcillin, temocillin), a ureidopenicillin (e.g., azlocillin, piperacillin, mezlocillin), a mecillinam (e.g, pivmecillinam), sulbenicillin, benzylpenicillin, clometocillin, benzathine benzylpenicillin, procaine benzylpenicillin, azidocillin, penamecillin, phenoxymethylpenicillin, propicillin, benzathine phenoxymethylpenicillin, pheneticillin, a cloxacillin (e.g., dicloxacillin, flucloxacillin), oxacillin, methicillin, nafcillin, a penem (e.g, faropenem), a cephem (e.g., cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefininox, cefonicid, ceforanide, cefotiam, cefprozil, cefbuperazone, cefuroxime, cefuzonam, a cephamycin (e.g, cefoxitin, cefotetan, cefmetazole), a carbacephem (e.g., loracarbef), cefixime, ceftriaxonc, an antipseudomonal (e.g., ceftazidime, cefoperazone), cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, an oxacephem (e.g., flomoxef, latamoxef), cefepime, cefozopran, cefpirome, cefquinome, ceftobiprole, ceftaroline fosamil, ceftiofutir, cefquinome, cefovecin, a monobactam (e.g., aztreonam, tigemonam, carumonam, nocardicin A), or combination thereof. In certain embodiments, the pharmaceutical agent is an anti-inflammatory agent. In certain embodiments, the pharmaceutical agent is a pain-relieving agent. In certain embodiments, the pharmaceutical agent is an anti-proliferative agent (e.g., an anti-cancer agent). Additional non-limiting examples of the pharmaceutical agent in the particles or pharmaceutical compositions of the invention include benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim, dicoumarol, dipyridamole, nicoumalone, phenindione, amoxapine, maprotiline HCl, mianserin HCL, nortriptyline HCl, trazodone HCL, trimipramine maleate, acetohexamide, chlorpropamide, glibenclamide, gliclazide, glipizide, tolazamide, tolbutamide, beclamide, carbamazepine, clonazepam, ethotoin, methoin, methsuximide, methylpheno barbi tone, oxcarbazepine, paramethadione, phenacemide, phenobarbitone, phenytoin, phensuximide, primidone, sulthiame, valproic acid, amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid, allopurinol, probenecid, sulphin-pyrazone, amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, rescrpine, terazosin HCL, amodiaquine, chloroquine, chlorproguanil HCl, halofantrine HCl, mefloquine HCl, roguanil HCl, pyrimethamine, quinine sulphate, dihydroergotamine mesylate, ergotamine tartrate, methysergide maleate, pizotifen maleate, sumatriptan succinate, atropine, benzhexol HCl, biperiden, ethopropazine HCl, hyoscyamine, mepenzolate bromide, oxyphencylcimine HCl, tropicamide, aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone, benznidazole, clioquinol, decoquinate, diiodohydroxyquinoline, diloxanide furoate, dinitolmide, furzolidone, metronidazole, nimorazole, nitrofurazone, ornidazole, tinidazole, carbimazole, propylthiouracil, alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone, acebutolol, alprenolol, atenolol, labetalol, metoprolol, nadolol, oxprenolol, pindolol, propranolol, amrinone, digitoxin, digoxin, enoximone, lanatoside C, medigoxin, beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone, acetazolamide, amiloride, bendrofluazide, bumetanide, chlorothiazide, chlorthalidone, ethacrynic acid, frusemide, metolazone, spironolactone, triamterene, bromocriptine mesylate, lysuride maleate, bisacodyl, cimetidine, cisapride, diphenoxylate HCl, domperidone, famotidine, loperamide, mesalazine, nizatidine, omeprazole, ondansetron HCL, ranitidine HCl, sulphasalazine, acrivastine, astemizole, cinnarizine, cyclizine, cyproheptadie HCl, dimenhydrinate, flunarizine HCl, loratadine, meclozine HCl, oxatomide, terfenadine, bezafibrate, clofibrate, fenofibrate, gemfibrozil, probucol, amyl nitrate, glyceryl trinitrate, isosorbide dinitrate, isosorbide mononitrate, pentaerythritol tetranitrate, betacarotene, vitamin A, vitamin B 2, vitamin D, vitamin E, vitamin K, codeine, dextropropyoxyphene, diamorphine, dihydrocodeine, meptazinol, methadone, morphine, nalbuphine, pentazocine, clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone, amphetamine, dexamphetamine, dexfenfluramine, fenfluramine, mazindol, pazopanib, sorafenib, lapatinib, fluocinolone acetonide, semaxanib, axitinib, tivozanib, cediranib, linifanib, regorafenib, telatinib, vatalanib, MGCD-265, OST-930, KRN-633, bimatoprost, latanoprost, travoprost, aloxiprin, auranofin, azapropazone, benorylate, diflunisal, etodolac, fenbufen, fenoprofen calcim, flurbiprofen, furoscmide, ibuprofen, indomethacin, ketoprofen, loteprednol etabonate, meclofenamic acid, mefenamic acid, nabumetone, naproxen, oxyphenbutazone, phenylbutazone, piroxicam, sulindac, albendazole, bephenium hydroxynaphthoate, cambendazole, dichlorophen, ivermectin, mebendazole, oxamniquine, oxfendazole, oxantel embonate, praziquantel, pyrantel embonate, thiabendazole, amiodarone HCl, disopyramide, flecainide acetate, and quinidine sulphate. In certain embodiments, the pharmaceutical agent is a corticosteroid (e.g., loteprednol etabonate, hydrocortisone, cortisone, tixocortol, prednisolone, methylprednisolone, prednisone, triamcinolone, mometasone, amcinonide, budesonide, desonide, fluocinonide, fluocinolone, halcinonide, betamethasone, dexamethasone, fluocortolone, hydrocortisone, aclometasone, prednicarbate, clobetasone, clobetasol, fluprednidene, glucocorticoid, mineralocorticoid, aldosterone, deoxycorticosterone, fludrocortisone, halobetasol, diflorasone, desoximetasone, fluticasone, flurandrenolide, alclometasone, diflucortolone, flunisolide, or beclomethasone). In certain embodiments, the pharmaceutical agent is a non-steroidal anti-inflammatory drug (NSAID). In certain embodiments, the pharmaceutical agent is a salicylate (e.g., aspirin (acetylsalicylic acid), diflunisal, or salsalate). In certain embodiments, the pharmaceutical agent is a propionic acid derivative (e.g., ibuprofen, naproxen, fenoprofen, ketoprofen, dexketoprofen, flurbiprofen, oxaprozin, and loxoprofen). In certain embodiments, the pharmaceutical agent is an acetic acid derivative (e.g., indomethacin, sulindac, etodolac, ketorolac, diclofenac, and nabumetone). In certain embodiments, the pharmaceutical agent is an enolic acid (oxicam) derivative (e.g., piroxicam, meloxicam, tenoxicam, droxicam, lornoxicam, and isoxicam). In certain embodiments, the pharmaceutical agent is a fenamic acid derivative (fenamate) (e.g., mefenamic acid, meclofenamic acid, flufenamic acid, and tolfenamic acid). In certain embodiments, the pharmaceutical agent is a selective cox-2 inhibitor (coxib) (e.g., celecoxib, rofecoxib, valdecoxib, parecoxib, lumiracoxib, etoricoxib, and firocoxib). In certain embodiments, the pharmaceutical agent is a sulphonanilide (e.g., nimesulide). In certain embodiments, the pharmaceutical agent is licofelone. In certain embodiments, the pharmaceutical agent is an endogenous angiogenesis inhibitor (e.g., VEGFR-1 (e.g., pazopanib (VOTRIENT®), cediranib (RECENTIN®), tivozanib (AV-951), axitinib (INLYTA®), semaxanib), HER2 (lapatinib (TYKERB®, TYVERB), Linifanib (ABT-869), MGCD-265, and KRN-633), VEGFR-2 (e.g., regorafenib (BAY 73-4506), telatinib (BAY 57-9352), vatalanib (PTK787, PTK/IZK), MGCD-265, OSI- 930, and KRN-633), NRP-1, angiopoietin 2, TSP-1, TSP-2, angiostatin, endostatin, vasostatin, calreticulin, platelet factor-4, TIMP, CDAI, Meth-1, Meth-2, IFN-α, IFN-β, IFN-γ, CXCL10, IL-4, IL-12, IL-18, prothrombin (kringle domain-2), antithrombin III fragment, prolactin, VEGI, SPARC, osteopontin, maspin, canstatin, a proliferin-related protein, sorafenib (NEXAVAR®)), and restin). In certain embodiments, the pharmaceutical agent is an exogenous angiogenesis inhibitor (e.g., bevacizumab, itraconazole, carboxyamidotriazole, TNP-470, CM101, IFN-α, IL-12, platelet factor-4, suramin, SU5416, thrombospondin, VEGFR antagonist, an angiostatic steroid+heparin, a cartilage-derived angiogenesis inhibitory factor, a matrix metalloproteinase inhibitor, angiostatin, endostatin, 2-methoxyestradiol, tecogalan, tetrathiomolybdate, thalidomide, thiromnbospondin, prolactin, a $\alpha_v\beta_3$ inhibitor, linomide, and tasquinimod). In certain embodiments, the pharmaceutical agent is a prostaglandin analog. In certain embodiments, the pharmaceutical agent is latanoprost, travoprost, unoprostone, or bimatoprost. In certain embodiments, the pharmaceutical agent is a beta blocker. In certain embodiments, the pharmaceutical agent is a non-selective beta blocker (e.g., alprenolol, bucindolol, carteolol, carvedilol, labetalol, nadolol, oxprenolol, penbutolol, pindolol, propranolol, sotalol, timolol, and eucommia bark). In certain embodiments, the pharmaceutical agent is a $\beta_1$-selective blocker (e.g., acebutolol, atenolol, betaxolol, bisoprolol, celiprolol, esmolol, metoprolol, and nebivolol). In certain embodiments, the pharmaceutical agent is a $\beta_2$-selective blocker (e.g., butaxamine and ICI-118,551). In certain embodiments, the pharmaceutical agent is a $\beta_3$-selective blocker (e.g., SR 59230A). In certain embodiments, the pharm agent is an arbonic anhydrase inhibitor. In certain embodiments, the pharmaceutical agent is acetazolamide, brinzolamide, dorzolamide, dorzolamide and timolol, or methazolamide. In certain embodiments, the pharmaceutical agent is a carbonic anhydrase inhibitor.

The pharmaceutical agent described herein (e.g., a compound of the invention) may be encapsulated in a polymer, a lipid, a protein, or a combination thereof.

Pharmaceutical Compositions

In one aspect, the present invention provides pharmaceutical compositions comprising the compounds of the invention. In another aspect, the present invention provides pharmaceutical compositions comprising the plurality of particles of the invention. In certain embodiments, the pharmaceutical compositions of the invention are pharmaceutical compositions. The pharmaceutical compositions may also comprise one or more pharmaceutically acceptable excipients. The pharmaceutical compositions may further comprise one or more additional pharmaceutical agents described herein. In certain embodiments, the pharmaceutical compositions are useful for the delivery of a pharmaceutical agent described herein (e.g., a compound of the invention) through or to mucus or a mucosal surface in a subject. The pharmaceutical compositions may be delivered to the mucosal surface in the subject and may pass through a mucosal barrier in the subject (e.g., mucus), and/or may show prolonged retention and/or increased uniform distribution of the particles of the invention at the mucosal surface, e.g., due to reduced mucoadhesion. In certain embodiments, the pharmaceutical compositions are useful in increasing the bioavailability of the pharmaceutical agent in the subject. In certain embodiments, the pharmaceutical compositions are useful in increasing the concentration of the pharmaceutical agent in the subject. In certain embodiments, the pharmaceutical compositions are useful in increasing the exposure of the pharmaceutical agent in the subject. Moreover, the pharmaceutical compositions may be useful in treating and/or preventing a disease (e.g., a respiratory tract disease) in a subject.

In certain embodiments, the subject described herein is a human. In some embodiments, the subject is a human with cystic fibrosis and a pulmonary infection. In certain embodiments, the subject is an animal. The animal may be of either sex and may be at any stage of development. In certain embodiments, the subject is a fish. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is immunocompromised. For example, the subject may have reduced immune system function as a result of a disease such as HIV infection, acquired immunodeficiency syndrome (AIDS), cancer (e.g., a solid tumor or leukemia), bone marrow disorder, or a genetic immunodeficiency. In some embodiments, the subject is immunocompromised as a result of a medication, e.g., immunosuppressive therapy or chemotherapy, bone marrow transplant, stem cell transplant, or exposure to radiation. In some embodiments, reduced immune system function comprises neutropenia.

In certain embodiments, the respiratory tract disease is a respiratory tract infection. In certain embodiments, the respiratory tract infection is an upper respiratory tract infection. In certain embodiments, the upper respiratory tract infection is tonsillitis. In certain embodiments, the upper respiratory tract infection is pharyngitis. In certain embodiments, the upper respiratory tract infection is laryngitis. In certain embodiments, the upper respiratory tract infection is sinusitis. In certain embodiments, the upper respiratory tract infection is otitis media. In certain embodiments, the upper respiratory tract infection is influenza. In certain embodiments, the upper respiratory tract infection is avian influenza. In certain embodiments, the upper respiratory tract infection is common cold. In certain embodiments, the respiratory tract infection is a lower respiratory tract infection. In certain embodiments, the lower respiratory tract infection is bronchitis. In certain embodiments, the bronchitis is acute bronchitis. In certain embodiments, the bronchitis is chronic bronchitis. In certain embodiments, the lower respiratory tract infection is pneumonia (e.g., nosocomial pneumonia, severe community-acquired pneumonia). In certain embodiments, the lower respiratory tract infection is tuberculosis. In certain embodiments, the lower respiratory tract infection is influenza. In certain embodiments, the lower respiratory tract infection is avian influenza. The respiratory tract infection may be caused by pathogenic microorganisms, such as bacteria, viruses, fungi, protozoa, and parasites. In certain embodiments, the respiratory tract infection is caused by a *Pseudomonas* species. In certain embodiments, the respiratory tract infection is caused by *Pseudonmonas aeruginosa*. In certain embodiments, the respiratory tract infection is caused by a *Mycobacterium* species (e.g., *Mycobacterium tuberculosis*). In certain embodiments, the respiratory tract infection is caused by a *Streptococcus* species (e.g., *Streptococcus pneumoniae*). In certain embodiments, the respiratory tract infection is caused by a *Haemophilus* species (e.g., *Haemophilus influenzae*). In certain embodiments, the respiratory tract infection is caused by a *Chlamydophila* species (e.g., *Chlamydophila pneumoniae*). In certain embodiments, the respiratory tract infection is caused by a *Mycoplasma* species (e.g., *Mycoplasma pneumoniae*). In certain embodiments, the respiratory tract infection is caused by a *Staphylococcus* species (e.g., *Staphylococcus aureus*). In certain embodiments, the respiratory tract infection is caused by a *Moraxella* species (e.g., *Moraxella catarrhalis*). In certain embodiments, the respiratory tract infection is caused by a *Legionella* species (e.g., *Legionella pneumophila*). In certain embodiments, the respiratory tract infection is caused by Gram-negative bacilli. In certain embodiments, the respiratory tract infection is caused by a *Bordetella* species (e.g., *Bordetella pertussis*). In certain embodiments, the respiratory tract infection is caused by a rhinovirus, coronavirus, adenovirus, metapneumovirus, parainfluenza virus, or respiratory syncytial virus. In certain embodiments, the respiratory tract infection is caused by an influenzavirus (e.g., influenzavirus A (e.g., H1N1, H2N2, H3N2, or H5N1), influenzavirus B, or influenzavirus C). In certain embodiments, the respiratory tract disease is cystic fibrosis. In certain embodiments, the respiratory tract disease is asthma. In certain embodiments, the respiratory tract disease is chronic obstructive pulmonary disease (COPD). In certain embodiments, the respiratory tract disease is emphysema. In certain embodiments, the respiratory tract disease is pulmonary edema. In certain embodiments, the respiratory tract disease is lung cancer (e.g., small-cell lung carcinoma and non-small-cell lung carcinoma). In certain embodiments, the respiratory tract disease is acute respiratory distress syndrome (ARDS). In certain embodiments, the respiratory tract disease is pneumoconiosis. In certain embodiments, the respiratory tract disease is an interstitial lung disease (ILD) (e.g., sarcoidosis and idiopathic pulmonary fibrosis). In certain embodiments, the respiratory tract disease is pulmonary embolism (PE). In certain embodiments, the respiratory tract disease is pulmonary hypertension. In certain embodiments, the respiratory tract disease is pleural effusion. In certain embodiments, the respiratory tract disease is pneumothorax. In certain embodiments, the respiratory tract disease is mesothelioma. In certain embodiments, the respiratory tract disease is obesity hypoventilation syndrome. In certain embodiments, the respiratory tract disease is a neuromuscular respiratory disease (e.g., amyotrophic lateral sclerosis, muscular dystrophies, and myasthenia gravis).

The pharmaceutical compositions of the invention may include a pharmaceutically acceptable excipient or carrier. A pharmaceutically acceptable excipient or pharmaceutically acceptable carrier may include a non-toxic, inert solid, semi-solid or liquid filler, diluent, encapsulating material, or formulation auxiliary of any suitable type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN 80; buffering agents such as magnesium hydroxide and aluminum hydroxide; alginic acid; pyrogen-free water; isotonic saline; Ringer's solution; ethyl alcohol; phosphate buffer solutions; non-toxic lubricants such as sodium lauryl sulfate and magnesium stearate; coloring agents; releasing agents; coating agents; sweetening, flavoring, and perfuming agents; preservatives; antioxidants, tonicity adjusting agents; viscosity modifiers; and suspension stabilizers. The pharmaceutical compositions of the invention may be lyophilized or subjected to another appropriate drying technique (e.g., spray drying). As would be appreciated by one of skill in the art, the excipients may be chosen based on the route of administration, pharmaceutical agent being delivered, and time course of delivery of the pharmaceutical agent.

The pharmaceutical compositions of the invention may be administered to a subject via any route known in the art. These include, but are not limited to, inhalational, oral, sublingual, nasal, intradermal, subcutaneous, intramuscular, rectal, vaginal, intravenous, intraarterial, intracisternally, intraperitoneal, intravitreal, periocular, topical (as by powders, creams, ointments, or drops), and buccal administration. As would be appreciated by one skilled in the art, the route of administration and the effective dosage to achieve the desired biological effect may be determined by the pharmaceutical agent being administered, the target organ, the preparation being administered, time course of administration, disease being treated, and intended use.

The pharmaceutical compositions of the invention may be suitable for inhalational administration to a subject. In certain embodiments, the pharmaceutical composition is an inhaler. The pharmaceutical composition is an aerosol. In certain embodiments, the invention provides for associating the inventive particles comprising compounds of Formula (I) with carrier particles, where the size of the resulting associated particles of the invention that comprises at least one pharmaceutical agent is such as to permit inhalation of substantially all of the pharmaceutical agent into the respiratory tract upon administration. For example, the size of the associated particle is less than about 20 microns, e.g., in the range of about 1 to about 10 microns, e.g., in the range of about 1 to about 5 microns. Other ranges of size of the associated particle are also possible. The size of the particle may be reduced by conventional means, for example, by milling, precipitation, or micronization. The inhaler or aerosol may include, for example, between 0.005-90% w/w, between 0.005-50%, between 0.005-10%, between about 0.005-5% w/w, or between 0.01-1.0% w/w of the pharmaceutical agent relative to the total weight of the inhaler or aerosol. Other ranges are also possible.

The inhaler or aerosol may comprise a propellant. The propellant may include a polar adjuvant having a higher polarity and/or a higher boiling point than the propellant. In certain embodiments, the polar adjuvant improves the stability of the propellant. The polar adjuvant includes aliphatic (e.g., $C_{2-6}$) alcohols and aliphatic polyols, such as ethanol, isopropanol, and propylene glycol. A high content of the polar adjuvant in the inhaler or aerosol (e.g., in excess of 5% w/w) may tend to dissolve the pharmaceutical agent. In certain embodiments, the inhaler or aerosol includes a small quantity of the polar adjuvant (e.g., in the range of 0.05-3.0% w/w, e.g., about 1% w/w or about 0.1% w/w). In certain embodiments, the inhaler or aerosol may be substantially free of polar adjuvants. The propellant may also include a volatile adjuvant. Exemplary volatile adjuvants include saturated hydrocarbons (e.g., propane, n-butane, isobutane, pentane, and isopentane) and alkyl ethers (e.g., dimethyl ether). In certain embodiments, the content of the volatile adjuvant in the propellant is less than about 50% w/w. In certain embodiments, the inhaler or aerosol comprises more than one propellant. In certain embodiments, the inhaler or aerosol does not include any components which may provoke the degradation of stratospheric ozone. In some embodiments, the pharmaceutical compositions do not include propellants that comprise one or more chlorofluorocarbons, such as $CCl_3F$, $CCl_2F_2$, and $CF_3CCl_3$.

The inhaler or aerosol may further comprise a surfactant. The surfactant may be pharmaceutically acceptable upon inhalational administration. Exemplary surfactants include L-α-phosphatidylcholine (PC), 1,2-dipalmitoylphosphatidylcholine (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil. In certain embodiments, the inhaler or aerosol may further comprise more than one surfactant.

The pharmaceutical compositions of the invention may also be a nasal or oral spray, such that the pharmaceutical composition is delivered across a nasal or oral mucus layer. As another example, the pharmaceutical compositions may be tablets, capsules, granules, powders, or syrups for oral administration. Moreover, the pharmaceutical compositions may be administered parenterally as injections (intravenous, intramuscular, or subcutaneous), drop infusion preparations, or suppositories. For application by the ophthalmic mucous membrane route, the pharmaceutical compositions may be eye drops or eye ointments.

The pharmaceutical compositions of the invention may be prepared by dispersal of the compounds or particles of the invention in the selected propellant and/or co-propellant in an appropriate container, e.g., with the aid of sonication. The compounds or particles may be suspended in co-propellant and filled into a suitable container. The valve of the container is then sealed into place and the propellant introduced by pressure filling through the valve in the conventional manner. The compounds or particles may be thus suspended or dissolved in a liquefied propellant, sealed in a container with a metering valve and fitted into an actuator. Such metered dose inhalers are well known in the art. The metering valve may meter 10 to 500 μL and in certain embodiments, 25 to 150 μL. In certain embodiments, dispersal may be achieved using dry powder inhalers (e.g., SPINHALER) for the compounds or particles (which remain as dry powders). In some embodiments, nanospheres are suspended in an aqueous fluid and nebulized into fine droplets to be aerosolized into the respiratory tract.

Sonic nebulizers may be used because they minimize exposing the agent to shear, which may result in degradation of the compounds or particles. Ordinarily, an aqueous aerosol is made by formulating an aqueous suspension of the compounds or particles together with conventional pharmaceutically acceptable excipients (e.g., carriers and stabilizers). The carriers and stabilizers vary with the requirements of the particular pharmaceutical composition, but typically include non-ionic surfactants (e.g., TWEENs, PLURONIC®, or polyethylene glycol), innocuous proteins (e.g., serum albumin), sorbitan esters, oleic acid, lecithin, amino acids (e.g., glycine), buffers, salts, sugars, or sugar alcohols. Aerosols generally are prepared from isotonic solutions.

Liquid dosage forms for oral administration include pharmaceutically acceptable emulsions, microemulsions, solutions, suspensions, syrups, and elixirs. In addition to the active ingredients, the liquid dosage forms may contain inert diluents commonly used in the art (e.g., water or other solvents), solubilizing agents, and emulsifiers (e.g., ethyl alcohol, isopropyl alcohol, ethyl carbonate, ethyl acetate, benzyl alcohol, benzyl benzoate, propylene glycol, 1,3-butylene glycol, and dimethylformamide), oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof. Besides inert diluents, the oral pharmaceutical compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, such as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed, including synthetic mono- or diglycerides. In addition, fatty acids such as oleic acid are used in the preparation of injectables. In certain embodiments, the compounds or particles are suspended in a carrier fluid comprising 1% (w/v) sodium carboxymethyl cellulose and 0.1% (v/v) TWEEN 80.

The injectable formulations can be sterilized, for example, by filtration through a bacteria-retaining filter, or by incorporating sterilizing agents in the form of sterile solid pharmaceutical compositions which can be dissolved or dispersed in sterile water or other sterile injectable medium prior to use.

Pharmaceutical compositions for rectal or vaginal administration can be suppositories which can be prepared by mixing the compounds or particles with suitable non-irritating excipients or carriers such as cocoa butter, polyethylene glycol, or a suppository wax which are solids at ambient temperature but liquids at body temperature and thus melt in the rectum or vaginal cavity and release the compounds or particles.

Solid dosage forms for oral administration include capsules, tablets, pills, powders, and granules. In such solid dosage forms, the compounds or particles are mixed with at least one inert, pharmaceutically acceptable excipient, such as sodium citrate or dicalcium phosphate, and/or a) fillers or extenders, such as starches, lactose, sucrose, glucose, mannitol, and silicic acid; b) binders, such as carboxymethylcellulose, alginates, gelatin, polyvinylpyrrolidinone, sucrose, and acacia; c) humectants, such as glycerol; d) disintegrating agents, such as agar-agar, calcium carbonate, potato or tapioca starch, alginic acid, certain silicates, and sodium carbonate; e) solution retarding agents, such as paraffin; f) absorption accelerators, such as quaternary ammonium compounds; g) wetting agents, such as cetyl alcohol and glycerol monostearate; h) absorbents, such as kaolin and bentonite clay; i) lubricants, such as talc, calcium stearate, magnesium stearate, solid polyethylene glycols, sodium lauryl sulfate; and mixtures thereof. In the case of capsules, tablets, and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a pharmaceutical composition that they release the active ingredient(s) only, or preferentially, in a certain part of the intestinal tract, optionally, in a delayed manner. Examples of embedding pharmaceutical compositions which can be used include polymeric substances and waxes.

Solid pharmaceutical compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The compounds or particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the compounds or particles of the invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the compounds or particles of the invention, excipients, such as lactose, talc, silicic acid, aluminum hydroxide, calcium silicates, and polyamide powder, or mixtures thereof. Sprays can additionally contain customary propellants, such as chlorofluorohydrocarbons.

Transdermal patches have the added advantage of providing controlled delivery of a compound to the body. Such dosage forms can be made by dissolving or dispensing the compounds or particles in a proper medium. Absorption enhancers can also be used to increase the flux of the compounds or particles across the skin. The rate can be controlled by either providing a rate controlling membrane or by dispersing the compounds or particles in a polymer matrix or gel.

The compound of the invention may be provided in an effective amount in the pharmaceutical composition. The particles of the invention that comprise a pharmaceutical agent (e.g., a compound of the invention) may also be provided in an effective amount in the pharmaceutical composition. In certain embodiments, the effective amount is a therapeutically effective amount. In certain embodiments, the effective amount is a prophylactically effective amount. In certain embodiments, the effective amount is an amount useful for the treatment and/or prevention of a respiratory tract disease described herein. The effective amount of the compound or particle in the pharmaceutical composition may be useful for the treatment and/or prevention of the respiratory tract disease as a single agent or in combination with one or more pharmaceutical agents described herein. In certain embodiments, the effective amount is an amount useful for inhibiting the activity of a bacterial, viral, fungal, or protozoan enzyme. In certain embodiments, the effective amount is an amount useful for killing a bacterium, virus, fungus, or protozoon, or inhibiting the growth of a bacterium, virus, fungus, or protozoon. An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg. The concentration and/or amount of any pharmaceutical agent to be administered to a subject may be readily determined by one of ordinary skill in the art. Known methods are also available to assay local tissue concentrations, diffusion rates from particles and local blood flow before and after administration of the therapeutic formulation.

The pharmaceutical compositions of the invention may have any suitable osmolarity. In some embodiments, the pharmaceutical composition has an osmolarity of at least about 0 mOsm/L, at least about 25 mOsm/L, at least about 50 mOsm/L, at least about 100 mOsm/L, at least about 200 mOsm/L, or at least about 310 mOsm/L. In certain embodiments, the pharmaceutical composition has an osmolarity of less than about 310 mOsm/L, less than about 200 mOsm/L, less than about 100 mOsm/L, less than about 50 mOsm/L, less than about 25 mOsm/L, or less than about 5 mOsm/L. Combinations of the above-referenced ranges are also possible (e.g., an osmolarity of at least about 0 mOsm/L and less than about 50 mOsm/L). Other ranges are also possible. The osmolarity of the pharmaceutical composition can be varied by changing, for example, the concentration of salts present in the solvent of the pharmaceutical composition.

The pharmaceutical composition of the invention may include one or more pharmaceutical agents described herein, such as a compound of the invention. In certain embodiments, the pharmaceutical composition includes a plurality of particles of the invention that comprise one or more pharmaceutical agents in the core and/or coating of the particles. In some embodiments, the ratio of the weight of each one of the pharmaceutical agents to the weight of each one of the one or more surface-altering agents (e.g., PLURONIC® F127) present in the pharmaceutical composition is greater than or equal to about 1:100, greater than or equal to about 1:30, greater than or equal to about 1:10, greater than or equal to about 1:3, greater than or equal to about 1:1, greater than or equal to about 3:1, greater than or equal to about 10:1, greater than or equal to about 30:1, or greater than or equal to about 100:1. In some embodiments, the ratio of the weight of each one of the pharmaceutical agents to the weight of each one of the one or more surface-altering agents in a pharmaceutical composition is less than about 100:1, less than about 30:1, less than about 10:1, less than about 3:1, less than about 1:1, less than about 1:3: less than about 1:10, less than about 1:30, or less than about 1:100. Combinations of the above-noted ranges are possible (e.g., a ratio of greater than or equal to about 1:1 and less than about 10:1). Other ranges are also possible. In certain embodiments, the ratio is about 1:1, about 2:1, or about 10:1. In some embodiments, the pharmaceutical composition of the invention includes the above-noted ranges for the ratio of the weight of each one of the pharmaceutical agents to the weight of each one of the one or more surface-altering agents during a formation process and/or a dilution process described herein. In certain embodiments, the pharmaceutical composition includes the above-noted ranges for the ratio of the weight of each one of the pharmaceutical agents to the weight of each one of the one or more surface-altering agents immediately prior to the pharmaceutical composition being administered to a subject or contacted with a biological sample. The pharmaceutical agent may be present in the pharmaceutical composition of the invention in any suitable amount, e.g., at least about 0.01 wt %, at least about 0.1 wt %, at least about 1 wt %, at least about 5 wt %, at least about 10 wt %, at least about 30 wt % of the pharmaceutical composition. In some cases, the pharmaceutical agent may be present in the pharmaceutical composition at less than about 30 wt %, less than about 10 wt %, less than about 5 wt %, less than about 2 wt %, or less than about 1 wt % of the pharmaceutical composition. Combinations of the above-referenced ranges are also possible (e.g., present in an amount of at least about 0.1 wt % and less than about 10 wt % of the pharmaceutical composition). Other ranges are also possible. In certain embodiments, the pharmaceutical agent is about 0.1-2 wt % of the pharmaceutical composition. In certain embodiments, the pharmaceutical agent is about 2-20 wt % of the pharmaceutical composition. In certain embodiments, the pharmaceutical agent is about 0.2 wt %, about 0.4 wt %, about 1 wt %, about 2 wt %, about 5 wt %, or about 10 wt % of the pharmaceutical composition.

The pharmaceutical composition of the invention may also include a chelating agent. In certain embodiments, the pharmaceutical composition includes a plurality of particles of the invention that comprise the chelating agent in the core and/or coating of the particles. All chelating agents described herein are contemplated as being within the scope of this invention. In certain embodiments, the chelating agent is EDTA. In certain embodiments, the chelating agent is a salt of EDTA. In certain embodiments, the chelating agent is disodium EDTA. The chelating agent may be present at a suitable concentration in a pharmaceutical composition of the invention. In certain embodiments, the concentration of the chelating agent is greater than or equal to about 0.0003 wt %, greater than or equal to about 0.001 wt %, greater than or equal to about 0.003 wt %, greater than or equal to about 0.01 wt %, greater than or equal to about 0.03 wt %, greater than or equal to about 0.05 wt %, greater than or equal to about 0.1 wt %, greater than or equal to about 0.3 wt %, greater than or equal to about 1 wt %, or greater than or equal to about 3 wt % of the pharmaceutical composition. In certain embodiments, the concentration of the chelating agent is less than about 3 wt %, less than about 1 wt %, less than about 0.3 wt %, less than about 0.1 wt %, less than about 0.05 wt %, less than about 0.03 wt %, less than about 0.01 wt %, less than about 0.003 wt %, less than about 0.001 wt %, or less than about 0.0003 wt % of the pharmaceutical composition. Combinations of the above-noted ranges are possible (e.g., a concentration of the chelating agent of greater than or equal to about 0.01 wt % and less than about 0.3 wt % of the pharmaceutical composition). Other ranges are also possible. In certain embodiments, the concentration of the chelating agent is about 0.001-0.1 wt %, about 0.005 wt %, about 0.01 wt %, about 0.05 wt %, or about 0.1 wt %, of the pharmaceutical composition. In some embodiments, a chelating agent may be present in a pharmaceutical composition in one or more of the above-noted ranges during a formation process and/or a dilution process described herein. In certain embodiments, a chelating agent may be present in a pharmaceutical composition in one or more of the above-noted ranges immediately prior to the pharmaceutical composition being administered to a subject or contacted with a biological sample.

The pharmaceutical composition of the invention may include a tonicity agent to adjust the pharmaceutical composition to a desired osmolarity. In certain embodiments, the pharmaceutical composition includes a plurality of particles of the invention that comprise a tonicity agent in the core and/or coating of the particles. In certain embodiments, the desired osmolarity is isotonic and compatible with blood. In certain embodiments, the desired osmolarity is hypotonic. In certain embodiments, the desired osmolarity is hypertonic. All tonicity agents described herein are contemplated to being within the scope of the invention. In certain embodiments, the tonicity agent is glycerin. In certain embodiments, the tonicity agent is sodium chloride. In certain embodiments, a combination of one or more tonicity agents may be used. The tonicity agent may be present at a suitable concentration in a pharmaceutical composition of the invention. In certain embodiments, the concentration of the tonicity agent is greater than or equal to about 0.003 wt %, greater than or equal to about 0.01 wt %, greater than or equal to about 0.03 wt %, greater than or equal to about 0.1 wt %, greater than or equal to about 0.3 wt %, greater than or equal to about 1 wt %, greater than or equal to about 3 wt %, greater than or equal to about 10 wt %, or greater than or equal to about 30 wt % of the pharmaceutical composition. In certain embodiments, the concentration of the tonicity agent is less than about 30 wt %, less than about 10 wt %, less than about 3 wt %, less than about 1 wt %, less than about 0.3 wt %, less than about 0.1 wt %, less than about 0.03 wt %, less than about 0.01 wt %, or less than about 0.003 wt % of the pharmaceutical composition. Combinations of the above-noted ranges are possible (e.g., a concentration of the tonicity agent of greater than or equal to about 0.1 wt % and less than about 10 wt % of the pharmaceutical composition). Other ranges are also possible. In certain embodiments, the concentration of the tonicity agent is about 0.1-1%, about 0.5-3%, about 0.25 wt %, about 0.45 wt %, 0.9 wt %, about 1.2 wt %, about 2.4 wt %, or about 5 wt % of the pharmaceutical composition. In some embodiments, a tonicity agent may be present in a pharmaceutical composition in one or more of the above-noted ranges during a formation process and/or a dilution process described herein. In certain embodiments, a tonicity agent may be present in a pharmaceutical composition immediately prior to the pharmaceutical composition being administered to a subject or contacted with a biological sample.

In some embodiments, the pharmaceutical composition of the invention may have an osmolarity of at least about 0 mOsm/L, at least about 5 mOsm/L, at least about 25 mOsm/L, at least about 50 mOsm/L, at least about 100 mOsm/L, at least about 200 mOsm/L, at least about 310 mOsm/L, or at least about 450 mOsm/L. In certain embodiments, a pharmaceutical composition of the invention may have an osmolarity of less than about 450 mOsm/L, less than about 310 mOsm/L, less than about 200 mOsm/L, less than about 100 mOsm/L, less than about 50 mOsm/L, less than about 25 mOsm/L, or less than about 5 mOsm/L. Combinations of the above-referenced ranges are also possible (e.g., an osmolarity of at least about 0 mOsm/L and less than about 50 mOsm/L). Other ranges are also possible.

It is appreciated in the art that the ionic strength of an inventive pharmaceutical composition that comprises a plurality of particles of the invention may affect the polydispersity of the plurality of the particles. The ionic strength may also affect the colloidal stability of the plurality of the particles. For example, a relatively high ionic strength of the pharmaceutical composition may cause the plurality of particles to coagulate and therefore may destabilize the pharmaceutical composition. In some embodiments, the pharmaceutical composition is stabilized by repulsive inter-particle forces. For example, the plurality of particles may be electrically or electrostatically charged. Two charged particles may repel each other, preventing collision and aggregation. When the repulsive inter-particle forces weaken or become attractive, the plurality of particles may start to aggregate. For instance, when the ionic strength of the pharmaceutical composition is increased to a certain level, the charges (e.g., negative charges) of the plurality of particles may be neutralized by the oppositely charged ions present in the pharmaceutical composition (e.g., $Na^+$ ions in solution). As a result, the plurality of particles may collide and bond to each other to form aggregates (e.g., clusters or flocs) of larger sizes. The formed aggregates of particles may also differ in size, and thus the polydispersity of the pharmaceutical composition may also increase. For example, an inventive pharmaceutical composition comprising similarly-sized particles may become a pharmaceutical composition comprising particles having various sizes (e.g., due to aggregation) when the ionic strength of the pharmaceutical composition is increased beyond a certain level. In the course of aggregation, the aggregates may grow in size and eventually settle to the bottom of the container, and the pharmaceutical composition is considered colloidally unstable. Once the plurality of particles in a pharmaceutical composition form aggregates, it is usually difficult to disrupt the aggregates into individual particles.

Certain pharmaceutical compositions of the invention show unexpected properties in that, among other things, the presence of one or more ionic tonicity agents (e.g., a salt, such as NaCl) in the pharmaceutical compositions at certain concentrations actually decreases or maintains the degree of aggregation of the particles present in the pharmaceutical compositions, and/or does not significantly increase aggregation. In certain embodiments, the polydispersity of the pharmaceutical composition decreases, is relatively constant, or does not change by an appreciable amount upon addition of one or more ionic tonicity agents into the pharmaceutical composition. For example, in some embodiments, the polydispersity of a pharmaceutical composition is relatively constant in the presence of added ionic strength and/or when the added ionic strength of the pharmaceutical composition is kept relatively constant or increased (e.g., during a formation and/or dilution process described herein). In certain embodiments, when the ionic strength increases by at least 50%, the polydispersity increases by less than about 300%, less than about 100%, less than about 30%, less than about 10%, less than about 3%, or less than about 1%. In certain embodiments, when the ionic strength is increased by at least 50%, the polydispersity increases by greater than or equal to about 1%, greater than or equal to about 3%, greater than or equal to about 10%, greater than or equal to about 30%, or greater than or equal to about 100%. Combinations of the above-noted ranges are possible (e.g., an increase in polydispersity of less than 30% and greater than or equal to 3%). Other ranges are also possible.

The ionic strength of a pharmaceutical composition of the invention may be controlled (e.g., increased, decreased, or maintained) through a variety of means, such as the addition of one or more ionic tonicity agents (e.g., a salt, such as NaCl) to the pharmaceutical composition. In certain embodiments, the ionic strength of a pharmaceutical composition of the invention is greater than or equal to about 0.0003 M, greater than or equal to about 0.001 M, greater than or equal to about 0.003 M, greater than or equal to about 0.01 M, greater than or equal to about 0.03 M, greater than or equal to about 0.1 M, greater than or equal to about 0.3 M, greater than or equal to about 1 M, greater than or equal to about 3 M, or greater than or equal to about 10 M. In certain embodiments, the ionic strength of a pharmaceutical composition of the invention is less than about 10 M, less than about 3 M, less than about 1 M, less than about 0.3 M, less than about 0.1 M, less than about 0.03 M, less than about 0.01 M, less than about 0.003 M, less than about 0.001 M, or less than about 0.0003 M. Combinations of the above-noted ranges are possible (e.g., an ionic strength of greater than or equal to about 0.01 M and less than about 1 M). Other ranges are also possible. In certain embodiments, the ionic strength of a pharmaceutical composition of the invention is about 0.1 M, about 0.15 M, or about 0.3 M.

In certain embodiments, the polydispersity of a pharmaceutical composition does not change upon addition of one or more ionic tonicity agents into the pharmaceutical composition. In certain embodiments, the polydispersity does not significantly increase upon addition of one or more ionic tonicity agents into the pharmaceutical composition. In certain embodiments, the polydispersity increases to a level described herein upon addition of one or more ionic tonicity agents into the pharmaceutical composition.

The polydispersity of an inventive pharmaceutical composition that comprises a plurality of particles of the invention may be measured by the polydispersity index (PDI). In certain embodiments, the PDI of the pharmaceutical composition is less than about 1, less than about 0.8, less than about 0.6, less than about 0.4, less than about 0.3, less than about 0.2, less than about 0.15, less than about 0.1, less than about 0.05, less than about 0.01, or less than about 0.005. In certain embodiments, the PDI of the pharmaceutical composition is greater than or equal to about 0.005, greater than or equal to about 0.01, greater than or equal to about 0.05, greater than or equal to about 0.1, greater than or equal to about 0.15, greater than or equal to about 0.2, greater than or equal to about 0.3, greater than or equal to about 0.4, greater than or equal to about 0.6, greater than or equal to about 0.8, or greater than or equal to about 1. Combinations of the above-noted ranges are possible (e.g., a PDI of greater than or equal to about 0.1 and less than about 0.5). Other ranges are also possible. In certain embodiments, the PDI of the pharmaceutical composition is about 0.1, about 0.15, or about 0.2. In certain embodiments, the pharmaceutical composition is highly dispersible and does not tend to form aggregates. Even when the particles do form aggregates, the aggregates may be easily broken up into individual particles without rigorously agitating the pharmaceutical composition.

A pharmaceutical composition of the invention may be sterile before or upon administration of the pharmaceutical composition to a subject, or before or upon contacting with a biological sample. A sterile pharmaceutical composition is essentially free of pathogenic microorganisms, such as bacteria, microbes, fungi, viruses, spores, yeasts, molds, and others generally associated with infections. The pharmaceutical composition of the invention may be subject to an aseptic process and/or other sterilization process before or upon administered to the subject, or before or upon contacting with a biological sample. An aseptic process typically involves flash-heating a pharmaceutical composition or components thereof. An aseptic process typically involves expensive equipment (such as clean rooms, bacteria retaining filters, dry or steam heat) and laborious handling. Examples of other sterilization methods include radiation sterilization (e.g., gamma, electron, or x-ray radiation), heat sterilization, sterile filtration, and ethylene oxide sterilization. Unlike other sterilization methods, radiation sterilization has the advantage of high penetrating ability and instantaneous effects, without the need to control temperature, pressure, vacuum, or humidity in some instances. In certain embodiments, the radiation used to sterilize the pharmaceutical composition is gamma radiation. Gamma radiation may be applied in an amount sufficient to kill most or substantially all of the microbes in or on the pharmaceutical composition. The temperature of the pharmaceutical composition and the rate of radiation may be relatively constant during the entire gamma radiation period. Gamma irradiation may be performed at any suitable temperature (e.g., ambient temperature, about 40° C., or between about 30 to about 50° C.). In certain embodiments, the gamma irradiation is performed at about 40° C.

In some embodiments, when a sterilization process is performed on an inventive pharmaceutical composition that comprises a plurality of particles of the invention, the sterilization process does not: (1) significantly change the particle size of the particles; (2) significantly change the integrity of the active ingredient (such as a compound of the invention), if any; and (3) generate pharmaceutically unacceptable concentrations of impurities during or following the sterilization process. In certain embodiments, the impurities generated during or following the sterilization process are degradants of the active ingredient. In certain embodiments, the sterilization process results in the presence of one or more degradants in the pharmaceutical composition, each of which is independently present at at less than about 10 wt %, less than about 3 wt %, less than about 2 wt %, less than about 1 wt %, less than about 0.8 wt %, less than about 0.6 wt %, less than about 0.4 wt %, less than about 0.3 wt %, less than about 0.2 wt %, less than about 0.1 wt %, less than about 0.03 wt %, less than about 0.01 wt %, less than about 0.003 wt %, or less than about 0.001 wt % of the active ingredient before degradation. In some embodiments, the sterilization process results in the presence of one or more degradants in the pharmaceutical composition, each of which is independently present at greater than or equal to about 0.001 wt %, greater than or equal to about 0.003 wt %, greater than or equal to about 0.01 wt %, greater than or equal to about 0.03 wt %, greater than or equal to about 0.1 wt %, greater than or equal to about 0.3 wt %, greater than or equal to about 1 wt %, greater than or equal to about 3 wt %, or greater than or equal to about 10 wt % of the active ingredient before degradation. Combinations of the above-referenced ranges are also possible (e.g., each one of the one or more degradants is independently present at less than about 1 wt % and greater than or equal to about 0.01 wt % of the active ingredient before degradation). Other ranges are also possible. In some embodiments, one or more additives are included in the pharmaceutical composition of the invention to help achieve a relatively low amount of the one or more degradants. In certain embodiments, the additive is glycerin.

When gamma irradiation is used in a sterilization process, the cumulative amount of the gamma radiation used may vary. In certain embodiments, the cumulative amount of the gamma radiation is greater than or equal to about 0.1 kGray, greater than or equal to about 0.3 kGray, greater than or equal to about 1 kGray, greater than or equal to about 3 kGray, greater than or equal to about 10 kGray, greater than or equal to about 30 kGray, greater than or equal to about 100 kGray, or greater than or equal to about 300 kGray. In certain embodiments, the cumulative amount of the gamma radiation is less than about 0.1 kGray, less than about 0.3 kGray, less than about 1 kGray, less than about 3 kGray, less than about 10 kGray, less than about 30 kGray, less than about 100 kGray, or less than about 300 kGray. Combinations of the above-noted ranges are possible (e.g., a cumulative amount of the gamma radiation of greater than or equal to about 1 kGray and less than about 30 kGray). Other ranges are also possible. In certain embodiments, multiple doses of radiation are utilized to achieve a desired cumulative radiation dosage.

The inventive particles and pharmaceutical compositions comprising a pharmaceutical agent may improve or increase the delivery of the pharmaceutical agent to a target tissue of the respiratory tract of a subject. The delivery of the pharmaceutical agent may be characterized in various ways, such as the exposure, duration, concentration, and bioavailability of the pharmaceutical agent. The exposure of a pharmaceutical agent in a target tissue of the respiratory tract of a subject may be defined as the area under the curve (AUC) of the concentration of the pharmaceutical agent in the target tissue of the respiratory tract against time after administration. In some embodiments, the exposure of the pharmaceutical agent increases due to the coating of the particles that renders the particles mucus penetrating, compared to control particles comprising the pharmaceutical agent that have a similar average size as the coated particles but do not include the coating. In certain embodiments, the control particle is the core of a particle of the invention. In some embodiments, the particles and/or pharmaceutical compositions of the invention increase the exposure of the pharmaceutical agent by at least about 10%, at least about 30%, at least about 100%, at least about 3 fold, at least about 10 fold, at least about 30 fold, at least about 100 fold, at least about 300 fold, or at least about 1000 fold. In certain the particles, the particles and/or pharmaceutical compositions of the invention increase the exposure of the pharmaceutical agent by less than about 1000 fold, less than about 300 fold, less than about 100 fold, less than about 30 fold, less than about 10 fold, less than about 3 fold, less than about 100%, less than about 30%, or less than about 10%. Combinations of the above-referenced ranges are also possible (e.g., an increase of at least about 10% and less than about 10 fold). Other ranges are also possible. In certain embodiments, the coating on the core of the particles of the invention is present in a sufficient amount to increase the exposure of the pharmaceutical agent by an amount described herein when administered in the pharmaceutical composition compared to the exposure of the pharmaceutical agent when administered as a core without the coating.

In general, an increase in exposure may be calculated by taking the difference in the AUC measured in a target tissue of the respiratory tract between those of an inventive particle or pharmaceutical composition and a control particle or pharmaceutical composition, and dividing the difference by the exposure of the control particle or pharmaceutical composition.

Exposure of a pharmaceutical agent may be measured in an appropriate animal model (e.g. in a New Zealand white rabbit model). The concentration of a pharmaceutical agent and, when appropriate, its metabolite(s), in appropriate target tissue of the respiratory tracts or fluids is measured as a function of time after administration.

The concentration of a pharmaceutical agent in a target tissue of a respiratory tract of a subject may also be increased when the pharmaceutical agent is delivered (e.g., via inhalational administration to the subject) using the particles and/or pharmaceutical compositions of the invention. In some embodiments, the concentration of the pharmaceutical agent increases due to the coating of the particles that renders the particles mucus penetrating, compared to control particles comprising the pharmaceutical agent that have a similar average size as the coated particles but do not include the coating. In certain embodiments, the control particle is the core of a particle of the invention. In certain embodiments, a dose of the particles and/or pharmaceutical compositions is administered, followed by the measurement of the concentration of the pharmaceutical agent in the target tissue of the respiratory tract. For purposes of comparison, the amount of the pharmaceutical agent included in the administered dose of the particles and/or pharmaceutical compositions of the invention may be similar or substantially equal to the amount of the pharmaceutical agent included in the administered dose of the control particles and/or pharmaceutical compositions. In certain embodiments, the concentration of the pharmaceutical agent in the tissue is measured at a certain time subsequent to the administration ("time post-dose") of a dose of the particles and/or pharmaceutical compositions of the invention or of the control particles and/or pharmaceutical compositions. In certain embodiments, the time when the concentration is measured is about 1 min, about 10 min, about 30 min, about 1 h, about 2 h, about 3 h, about 6 h, about 12 h, about 18 h, about 24 h, about 36 h, or about 48 h post-dose. In some embodiments, the particles and/or pharmaceutical compositions of the invention increase the concentration of a pharmaceutical agent in the target tissue of the respiratory tract by at least about 10%, at least about 30%, at least about 100%, at least about 300%, at least about 10 fold, at least about 30 fold, at least about 100 fold, at least about 1000 fold, at least about $10^4$ fold, at least about $10^5$ fold, or at least about $10^6$ fold. In some embodiments, the particles and/or pharmaceutical compositions of the invention increase the concentration of a pharmaceutical agent in the target tissue of the respiratory tract by less than about $10^6$ fold, less than about $10^5$ fold, less than about $10^4$ fold, 1000 fold, less than about 100 fold, less than about 10 fold, less than about 300%, less than about 100%, less than about 30%, or less than about 10%. Combinations of the above-referenced ranges are also possible (e.g., an increase of greater than or equal to about 10% and less than about 100%). Other ranges are also possible. In certain embodiments, the coating on the core of the particles of the invention is present in a sufficient amount to increase the concentration of the pharmaceutical agent by an amount described herein when administered in the pharmaceutical composition compared to the exposure of the pharmaceutical agent when administered as a core without the coating. In certain embodiments, the coating of the inventive particle or pharmaceutical composition that comprises a pharmaceutical agent is present in a sufficient amount to increase the concentration of the pharmaceutical agent in an target tissue of the respiratory tract after at least 10 minutes, at least 30 minutes, at least 1 hour, at least 2 hours, at least 3 hours, at least 6 hours, at least 12 hours, or at least 24 hours after administration of the inventive particle or pharmaceutical composition. In certain embodiments, the coating of the inventive particle or pharmaceutical composition that comprises a pharmaceutical agent is present in a sufficient amount to increase the concentration of the pharmaceutical agent in a target tissue of a respiratory tract after less than 24 hours, less than 12 hours, less than 6 hours, less than 3 hours, less than 2 hours, less than 1 hour, less than 30 minutes, or less than 10 minutes after administration of the inventive particle or pharmaceutical composition. Combinations of the above-referenced ranges are also possible (e.g., the concentration of the pharmaceutical agent increases after at least 10 minutes and less than 2 hours after administration). Other ranges are also possible. In certain embodiments, the coating of the inventive particle or pharmaceutical composition that comprises a pharmaceutical agent is present in a sufficient amount to increase the concentration of the pharmaceutical agent in a target tissue of a respiratory tract after about 30 minutes after administration of inventive particle or pharmaceutical composition.

Concentration of a pharmaceutical agent, and, when appropriate, of its metabolite(s), in a target tissue of a respiratory tract, may be measured as a function of time in vivo using an appropriate animal model. One method of determining the concentration of a pharmaceutical agent involves dissecting of the respiratory tract to isolate the target tissue. The concentration of the pharmaceutical agent in the target tissues may then be determined by HPLC or LC/MS analysis.

Also encompassed by the invention are kits (e.g., pharmaceutical packs). The kit of the invention may comprise an inventive compound, particle, or pharmaceutical composition, and a container (e.g., a vial, ampule, bottle, syringe, and/or dispenser package, or other suitable container). In some embodiments, the kit further includes a second container comprising a pharmaceutical excipient for dilution or suspension of an inventive compound, particle, or pharmaceutical composition. In some embodiments, the inventive compound, particle, or pharmaceutical composition provided in the first container and the second container are combined to form one unit dosage form. The kits may be useful in treating and/or preventing a disease (e.g., a respiratory tract disease) in a subject. The kits may also be useful in delivering at least one pharmaceutical agent (e.g., a compound of the invention) to a subject. In certain embodiments, the kits are useful in increasing the bioavailability of the pharmaceutical agent in the subject. In certain embodiments, the kits are useful in increasing the concentration of the pharmaceutical agent in the subject. In certain embodiments, the kits are useful in increasing the exposure of the pharmaceutical agent in the subject. In certain embodiments, the kits further include instructions for administering the compound, particle, or pharmaceutical composition of the invention. In certain embodiments, the kits and instructions provide for treating and/or preventing a disease (e.g., a respiratory tract disease). The kit may include one or more additional pharmaceutical agents described herein.

Methods of Preparing the Particles and Pharmaceutical Compositions Thereof

In one aspect, the present invention provides methods of preparing the particles of the invention. Methods of preparing similar particles have been described in U.S. Published Patent Application No. 2013/0316006A1, published on Nov. 28, 2013, which is incorporated by reference herein in its entirety.

The core of the particle may be formed by any suitable method. Suitable methods may include, for example, top-down techniques, i.e. techniques based on size reduction of relatively large particles into smaller particles (e.g., milling or homogenization) or bottom-up techniques, i.e. techniques based on the growth of particles from smaller particles or individual molecules (e.g., precipitation or spray-freezing into liquid).

In some embodiments, the core of the particle may be coated with a coating. For example, the core may be provided or formed in a first step, and then the core may be coated in a second step. In some embodiments, the core particle is formed and coated substantially simultaneously (e.g., in a single step).

In some embodiments, the particle is formed by a method that involves using a formulation process, a milling process, and/or a dilution process. In certain embodiments, a method of forming the particle includes a milling process, optionally with a formulation process and/or a dilution process. A formulation process may be used to form a suspension comprising a core material, one or more surface-altering agents, and other components, such as solvents, tonicity agents, chelating agents, salts, and/or buffers (e.g., a sodium citrate and citric acid buffer), each of which is as described herein. The formulation process may be performed using a formulation vessel. The core material and other components may be added into the formulation vessel at the same time or different times. A mixture of the core material and/or one or more other components may be stirred and/or shaken, or otherwise agitated in the vessel to facilitate suspending the components to form the suspension. The temperature and/or pressure of the core material, other components, and/or mixture may also be individually increased or decreased to facilitate the suspending process. In some embodiments, the core material and other components are processed as described herein in the formulation vessel under an inert atmosphere (e.g., nitrogen or argon) and/or protected from light. The suspension obtained from the formulation vessel may be subsequently subject to a milling process which may be followed by a dilution process.

In some embodiments involving a core comprising a solid material, a milling process may be used to reduce the size of the solid material to form particles in a micrometer to nanometer size range. The milling process may be performed using a mill or other suitable apparatus. Dry and wet milling processes such as jet milling, cryo-milling, ball milling, media milling, sonication, and homogenization are known and can be used in methods of the invention. For example, in a wet milling process, a suspension of the solid material to be used to form the core ("core material") is agitated with or without excipients to reduce the size of the core to be formed. Dry milling is a process wherein the core material is mixed with milling media with or without excipients to reduce the size of the core to be formed. In a cyro-milling process, a suspension of the core material is mixed with milling media with or without excipients under cooled temperatures. In certain embodiments, when surface-altering agents are employed, a suspension comprising coated particles is obtained from the milling process. In certain embodiments, when surface-altering agents are not employed, a suspension comprising uncoated particles is obtained from the milling process.

The suspension of particles (coated or uncoated) of the invention obtained from a milling process may be further processed with a dilution process. A dilution process may be used to achieve a target dosing concentration by diluting a suspension of particles that were formed during a milling process, with or without surface-altering agents and/or other components. In certain embodiments, when a suspension of coated particles that comprise a first surface-altering agent is processed with a dilution process involving a second surface-altering agent, a suspension of coated particles that comprise the second surface-altering agent is obtained from the dilution process. In certain embodiments, when a suspension of coated particles that comprise a surface-altering agent is processed with a dilution process involving no or the same surface-altering agent, a suspension of coated particles that comprise the surface-altering agent is obtained from the dilution process. In certain embodiments, when a suspension of uncoated particles is processed with a dilution process involving a surface-altering agent, a suspension of coated particles comprising the surface-altering agent is obtained from the dilution process. The dilution process may be performed using a product vessel or any other suitable apparatus. In certain embodiments, the suspension of the particles is diluted, i.e., mixed or otherwise processed with a diluent, in the product vessel. The diluent may contain solvents, surface-altering agents, tonicity agents, chelating agents, salts, or a combination thereof, as described herein. The suspension and the diluent may be added into the product vessel at the same time or different times. In certain embodiments when the suspension is obtained from a milling process involving milling media, the milling media may be separated from the suspension before the suspension is added into the product vessel. The suspension, the diluent, or the mixture of the suspension and the diluent may be stirred and/or shaken, or otherwise agitated, to form the particles and/or pharmaceutical compositions of the invention. The temperature and/or pressure of the suspension, the diluent, or the mixture may also be individually increased or decreased to form the coated particles. In some embodiments, the suspension and the diluent are processed in the product vessel under an inert atmosphere (e.g., nitrogen or argon) and/or protected from light.

In some embodiments, the core and/or coated particles may be produced by milling of a solid material (e.g., a pharmaceutical agent) in the presence of one or more surface-altering agents. Small particles of a solid material may require the presence of one or more surface-altering agents, which may function as a stabilizer in some embodiments, in order to stabilize a suspension of particles without agglomeration or aggregation in a liquid solution. In some such embodiments, the stabilizer may act as a surface-altering agent, forming the coated particles of the invention.

As described herein, a method of forming the core and/or the coated particles, may involve choosing a surface-altering agent that is suitable for both milling and forming a coating on the core, wherein the coating renders the particle mucus penetrating. For example, as described in more detail below, it has been demonstrated that particles of pyrene that were produced by milling of pyrene in the presence of certain PLURONICS® polymers had and had an average size of about 200-500 nm were capable of penetrating physiological mucus samples at the same rate as well-established PEGylated polymeric mucus-penetrating particles (MPPs). Interestingly, it was observed that only a subset of PLURONICS® polymers tested were suitable for both milling and forming the coating that renders the particle mucus penetrating.

In a wet milling process, milling may be performed in a dispersion (e.g., an aqueous dispersion) containing at least one surface-altering agent, a grinding medium, a solid to be milled (e.g., a solid pharmaceutical agent), and a solvent. The solvent described herein includes a single solvent or a mixture of different solvents. Any suitable amount of a surface-altering agent can be included in the solvent. In some embodiments, the surface-altering agent may be present in the solvent in an amount of at least about 0.001% (wt % or % weight to volume (w:v)), at least about 0.01%, at least about 0.1%, at least about 1%, at least about 3%, at least about 10%, at least about 30%, or at least about 60% of the solvent. In some cases, the surface-altering agent may be present in the solvent in an amount of about 100% (e.g., in an instance where the surface-altering agent is the solvent). In other embodiments, the surface-altering agent may be present in the solvent in an amount of less than about 100%, less than about 60%, less than about 30%, less than about 10%, less than about 3%, or less than about 1% of the solvent. Combinations of the above-referenced ranges are also possible (e.g., an amount of less than about 3% and at least about 1% of the solvent). Other ranges are also possible. In certain embodiments, the surface-altering agent is present in the solvent in an amount of about 0.01-2%, about 0.2-20%, about 0.1%, about 0.4%, about 1%, about 2%, about 5%, or about 10% of the solvent.

The particular range chosen may influence factors that may affect the ability of the particles to penetrate mucus such as the stability of the coating of the surface-altering agent on the particle surface, the average thickness of the coating of the surface-altering agent on the particles, the orientation of the surface-altering agent on the particles, the density of the surface altering agent on the particles, the ratio of the surface-altering agent to pharmaceutical agent, the concentration of the pharmaceutical agent, the size, dispersibility, and polydispersity of the particles formed, and the morphology of the particles formed.

The pharmaceutical agent may be present in the solvent in any suitable amount. In some embodiments, the pharmaceutical agent is present in an amount of at least about 0.001% (wt % or % weight to volume (w:v)), at least about 0.01%, at least about 0.1%, at least about 1%, at least about 3%, at least about 10%, at least about 30%, or at least about 60% of the solvent. In some cases, the pharmaceutical agent may be present in the solvent in an amount of less than about 100%, less than about 60%, less than about 30%, less than about 10%, less than about 3%, or less than about 1% of the solvent. Combinations of the above-referenced ranges are also possible (e.g., an amount of less than about 30% and at least about 1% of the solvent).

The ratio of surface-altering agent to pharmaceutical agent in a solvent may also vary. In some embodiments, the ratio of the surface-altering agent to pharmaceutical agent is at least about 0.001:1 (weight ratio, molar ratio, or w:v), at least about 0.01:1, at least about 0.01:1, at least about 1:1, at least about 2:1, at least about 3:1, at least about 5:1, at least about 10:1, at least about 30:1, at least about 100:1, or at least about 1000:1. In some embodiments, the ratio of the surface-altering agent to pharmaceutical agent is less than 1000:1 (weight ratio, molar ratio, or w:v), less than about 100:1, less than about 30:1, less than about 10:1, less than about 5:1, less than about 3:1, less than about 2:1, less than about 1:1, or less than about 0.1:1. Combinations of the above-referenced ranges are possible (e.g., a ratio of at least about 5:1 and less than about 30:1). Other ranges are also possible.

The surface-altering agents described herein that may act as stabilizers may be, for example, polymers or surfactants. Examples of polymers include those suitable for use in the coating of the particles of the invention, such as poly(vinyl alcohol) and PLURONICS®. Examples of surfactants include L-α-phosphatidylcholine (PC), 1,2-dipalmitoylphosphatidycholine (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol, cetyl pyridinium chloride, benzalkonium chloride, olive oil, glyceryl monolaurate, corn oil, cotton seed oil, and sunflower seed oil.

A stabilizer used for milling may form the coating of a particle of the invention, wherein the coating renders the particle mucus penetrating. The stabilizer may also be exchanged with one or more other surface-altering agents after the particle has been formed. For example, a first stabilizer/surface-altering agent may be used during a milling process and may form a first coating of the particle of the invention, and all or part of the first stabilizer/surface-altering agent may then be exchanged with a second stabilizer/surface-altering agent to form a second coating of the particle. In some embodiments, the second stabilizer/surface-altering agent may render the particle mucus penetrating more than the first stabilizer/surface-altering agent. In some embodiments, a particle comprising multiple coatings that include multiple surface-altering agents is formed by a method of the invention.

Any suitable grinding medium can be used for milling. In some embodiments, a ceramic and/or polymeric material and/or a metal can be used. Examples of suitable materials include zirconium oxide, silicon carbide, silicon oxide, silicon nitride, zirconium silicate, yttrium oxide, glass, alumina, alpha-alumina, aluminum oxide, polystyrene, poly (methyl methacrylate), titanium, and steel. A grinding medium may have any suitable size. For example, the grinding medium may have an average diameter of at least about 0.1 mm, at least about 0.2 mm, at least about 0.5 mm, at least about 0.8 mm, at least about 1 mm, at least about 2 mm, or at least about 5 mm. In some cases, the grinding medium may have an average diameter of less than about 5 mm, less than about 2 mm, less than about 1 mm, less than about 0.8, less than about 0.5 mm, or less than about 0.2 mm. Combinations of the above-referenced ranges are also possible (e.g., an average diameter of at least about 0.5 millimeters and less than about 1 mm). Other ranges are also possible.

A solvent may be used for milling. The choice of the solvent suitable for milling may depend on factors like the solid material (e.g., a solid pharmaceutical agent) being milled, the particular type of stabilizer/surface-altering agent (e.g., one that may render the particle mucus penetrating), and the grinding material. The solvent suitable for milling may be one of those solvents that do not substantially dissolve the solid material or the grinding material, but dissolve the stabilizer/surface-altering agent to a suitable degree. Examples of the solvents suitable for milling include water, aqueous solutions, buffered solutions, alcohols (e.g., ethanol, methanol, and butanol), and mixtures thereof, each of which may optionally include other components, such as one or more pharmaceutical excipients, polymers, pharmaceutical agents, salts, preservative agents, viscosity modifiers, tonicity modifiers, taste masking agents, antioxidants, and pH modifiers. In some embodiments, the solvent suitable for milling is an organic solvent.

A pharmaceutical agent described herein (e.g., a compound of the invention) may have a suitable solubility in a solvent suitable for milling, such as a solubility in one or more ranges described herein for aqueous solubility or for solubility in a coating solution. A pharmaceutical agent having a relatively low solubility in a solvent (e.g., water or a coating solution) may be preferred because a milling process described herein typically requires a material (e.g., a pharmaceutical agent) to be in a solid form in order for the material to be milled. In some cases, if the material to be milled has a relatively high soluble in a solvent (e.g., water or a coating solution) used in the milling process, milling may not be conducted because significant or complete dissolution of the material to be milled in the solvent will occur. In certain embodiments, a relatively high solubility of a solid material (e.g., a solid pharmaceutical agent) in a solvent is at least about 1 mg/mL, at least about 3 mg/mL, or at least about 10 mg/mL at 25° C. In certain embodiments, a relatively low solubility of a substance (e.g., a pharmaceutical agent) in a solvent is less than about 1 mg/mL, less than about 0.3 mg/mL, less than about 0.1 mg/mL, less than about 0.03 mg/mL, less than about 0.01 mg/mL, less than about 0.003 mg/mL, or less than about 0.001 mg/mL at 25° C. The solid material may have these or other ranges of solubilities at any point throughout the pH range (e.g., from pH 1 to pH 14). A pharmaceutical agent that has a relatively high solubility in the solvent used in the milling process may be modified to form a prodrug of the pharmaceutical agent. The prodrug may have a relatively low solubility and thus may be suitable for the milling process. Upon or after the particles or pharmaceutical compositions comprising the prodrug are administered to a subject, the prodrug may be converted and form or, in other words, "release," the pharmaceutical agent.

In other embodiments, the core and/or coated particles may be formed by an emulsification process or technique (emulsification) known in the art. See, e.g., U.S. Published Patent Application No. 2013/0316006A1, published on Nov. 28, 2013.

The core and/or coated particles may also be formed by a precipitation process or technique (precipitation). Precipitation techniques (e.g., microprecipitation, nanoprecipitation, crystallization, and controlled crystallization) may involve forming a first solution comprising the material that is to form the core (e.g., a pharmaceutical agent) and a first solvent, wherein the material has a relatively high solubility in the first solvent. The first solution may be added to a second solution comprising a second solvent that is an anti-solvent, in which the material has a relatively low solubility, thereby forming a plurality of particles comprising the material. In certain embodiments, the second solvent is miscible with the first solvent. In some embodiments, one or more surface-altering agents and/or surfactants may be present in the first and/or second solutions. A coating may be formed during the process of precipitating the core (e.g., the coating of the particles may be formed substantially simultaneously when the precipitation is performed) to form the coated particles of the invention.

In other embodiments, the core of the particles of the invention is first formed using a precipitation technique, following by coating of the core with a surface-altering agent to form the coated particles of the invention.

In some embodiments, a precipitation technique may be used to form polymeric core of the particles of the invention with or without a pharmaceutical agent. Generally, a precipitation technique involves dissolving a polymer that is to form the core in a first solvent, in the presence or absence of a pharmaceutical agent, to form a solution. The solution is then added to a second solvent that is an anti-solvent and is miscible with the first solvent, in the presence or absence of one or more excipients, to form the core of the particles. In some embodiments, precipitation is useful for preparing a polymeric core comprising one or more pharmaceutical agents having a relatively low aqueous solubility.

The precipitation described herein involves the use of a first solvent. Examples of suitable first solvents for precipitation include organic solvents (e.g., acetone, acetonitrile, dimethylformamide, dimethysulfoxide, N-methyl-2-pyrrolidone, 2-pyrrolidone, and tetrahydrofuran) and inorganic solvents.

The precipitation described herein also involves the use of a second solvent. In certain embodiments, the second solvent suitable for precipitation is an anti-solvent. Examples of second solvents suitable for precipitation include the solvents described herein that may be used for milling. In some embodiments, the second solvents suitable for precipitation is water, an aqueous solution (e.g., a buffered solution), an alcohol (e.g., methanol, ethanol, propanol, or butanol), or a mixture thereof, optionally including one or more other components, such as pharmaceutical excipients, polymers, and pharmaceutical agents.

Surface-altering agents for the emulsification and precipitation described herein may be polymers or surfactants, including the surface-altering agents described herein that may be used for milling.

Examples of polymers suitable for forming all or part of the core of the particles of the invention by the emulsification or precipitation include the polymers (including copolymers) described herein.

In some embodiments, a precipitation technique may be used to form particles comprised predominantly of a pharmaceutical agent (e.g., a compound of the invention). In certain embodiments, the particles of the invention formed by the precipitation technique comprise predominantly of a pharmaceutical agent that is a nanocrystal. Generally, such a precipitation technique involves dissolving the pharmaceutical agent that is to form the core in a first solvent, which is then added to a second solvent that is an anti-solvent, in which the pharmaceutical agent has a relatively low solubility, in the presence or absence of one or more pharmaceutical excipients, to form the core or uncoated particle. In some embodiments, this technique may be useful for preparing, for example, particles of pharmaceutical agents that are slightly soluble (1-10 mg/mL), very slightly soluble (0.1-1 mg/mL) or practically insoluble (<0.1 mg/mL) in aqueous solutions (e.g., agents having a relatively low aqueous solubility).

Figure 6:
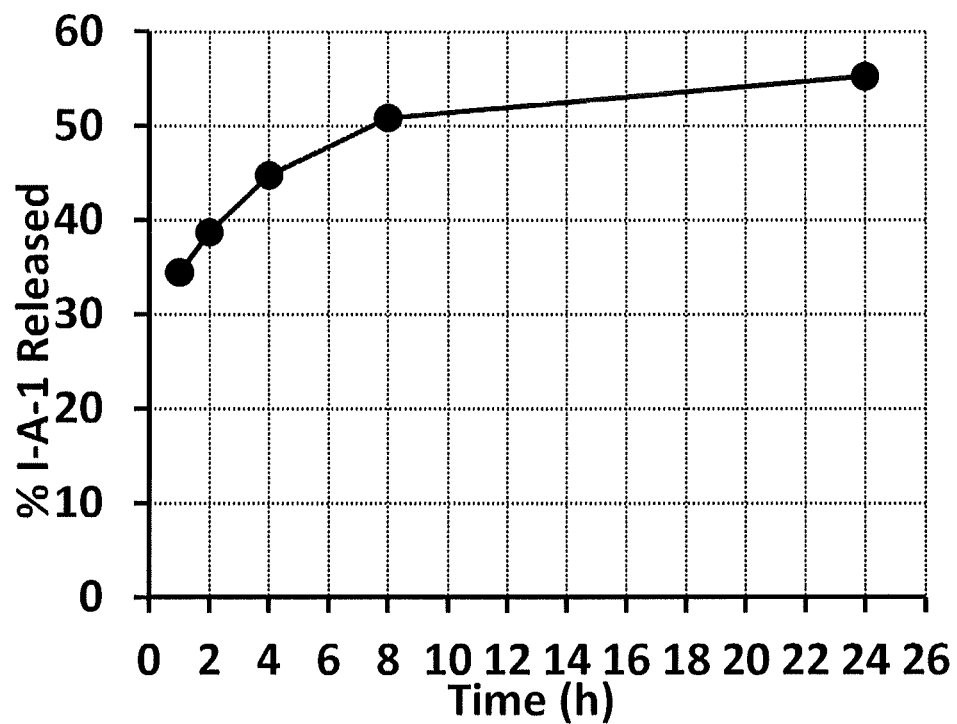
FIG. 6 shows the typical drug release profile of compound I-A-1 particles obtained by nanoprecipitation with polylactide (PLA) 100DL7A. Drug release data was obtained after incubation at 37° C. in PBS (pH 7.4) in the presence of 0.5% TWEEN 80.

A pharmaceutical agent described herein (e.g., a compound of the invention) may have a suitable solubility in the first and second solvents suitable for precipitation, such as a solubility in one or more ranges described herein for aqueous solubility or for solubility in a coating solution. A pharmaceutical agent having a relatively high solubility in the first solvent (e.g., an organic solvent) may be preferred. In certain embodiments, the pharmaceutical agent substantially or completely dissolves in the first solvent. A pharmaceutical agent having a relatively low solubility in the second solvent (e.g., water or a coating solution) may also be preferred. In certain embodiments, the solubility of the pharmaceutical agent in a mixture of the first and second solvents is lower than the solubility of the pharmaceutical agent in the first solvent. The relatively high solubility and relatively low solubility are as described herein. A pharmaceutical agent that has a relatively high solubility in the second solvent may be modified to form a prodrug of the pharmaceutical agent. The prodrug may have a relatively low solubility in the second solvent and still have a relatively high solubility in the first solvent and thus may be suitable for precipitation. Upon or after the particles or pharmaceutical compositions comprising the prodrug are administered to a subject, the prodrug may be converted and form or, in other words, "release," the pharmaceutical agent. For example, FIG. 6 shows a typical drug release profile of inventive particles that comprise compound I-A-1.

Precipitation by formation of a salt or complex may also be used to form particles comprised predominantly of a salt or complex of a pharmaceutical agent. In certain embodiments, the particles formed by this specific precipitation technique comprise predominantly of a pharmaceutical agent that is a nanocrystal. Generally, precipitation by formation of a salt or complex involves dissolving a pharmaceutical agent that is to form the core in a solvent, in the presence or absence of one or more excipients, followed by the addition of a counterion or a complexing agent, which forms a salt or a complex with the pharmaceutical agent to form the core. All counterions described herein are contemplated to be within the scope of the invention. This technique may be useful for preparing particles comprising pharmaceutical agents that have a relatively high solubility in the second solvent (e.g., water or a coating solution). In certain embodiments, the pharmaceutical agent has a relatively high solubility in the second solvent, and the salt or complex of the pharmaceutical agent has a relatively low solubility in the second solvent. The relatively high solubility and relatively low solubility are as described herein. In some embodiments, pharmaceutical agents having one or more charged or ionizable groups interact with a counterion (e.g., a cation or an anion) to form a salt or complex.

A variety of different acids may be used in a precipitation process involving formation of a salt or complex. Examples of acids suitable for precipitation include deconoic acid, hexanoic acid, mucic acid, octanoic acid. In other embodiments, a suitable acid may include acetic acid, adipic acid, L-ascorbic acid, L-aspartic acid, capric acid (decanoic acid), carbonic acid, citric acid, fumaric acid, galactaric acid, D-glucoheptonic acid, D-gluconic acid, D-glucuronic acid, glutamic acid, glutaric acid, glycerophosphoric acid, glycolic acid, hippuric acid, hydrochloric acid, DL-lactic acid, lauric acid, maleic acid, (−)-L-malic acid, palmitic acid, phosphoric acid, sebacic acid, stearic acid, succinic acid, sulfuric acid, (+)-L-tartaric acid, or thiocyanic acid. In other embodiments, a suitable acid may include alginic acid, benzenesulfonic acid, benzoic acid, (+)-camphoric acid, caprylic acid (octanoic acid), cyclamic acid, dodecylsulfuric acid, ethane-1,2-disulfonic acid, ethanesulfonic acid, ethanesulfonic acid, 2-hydroxy-, gentisic acid, glutaric acid, 2-oxo-, isobutyric acid, lactobionic acid, malonic acid, methanesulfonic acid, naphthalene-1,5-disulfonic acid, naphthalene-2-sulfonic acid, 2-naphthoic acid, 1-hydroxy-, nicotinic acid, oleic acid, orotic acid, oxalic acid, pamoic acid, (embonic acid), propionic acid, (−)-L-pyroglutamic acid, or p-toluenesulfonic acid. In yet other embodiments, a suitable acid may include acetic acid, 2,2-dichloro-, benzoic acid, 4-acetamido-, (+)-camphor-10-sulfonic acid, caproic acid (hexanoic acid), cinnamic acid, formic acid, hydrobromic acid, DL-mandelic acid, nitric acid, salicylic acid, salicylic acid, 4-amino-, and undecylenic acid (undec-10-enoic acid). Mixtures of two or more acids can also be used.

A variety of different bases may also be used in a precipitation process involving formation of a salt or complex. Examples of bases suitable for precipitation include ammonia, L-arginine, calcium hydroxide, choline, glucamine, N-methyl-, lysine, magnesium hydroxide, potassium hydroxide, or sodium hydroxide. In other embodiments, a suitable base may include benethamine, benzathine, betaine, deanol, diethylamine, ethanol, 2-(diethylamino)-, hydrabamine, morpholine, 4-(2-hydroxyethyl)-, pyrrolidine, 1-(2-hyroxyethyl)-, or tromethamine. In other embodiments, a suitable base may include diethanolamine (2,2'-iminobis (ethanol)), ethanolamine (2-aminoethanol), ethylenediamine, 1H-imidazole, piperazine, triethanolamine (2,2',2"-nitrilotris(ethanol)), and zinc hydroxide. Mixtures of two or more bases can also be used.

Examples of solvents suitable for precipitation involving formation of a salt or complex include the solvents described herein that may be used for milling. In some embodiments, the first or second solvent suitable for precipitation involving formation of a salt or complex is water, an aqueous solution (e.g., a buffered solution), an alcohol (e.g., methanol, ethanol, propanol, or butanol), or a mixture thereof, optionally including one or more other components, such as pharmaceutical excipients, polymers, and pharmaceutical agents.

The first or second solvent suitable for precipitation may include one or more surface-altering agents as described herein, and therefore, a coating comprising the one or more surface-altering agents may be formed around the core to provide the coated particles of the invention as they precipitate out of solution. The one or more surface-altering agents may be present in the first or second solvent at any suitable concentration, such as a concentration of at least about 0.001% (w/v), at least about 0.003% (w/v), at least about 0.01% (w/v), at least about 0.03% (w/v), at least about 0.1% (w/v), at least about 0.3% (w/v), at least about 1% (w/v), or at least about 3% (w/v). In some embodiments, the one or more surface-altering agents are present in the first or second solvent at a concentration of less than about 3% (w/v), less than about 1% (w/v), less than about 0.3% (w/v), less than about 0.1% (w/v), less than about 0.05% (w/v), less than about 0.01% (w/v), or less than about 0.003% (w/v). Combinations of the above-referenced ranges are also possible (e.g., a concentration of at least about 0.01 (w/v) and less than about 1% (w/v). Other ranges are also possible. In certain embodiments, the one or more surface-altering agents are present in the first solvent but absent in the second solvent. In certain embodiments, the one or more surface-altering agents are present in the second solvent but absent in the first solvent. In certain embodiments, the one or more surface-altering agents are present in both the first and second solvents.

Another exemplary method of forming the core and/or coated particle is a freeze-drying process or technique known in the art. See, e.g., U.S. Patent Application No. 61/738,949.

Other methods of forming core particles are also possible. For example, additional techniques of forming the core and/or coated particles include coacervation-phase separation, melt dispersion, interfacial deposition, in situ polymerization, self-assembly of macromolecules (e.g., formation of polyelectrolyte complexes or polyelectrolyte-surfactant complexes), spray-drying and spray-congealing, electrospray, air suspension coating, pan and spray coating, freeze-drying, air drying, vacuum drying, fluidized-bed drying, precipitation (e.g., nanoprecipitation, microprecipitation), critical fluid extraction, and lithographic approaches (e.g., soft lithography, step and flash imprint lithography, interference lithography, and photolithography). Combinations of the methods described herein are also possible. In some embodiments, a core of a pharmaceutical agent is first formed by precipitation, and then the size of the core is reduced by a milling process, optionally a coating is form on the core by the milling process.

Following the formation of the core of the particles including a pharmaceutical agent, the core may be optionally exposed to a solution comprising a (second) surface-altering agent that may associate with and/or coat the core. In embodiments in which the pharmaceutical agent already includes a coating of a first surface-altering agent, all or part of the first surface-altering agent may be exchanged with a second surface-altering agent. In some embodiments, the second surface-altering agent renders the particle mucus penetrating more than the first surface-altering agent does. In some embodiments, a particle having a coating including multiple surface-altering agents is formed (e.g., in a single layer or in multiple layers). In some embodiments, a particle having multiple coatings (e.g., each coating optionally comprising different surface-altering agents) may be formed. In some embodiments, the coating is in the form of a monolayer of a surface-altering agent. Other configurations are also possible.

In any of the methods described herein, a coating comprising a surface-altering agent may be formed on a core of the particles of the invention by incubating the core in a solution including the surface-altering agent for a period of at least about 1 minute, at least about 3 minutes, at least about 10 minutes, at least about 20 minutes, at least about 30 minutes, at least about 60 minutes, or more. In some cases, incubation may take place for a period of less than about 10 hours, less than about 3 hours, or less than about 60 minutes. Combinations of the above referenced ranges are also possible (e.g., an incubation period of less than 60 minutes and at least about 1 minute).

Methods of Treatment, Uses, and Administration

In addition to compounds, pharmaceutical compositions, and kits, the present invention also provides methods of delivering a pharmaceutical agent (e.g., a compound of the invention) to a subject. In certain embodiments, the pharmaceutical agent is delivered to a respiratory tract of the subject. In certain embodiments, the pharmaceutical agent is delivered to a target tissue of the respiratory tract of the subject.

The pharmaceutical agent may be delivered as it is, in a plurality of particles of the invention, or in a pharmaceutical composition of the invention, to the subject. In certain embodiments, the pharmaceutical agent is inhalationally delivered to a respiratory tract of the subject.

As described herein, prior to the invention, it has been challenging to deliver a pharmaceutical agent to a subject to treat and/or prevent a respiratory tract disease. Conventional delivery methods (e.g., oral, intravenous, and intramuscular) are inefficient, invasive, and/or inconvenient. Inhalational administration has been difficult. When dosed as a solution (e.g., by nebulizer) the pharmaceutical agent will typically be absorbed into systemic circulation, leaving limited local exposure in the lungs, which is the target tissue. In addition, conventionally formulated pharmaceutical agent delivered to the lungs will also be cleared due to the rapidly-clearing mucosal barrier (e.g., mucus) in the respiratory tract. The pharmaceutical agent in traditional pharmaceutical compositions often adheres to the mucus. Once immobilized in the mucus, the pharmaceutical agent is often quickly removed from the respiratory tract with the mucus in forms like snot or phlegm. Thus, for an effective amount of the pharmaceutical agent to be inhalationally delivered to the subject in conventional pharmaceutical compositions, high doses and/or frequent dosages may be used. However, high doses of a pharmaceutical agent increase the risk of local and systemic side effects. Moreover, frequent administration is not desirable because of its inconvenience to the subject, often resulting in poor compliance. Therefore, improving the mucus-penetration of the pharmaceutical agent by using appropriate pharmaceutical compositions, such as the inventive particles and pharmaceutical compositions of the invention, becomes advantageous.

In certain embodiments, the inventive methods of delivering a pharmaceutical agent involve inhalationally administering to a subject the inventive particles and/or pharmaceutical compositions that comprise a pharmaceutical agent. The particles or pharmaceutical compositions comprising the same of the invention may be mucus-penetrating. Without wishing to be bound by any particular theory, the particles comprising compounds of Formula (I) of the invention may be capable of avoiding adhesion to the mucus in the respiratory tract, quickly penetrating (e.g., diffusing through) the mucus, prolonging the retention or duration of the pharmaceutical agent in the respiratory tract, and/or increasing the local concentration of the pharmaceutical agent in the respiratory tract. The particles and/or pharmaceutical compositions may then be dissolved in a bodily fluid (e.g., blood or plasma) of a target tissue (e.g., a lung, trachea, or bronchus) of the respiratory tract and may release the pharmaceutical agent thereto. Therefore, the pharmaceutical agent is delivered to the target tissue of the respiratory tract. In contrast, none of the inhalable pharmaceutical compositions that have been marketed or are in late clinical development (e.g., TOBI®, CAYSTON®, TIP®, and ARIKACE®) benefit from the properties that are unique to mucus-penetrating particles and pharmaceutical compositions comprising the same.

In one embodiment, the invention provides a method of increasing the duration time of a compound of Formula (I) in the respiratory tract of a subject comprising locally administering a pharmaceutical composition comprising a plurality of particles comprising a core comprising a compound of Formula (I), or a pharmaceutically acceptable salt, solvate, hydrate, polymorph, co-crystal, tautomer, stereoisomer, and isotopically labeled derivative thereof, and a coating of a surface altering agent surrounding the core, wherein the surface altering agent is present on the outer surface of the core at a density of at least 0.01 surface altering agent per $nm^2$, and optionally one or more pharmaceutically acceptable excipients. In a certain embodiment, the particles are nanoparticles. In another embodiment, the particles are nanocrystals. In one embodiment, the composition is an inhalation solution locally administered by nebulizer. In another embodiment, the composition is an inhalable dry powder locally administered by dry powder inhaler.

In another embodiment, the invention provides a method of increasing the duration time of a compound of Formula (I-A-1) in the respiratory tract of a subject comprising locally administering a pharmaceutical composition comprising a plurality of particles comprising a core comprising a compound of Formula (I-A-1), or a pharmaceutically acceptable salt, solvate, hydrate, polymorph, co-crystal, tautomer, stereoisomer, and isotopically labeled derivative thereof, and a coating of a surface altering agent surrounding the core, wherein the surface altering agent is present on the outer surface of the core at a density of at least 0.01 surface altering agent per $n^2$, and optionally one or more pharmaceutically acceptable excipients. In a certain embodiment, the particles are nanoparticles. In another embodiment, the particles are nanocrystals. In one embodiment, the composition is an inhalation solution locally administered by nebulizer. In another embodiment, the composition is an inhalable dry powder locally administered by dry powder inhaler.

In another aspect, the present invention provides methods of treating and/or preventing a respiratory tract disease. In certain embodiments, the respiratory disease being treated and/or prevented by the inventive methods is a respiratory tract disease described herein. Other respiratory tract diseases known in the art are also contemplated as being within the scope of the invention. The inventive compounds, particles, and/or pharmaceutical compositions may be administered to a subject by various routes, such as orally in any acceptable form (e.g., tablet, liquid, capsule, powder, and the like), topically in any acceptable form (e.g., patch, drops, creams, gels, nebulization, punctal plug, drug eluting contact, iontophoresis, and ointments), by injection in any acceptable form (e.g., intravenous, intraperitoneal, intramuscular, subcutaneous, parenteral, and epidural), and by implant or the use of reservoirs (e.g., subcutaneous pump, intrathecal pump, suppository, biodegradable delivery system, non-biodegradable delivery system, and other implanted extended or slow release device or formulation). Preferably, the compounds, particles, and/or pharmaceutical compositions of the invention are inhalationally administered to the subject. The key benefits of inhalational administration may include non-invasive character, localized action with reduced systemic exposure, relative patient comfort, and ease of administration, Compliance of the subject is an issue which stems from a wide variety of factors, from patients' difficulty remembering to take pills, to trouble in physically administering injections, and to unpleasant side effects. Other issues include rapid clearance of the pharmaceutical agent and systemic exposure. Inhalational administration may address all of these issues.

Another aspect of the invention relates to methods of increasing the exposure of a pharmaceutical agent in a tissue of a respiratory tract of a subject.

Another aspect of the invention relates to methods of increasing the concentration of a pharmaceutical agent in a tissue of a respiratory tract of a subject.

In certain embodiments, the methods of the invention include administering to a subject a compound, particle, and/or pharmaceutical composition of the invention. In certain embodiments, the administration of the compound, particle, and/or pharmaceutical composition of the invention is an administration described herein. In certain embodiments, the administration is inhalational administration. In certain embodiments, an effective amount of the inventive compound, particle, and/or pharmaceutical composition is administered. In certain embodiments, the particle of the invention includes a pharmaceutical agent. In certain embodiments, the pharmaceutical composition of the invention includes a pharmaceutical agent.

In certain embodiments, the inventive compound, particle, and pharmaceutical composition are as described herein. In certain embodiments, the subject, pharmaceutical agent, effective amount, exposure, and concentration are as described herein.

The compounds, particles and/or pharmaceutical compositions of the invention may be administered to a subject in various forms of doses. For example, the compounds, particles, and/or pharmaceutical compositions of the invention may be administered in a single unit dose or repeatedly administered in a plurality of single unit doses. A unit dose is a discrete amount of the compounds, particles, and/or pharmaceutical compositions of the invention comprising a predetermined amount of a pharmaceutical agent. In some embodiments, fewer numbers of doses (e.g., ½, ⅓, or ¼ the number doses) are required using the particles of the invention having a mucus-penetrating coating compared to particles that do not have such a coating.

The exact amount of the compounds, particles, and/or pharmaceutical compositions of the invention required to achieve a therapeutically or prophylactically effective amount will vary from subject to subject, depending, for example, on species, age, and general condition of a subject, severity of the side effects or disorder, identity of the particular compound, mode of administration, and the like. The compounds, particles, and/or pharmaceutical compositions of the invention may be administered using repeated administrations where there is a period of time between consecutive doses. Repeated administration may be advantageous because it may allow the respiratory tract to be exposed to a therapeutically or prophylactically effective amount of a pharmaceutical agent for a period of time that is sufficiently long for the respiratory tract disease to be treated and/or prevented. In certain embodiments, the period of time between consecutive doses is less than about 1 hour, less than about 2 hours, less than about 6 hours, less than about 12 hours, less than about 36 hours, or less than about 48 hours. In certain embodiments, the period of time between consecutive doses is at least about 1 hour, at least about 2 hours, at least about 6 hours, at least about 12 hours, at least about 36 hours, or at least about 48 hours. Combinations of the above-referenced ranges are also possible (e.g., a period of time between consecutive doses of greater than or equal to about 2 hours and less than about 12 hours). Other ranges are also possible.

Delivery of the compounds, particles and/or pharmaceutical compositions of the invention to a subject may result in an efficacious level of a pharmaceutical agent (e.g., a compound of the invention) in a target tissue of a respiratory tract of the subject for an extended period of time after administration. An efficacious level of a pharmaceutical agent refers to an amount sufficient to elicit the desired biological response of the target tissue of the respiratory tract. As would be appreciated by those skilled in this art, the efficacious level of a pharmaceutical agent may vary depending on such factors as the desired biological endpoint, the pharmacokinetics of the pharmaceutical agent, the respiratory tract disease being treated, the mode of administration, and the age and health of the subject. In certain embodiments, the efficacious level of a pharmaceutical agent is an amount of the pharmaceutical agent, alone or in combination with other therapies, which provides a therapeutic benefit in the treatment of the respiratory disease. The efficacious level of a pharmaceutical agent can encompass a level that improves overall therapy, reduces or avoids symptoms or causes of the respiratory tract disease, or enhances the therapeutic efficacy of another therapeutic agent.

In some embodiments, an efficacious pharmaceutical agent level may be gauged, at least in part, by the maximum concentration ($C_{max}$) of the pharmaceutical agent in the target tissue after administration. In some cases, delivery of the compounds, particles, and/or pharmaceutical compositions comprising a pharmaceutical agent as described herein to an target tissue of the respiratory tract may result in a higher $C_{max}$ of the pharmaceutical agent in the target tissue of the respiratory tract after administration, compared to marketed compounds, particles, and pharmaceutical compositions at similar doses. In certain embodiments, the $C_{max}$ obtained from an administration of the compounds, particles, and/or pharmaceutical compositions of the invention is at least about 3%, at least about 10%, at least about 30%, at least about 100%, at least about 300%, at least about 1000%, or at least about 3000%, higher than the $C_{max}$ obtained from an administration of the marketed compounds, particles, and/or pharmaceutical compositions. In certain embodiments, the $C_{max}$ obtained from an administration of the compounds, particles, and/or pharmaceutical compositions of the invention is less than about 3000%, less than about 1000%, less than about 300%, less than about 100%, less than about 30%, less than about 10%, or less than about 3% higher than the $C_{max}$ obtained from an administration of the marketed compounds, particles, and/or pharmaceutical compositions. Combinations of the above-referenced ranges are also possible (e.g., an increase in $C_{max}$ at least about 30% and less than about 300%). Other ranges are also possible.

In some embodiments, the efficacious pharmaceutical agent levels are gauged, at least in part, by minimally efficacious concentrations of the pharmaceutical agent, e.g., $IC_{50}$ or $IC_{90}$, as known in the art.

In certain embodiments in which efficacious pharmaceutical agent levels (or $C_{max}$, $IC_{50}$, or $IC_{90}$) are present in the target tissue of the respiratory tract for an extended period of time after administration, the extended period of time after administration can range from hours to days. In certain embodiments, the extended period of time after administration is at least 1 hour, at least 2 hours, at least 6 hours, at least 12 hours, at least 1 day, at least 2 days, at least 3 days, at least 5 days, or at least 1 week. In certain embodiments, the extended period of time after administration is less than 1 week, less than 5 days, less than 3 days, less than 2 days, less than 1 day, less than 12 hours, less than 6 hours, less than 2 hours, less than 1 hour. Combinations of the above-referenced ranges are also possible (e.g., an extended period of time of at least about 4 hours and less than about 1 week). Other ranges are also possible.

In certain embodiments, the compounds, particles, and/or pharmaceutical compositions of the invention may be at dosage levels sufficient to deliver an effective amount of a pharmaceutical agent to a respiratory tract of a subject to obtain a desired therapeutic or prophylactic effect. In certain embodiments, an effective amount of a pharmaceutical agent that is delivered to a target tissue of the respiratory tract is at least about $10^{-3}$ ng/g, at least about $10^{-2}$ ng/g, at least about $10^{-1}$ ng/g, at least about 1 ng/g, at least about $10^{1}$ ng/g, at least about $10^{2}$ ng/g, at least about $10^{3}$ ng/g, or at least about $10^{4}$ ng/g of tissue weight. In certain embodiments, an effective amount of a pharmaceutical agent that is delivered to a target tissue of the respiratory tract is less than about $10^{4}$ ng/g, less than about $10^{3}$ ng/g, less than about $10^{2}$ ng/g, less than about $10^{1}$ ng/g, less than about 1 ng/g, less than about $10^{-1}$ ng/g, less than about $10^{-2}$ ng/g, or less than about $10^{-3}$ ng/g of tissue weight. Combinations of the above-referenced ranges are also possible (e.g., an effective amount of a pharmaceutical agent of at least about $10^{-2}$ ng/g and less than about $10^{3}$ ng/g of tissue weight). Other ranges are also possible.

It will be appreciated that dose ranges as described herein provide guidance for the administration of provided compounds, particles, and/or pharmaceutical compositions to an adult. The amount to be administered to, for example, a child or an adolescent can be determined by a medical practitioner or person skilled in the art and can be lower or the same as that administered to an adult.

These and other aspects of the present invention will be further appreciated upon consideration of the following Examples, which are intended to illustrate certain particular embodiments of the invention but are not intended to limit its scope, as defined by the claims.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Preparation of the Compounds

The compounds provided herein can be prepared from readily available starting materials using the following general methods and procedures. See, e.g., Scheme 1 below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

General processes for preparing compounds the invention, e.g., compound I-A-1, are provided as further embodiments of the invention and are illustrated in Scheme 1.

Scheme 1. Exemplary synthesis of compounds of the invention

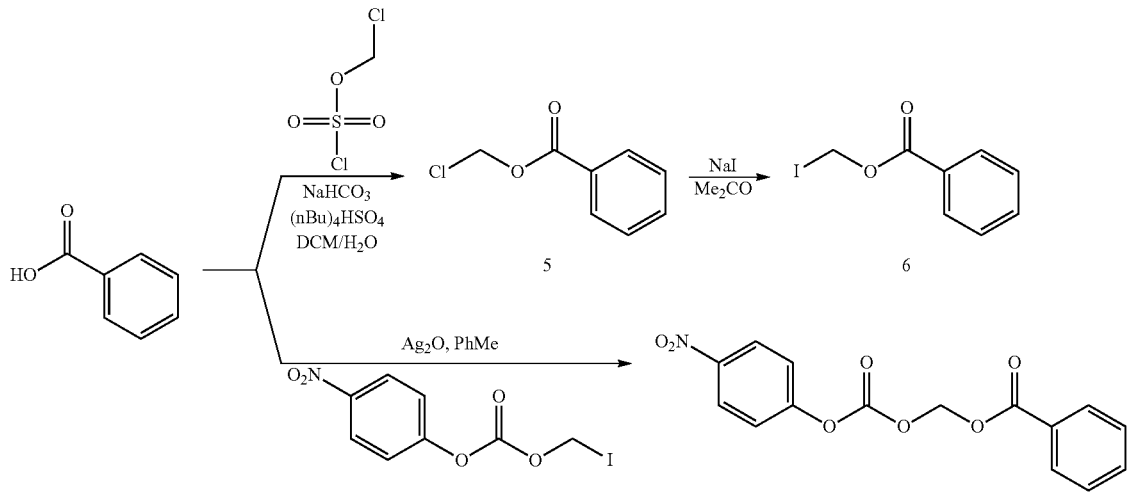

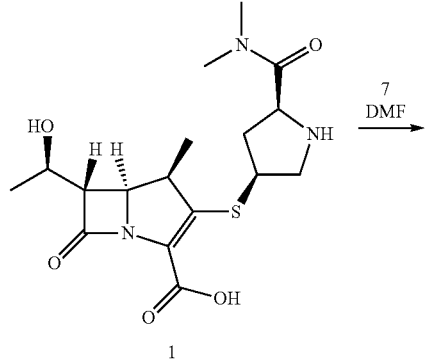 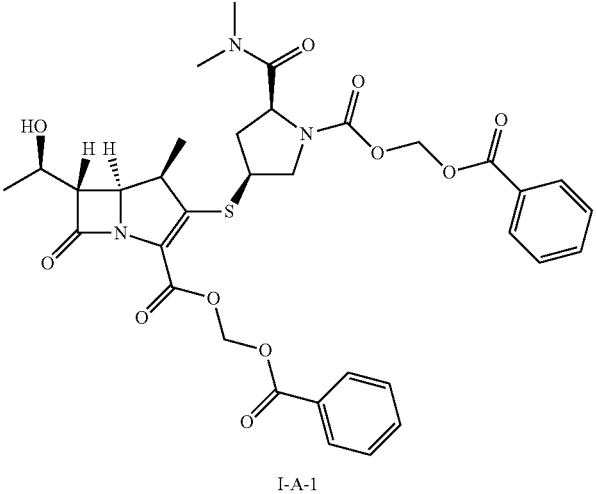

Preparation of Chloromethyl Benzoate (5)

Sodium benzoate (4.8 g 33.3 mmol), sodium bicarbonate (8.4 g 100.0 mmol) and tetrabutylammonium sulfate (1.1 g, 3.3 mmol) were dissolved in water (70 mL). Dichloromethane (70 mL) was added followed by chloromethyl chlorosulfonate (4.2 mL, 40.3 mmol). The resulting mixture (a biphasic solution) was vigorously stirred for 3 hours. The phases were separated. The organic phase was washed with water (2×50 mL) and dried over anhydrous magnesium sulfate. The solution was filtered through a small plug of silica (5 g) and evaporated under reduced pressure at <30° C. yielding compound 5 as colorless liquid (5.2 g, 92%). The analytical data for compound 5 were identical to those reported in literature (e.g., Baudy et al., J. Med. Chem. 2009, 52, 771).

Preparation of Iodomethyl Benzoate (6)

Compound 6 was prepared by a modification of a literature procedure (Maury et al., Org. Lett. 2010, 12, 3590). Chloromethyl benzoate (2.7 g, 15.9 mmol) was dissolved in acetone (20 mL). Sodium iodide (7.1 g, 47.6 mmol) was added, and the resulting mixture was stirred for 3 hours at 45° C., diluted with acetone (100 mL), filtered in the absence of light, and evaporated under reduced pressure at <30° C. The residue was dissolved in diethyl ether (100 mL), washed with aqueous sodium bicarbonate and aqueous sodium thiosulfate, dried over anhydrous magnesium sulfate, and evaporated under reduced pressure at <30° C. in the absence of light, yielding compound 6 as a yellow oil (3.3 g, 79%). The analytical data for compound 6 were identical to those reported in Maury et al., Org. Let. 2010, 12, 3590. Compound 6 was used immediately in the subsequent step.

Preparation of (benzoyloxy)methyl-4-nitrophenyl carbonate (7)

Iodomethyl-4-nitrophenyl carbonate (0.97 g, 3.0 mmol) was dissolved in toluene (20 mL). Benzoic acid (0.55 g, 4.5 mmol) and silver oxide (1.24 g, 5.36 mmol) were added. The resulting mixture was heated at 80° C. for 2 hours and filtered through silica pad with the aid of more toluene. Volatiles were evaporated under reduced pressure, yielding compound 7 as a yellow oil (0.89 g, 93%), which was used in the next reaction without further purification.

Preparation of (4R,5S,6S)-3-[[(3S,5S)-5-[(dimethylamino)carbonyl]-1-[[benzyloxymethoxy]carbonyl]-3-pyrrolidinyl]thio]-6-[(1R)-1-hydroxyethyl]-4-methyl-7-oxo-1-azabicyclo[3.2.0]hept-2-ene-2-carboxylic acid benzyloxymethyl ester (I-A-1)

Meropenem trihydrate (compound 1, 1.27 g, 2.90 mmol) was dissolved in dimethylformamide (20 mL). (Benzoyloxy)methyl-4-nitrophenyl carbonate (compound 7, 0.92 g, 2.90 mmol) was added as a solution in dimethylformamide (2 mL). The resulting mixture was stirred for 1 hour. Anhydrous sodium carbonate (0.62 g, 5.80 mmol) and iodomethyl benzoate (compound 6, 1.52 g, 5.80 mmol) were added. The reaction suspension was stirred for 1 hour. Ethyl acetate (200 mL) was added. The resulting mixture was washed with water (50 mL), aqueous saturated sodium bicarbonate (3×50 mL), and dried over anhydrous magnesium sulfate. Volatiles were evaporated under reduced pressure. The resulting residue was dissolved in dichloromethane (100 m L) and evaporated under reduced pressure. The resulting thick oil was dissolved in minimal amount of dichloromethane (about 5 mL) and poured into diethyl ether (200 mL) to precipitate the product. The precipitated semi-solid was filtered and dissolved in a mixture of ethyl acetate and acetone (4:1, 20 mL). The resulting solution was filtered through a silica pad (10 g) with the aid of additional solvent mixture (ethyl acetate and acetone (4:1)) as needed. Complete elution was assessed by TLC($R_f$ 0.7, same solvent system). Volatiles were evaporated under reduced pressure to yield a yellow solid (1.45 g), which was purified by preparative HPLC (ZORBAX $C_{18}$, 50 mm×250 mm) running on a gradient from 50:50 to 10:90 $H_2O$ (containing 0.1% formic acid)/ACN (containing 0.1% formic acid) in 10 minutes at a flow rate of 118 mL/min. The relevant fractions were neutralized with saturated $NaHCO_3$ solution (5 mL), and volatiles were evaporated under reduced pressure. A cloudy suspension resulted and was extracted with DCM. The layers were separated. The organic layer was dried over anhydrous $MgSO_4$ and evaporated under reduced pressure to dryness. The resulting residue was dried in vacuo to yield compound I-A-1 as a white solid (280 mg, 14%). $^1H$ NMR ($CDCl_3$): δ 8.04 (4H, m), 7.55 (2H, m), 7.42 (4H, m), 6.12 (1H, d), 6.08 (1H, d), 6.02 (1H, d), 5.89 (1H, d), 4.70 (1H, m), 4.21 (1H, m), 4.16 (1H, m), 4.09 (1H, m), 3.62 (1H, m), 3.42 (1H, m), 3.36 (1H, m), 3.18 (1H, m), 3.08 (3H, s), 3.02 (3H, s), 2.96 (3H, s), 2.81 (3H, s), 2.67 (1H, m), 1.88 (1H, m), 1.28 (3H, d), 1.12 (3H, d) ppm. $^{13}$C NMR (CDCl$_3$): δ 172.95, 172.87, 170.86, 170.65, 165.69, 165.63, 165.24, 159.65, 159.59, 152.65, 152.13, 150.98, 150.64, 133.92, 133.86, 130.33, 130.30, 130.23, 129.27, 129.25, 129.13, 128.75, 128.73, 128.71, 125.11, 125.04, 81.04, 80.42, 80.32, 80.30, 66.15, 66.12, 60.23, 60.16, 56.57, 56.47, 56.28, 55.90, 54.82, 54.46, 44.35, 40.95, 40.25, 37.25, 37.10, 36.40, 36.22, 35.93, 35.32, 22.00, 21.96, 17.29 ppm. LC-MS: m/z (Me) calculated 695.7. found 696.2. Compound I-A-1 crystallized from MeOH/H$_2$O (2:1, 5 mg/mL total concentration) or ethyl acetate/methyl t-butyl ether (1:1, 40 mg/mL total concentration) yielded crystals that were suitable for the pharmaceutical composition of the invention.

Example 2. Conversion of Compound I-A-1 to Meropenem

Figure 5:
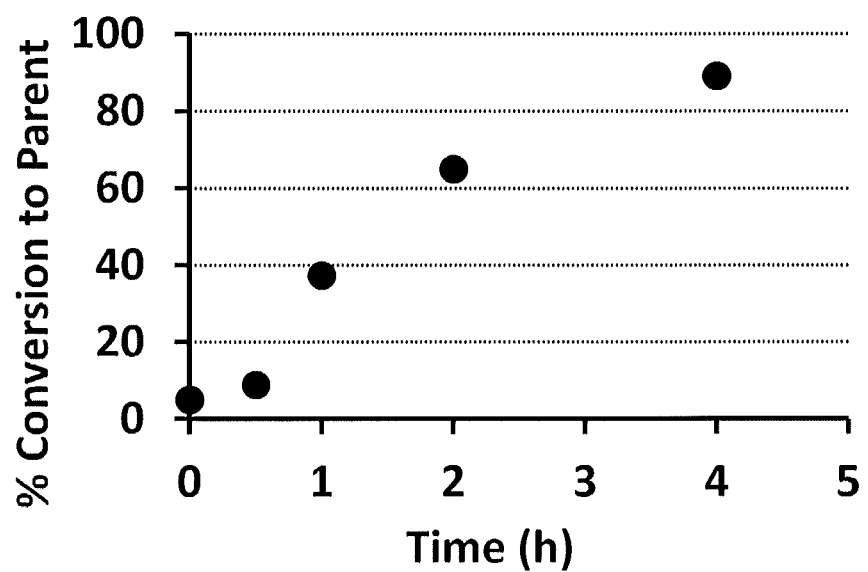
FIG. 5 shows that compound I-A-1 is converted into meropenem after incubation at 37° C. in mucus from a cystic fibrosis (CF) patient.

Compound I-A-1 was suspended in homogenized CF sputum (CFS) at a concentration of 20 µg/mL (99.5:0.5 CFS/DMSO, 1.2 mL total volume) and incubated at 37° C. Aliquots (0.2 mL) taken after 0, 0.5, 1, 2 and 4 h of incubation were stored at −80° C. prior to bio-analytical processing. After a series of extractions in organic solvents, the resulting free meropenem was quantified by tandem mass spectrometry (FIG. 5).

Example 3. Milling of Compound I-A-1

Figure 3:
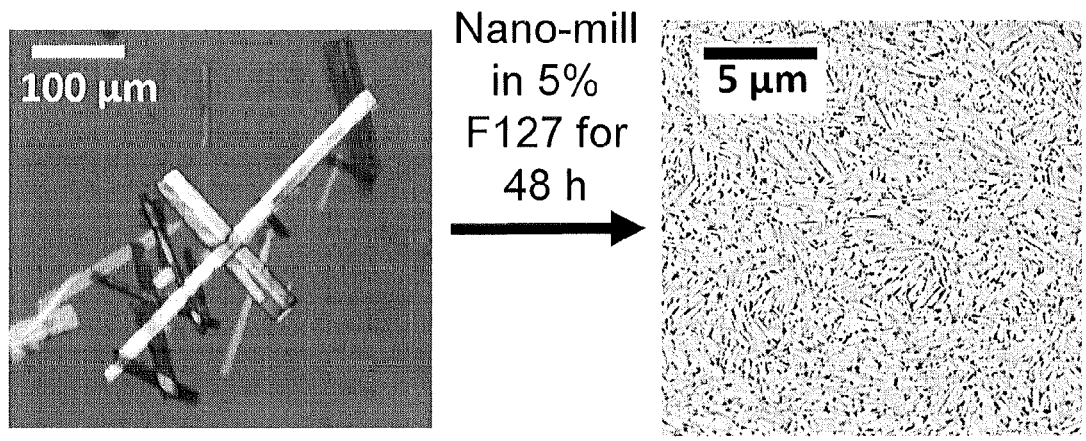
FIG. 3 shows polarized microscopy and SEM images of compound I-A-1, a crystalline compound, before and after milling.

The following describes a non-limiting example of forming MPPs using a core comprising compound I-A-1. Coarse crystals of compound I-A-1 were nanomilled in an aqueous dispersion containing PLURONIC® F127 in the presence of milling media until the average particle size of compound I-A-1 was reduced to below 500 nm as measured by dynamic light scattering (DLS). PLURONIC® F127 was used as a stabilizer that (1) aided particle size reduction to several hundreds of nanometers and (2) physically (i.e., non-covalently) coated the surface of generated nanoparticles with a mucoinert coating that would minimize particle interactions with mucus constituents and prevent mucus adhesion. This process produced physically stable nanosuspensions of particles (FIG. 3). In one experiment, the particles in the nanosuspensions had a Z-average particle diameter of 260 nm and polydispersity index of 0.109, as measured by DLS.

Example 4. Mobility of Compound I-A-1 in Mucus Measured by Dark-Field Microscopy Fresh undiluted human cervicovaginal mucus (CVM) was contacted with the particles of the invention, such as ones described in Example 3. The mobility of compound I-A-1 in CVM was characterized by dark-field microscopy using a CYTOVIVA® High Resolution Illumination System, which allows visualization of fluorescent and non-fluorescent nano-sized objects. In one experiment, 0.5 µL of the nanosuspension was added to 20 µL of undiluted CVM that was pre-deposited into a 20-µL well on a microscope slide. Using a CCD camera, 15-s movies were captured at a temporal resolution of 66.7 ms (i.e., 15 frames/s) under 100× magnification from several randomly selected areas within each sample. Mobility of the particles in the movies was scored on a scale from 0 to 3 in order of increasing mobility, in a single-blind experiment by independent observers. The scoring criterion is as follows: 0-0.5 immobile; 0.51-1.5 slightly mobile; 1.51-2.5 moderately mobile; and 2.51-3.0 very mobile. The average mobility score for the particles was 3.0, as calculated from 6 independent observations.

Example 5. Mobility of Compound I-A-1 in Mucus Measured by Bulk Transport

Figure 4:
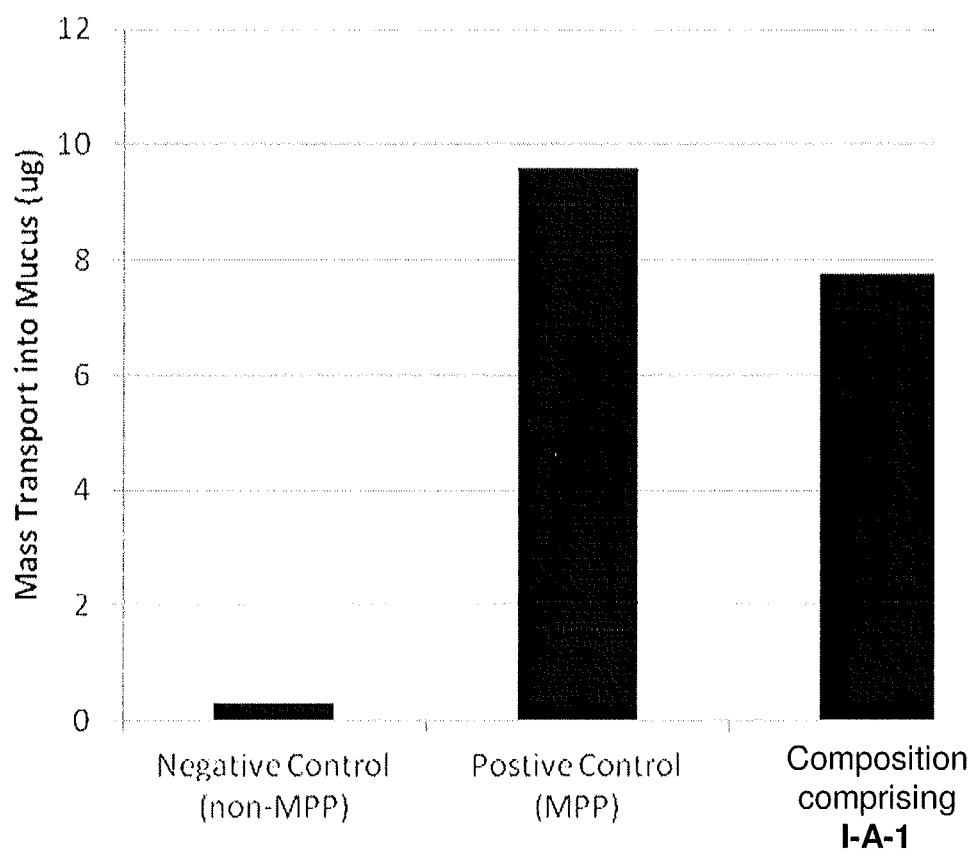
FIG. 4 shows mass transport data demonstrating the mobility of compound I-A-1 in diluted cervicovaginal mucus.

The ability of the particles of the invention, such as ones described in Example 3, to penetrate mucus was measured via the mass transport of the particles into a mucus sample. In this method, 20 µL of fresh undiluted human cervicovaginal mucus (CVM) was collected in a capillary tube, and one end of the capillary tube was sealed with clay. The open end of the capillary tube was submerged in 20 µL of an aqueous suspension of the particles where the concentration of compound I-A-1 was 0.5% w/v. After a desired time, typically 18 hours, the capillary tube was removed from the suspension, and the outside of the capillary tube was wiped clean. The capillary tube containing the mucus sample was placed in an ultracentrifuge tube. Extraction media was added to the ultracentrifuge tube, and the ultracentrifuge tube was incubated for 1 hour while mixing, which removed the mucus from the capillary tube and extracted compound I-A-1 from the mucus. The ultracentrifuge tube was spun to remove mucins and other non-soluble components. The amount of compound I-A-1 in the extracted sample was quantified using HPLC (FIG. 4, the negative control was uncoated 200 nm polystyrene (PS) spheres with carboxylic acid groups on the surface. The positive control was the same PS spheres coated with PLURONIC® F127). The results were in good agreement with those obtained by the dark-field microscopy method, such as the one described in Example 4, showing clear differentiation in transport between mucus-penetrating particles (MPPs) and conventional particles (CPs).

Example 6. Preparation of MPPs Comprising Compound I-A-1 by Nanoprecipitation

The following describes a non-limiting example of a method of preparing MPPs comprising compound I-A-1 by a nanoprecipitation process in the presence of PLURONIC® F127. Polylactide (PLA), a biodegradable pharmaceutically relevant polymer was used as a material to form the cores of the particles via nanoprecipitation. PLURONIC® F127 acted as a nanosuspension stabilizer and surface-altering agent forming coatings around the produced cores.

A solution of compound I-A-1 and PLA in a water-miscible organic solvent capable of dissolving both compound I-A-1 and PLA (e.g., acetone) was added into an aqueous solution of PLURONIC® F127 under mixing, resulting in the formation of a fine precipitate of nanoparticles containing both compound I-A-1 and PLA. In this process, the PLURONIC® (1) acted as an surfactant that forms a stabilizing coating around the precipitated organic phase that, upon solidification, form the cores; and (2) physically (i.e., non-covalently) coated the surface of generated nanoparticles with a muco-inert coating that would lead to rapid particle penetration in mucus.

A typical nanoprecipitation process is as follows: an acetone solution (about 1 ML) containing 10-20 mg/mL of compound I-A-1 and 5 mg/ml of PLA (polylactide grade 100DL7A, purchased from SURMODICS) was added under stirring at a rate of 0.5 mL/min into an aqueous solution of PLURONIC® F127 (about 40 mL, 5 wt %). The resulting nanosuspension was allowed to equilibrate overnight at room temperature to evaporate the volatiles and crystallize out unencapsulated compound I-A-1. The nanosuspension was filtered through 1 micron glass fiber filters to remove any agglomerates and/or crystals of unencapsulated compound I-A-1. The filtrate was centrifuged to sediment the nanoparticles. The obtained sediment was separated from the supernatant and washed by resuspending in an aqueous solution containing 0.5 wt % PLURONIC® F127. This sedimentation-resuspension procedure was repeated to ensure removal of unencapsulated compound I-A-1. The final product was freeze-dried for storage.

Example 7. Preparation of Compounds 8-19

General processes for preparing compounds the invention, e.g., compounds 12-19, are provided as further embodiments of the invention and are illustrated in Scheme 2.

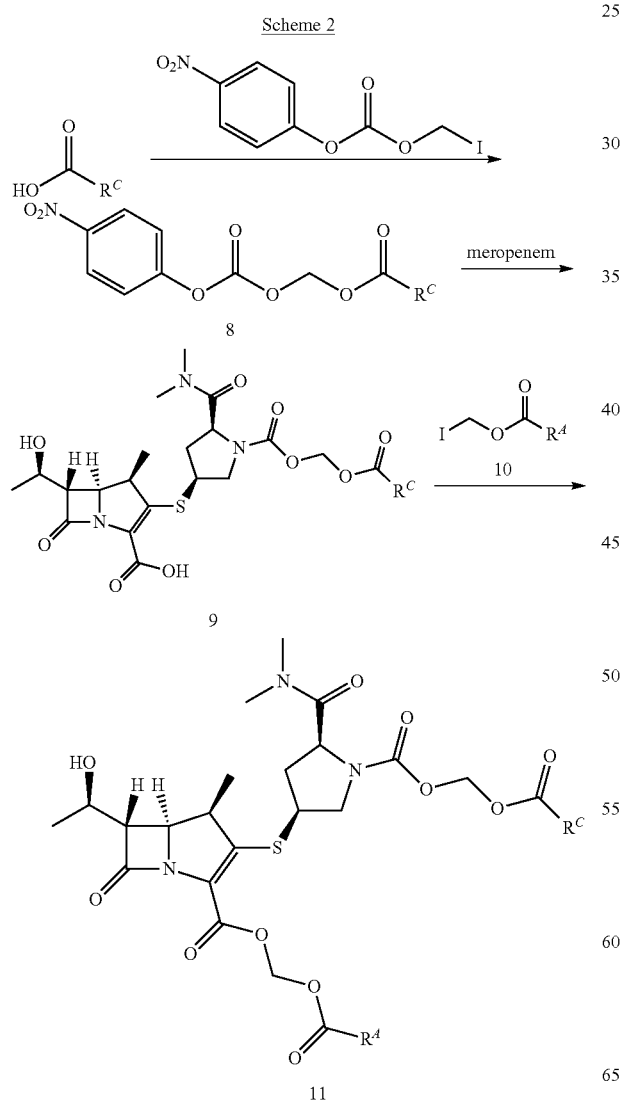

TABLE 3

Description of $R^1$ and $R^2$ in Compounds I-A-1 and 12-19

| Compound | $R^A$ | $R^C$ |
|---|---|---|
| I-A-1 | phenyl | phenyl |
| 12 | n-propyl | phenyl |
| 13 | phenyl | n-propyl |
| 14 | phenyl | cyclobutyl |
| 15 | n-propyl | cyclobutyl |
| 16 | 4-fluorophenyl | 4-fluorophenyl |
| 17 | 4-chlorophenyl | 4-chlorophenyl |
| 18 | 3-fluorophenyl | 3-fluorophenyl |
| 19 | 3-chlorophenyl | 3-chlorophenyl |

Preparation of (alkyloxy)methyl-4-nitrophenyl and (aryloxy)methyl-4-nitrophenyl carbonates (8)

Iodomethyl-4-nitrophenyl carbonate (1 equiv) and (alkyloxy)methyl-4-nitrophenyl or (aryloxy)methyl-4-nitrophenyl carbonate 8 (1 equiv) were dissolved in solvent, Solid Ag$_2$O (1 equiv) was added in a single portion and the reaction stirred at room temperature. Slurry was filtered through CELITE and the solvent evaporated. Resulting product residue was used directly in the next reaction.

Preparation of Carbamate Derivatives of Meropenem (9)

Meropenem trihydrate (1 equiv) and the appropriate activated carbonate of formula 8 (1 equiv) were dissolved in anhydrous DMF and stirred at room temperature. The reaction solution was used directly in the next step.

Preparation of Iodomethyl Benzoate Derivatives and Iodomethyl Alkylcarboxylate Derivatives (10)

Compounds of formula 10 were prepared as reported by Harada, N., et al. *Synth. Comm.* 1994, 24, 767, using the appropriate carboxylic acid.

Preparation of Meropenem Prodrugs (11)

The appropriate iodomethyl derivative of 10 (2 equiv) and solid Na$_2$CO$_3$ (2 equiv) were added to the solution of meropenem carbamate 9 and stirred at room temperature. Solution was diluted with water, then extracted three times with ethyl acetate. Combined extracts were dried over MgSO$_4$, filtered, and the solvent evaporated. Product residues were purified first by flash chromatography, then by preparative HPLC. Analytical data for Compounds 12-19 are set forth below.

Compound 12: (4R,5S,6S)-(butyryloxy)methyl 3-(((3S,5S)-1-(((benzoyloxy)methoxy)carbonyl)-5-(dimethylcarbamoyl)pyrrolidin-3-yl)thio)-6-((R)-1-hydroxyethyl)-4-methyl-7-oxo-1-azabicyclo[3.2.0]hept-2-ene-2-carboxylate White solid, m/z: 662 (M+1). Spectral data given for the mixture of rotamers. $^1$H-NMR (CDCl$_3$): δ 0.92 (dd, J=7.5, 7.5 Hz, 3H); 1.21 (dd, J=2.0, 7.5 Hz, 3H); 1.29 (d, J=6.5 Hz, 3H); 1.60 (m, 2H); 1.85-1.93 (m, 1H); 2.31 (dd, J=7.0, 7.0 Hz, 2H); 2.61-2.78 (m, 2H); 2.82 (s, 1.5H); 2.97 (s, 1.5H); 3.04 (s, 1.5H); 3.09 (s, 1.5H); 3.17-3.20 (m, 1H); 3.32-3.45 (m, 2H); 3.58-3.66 (m, 1H), 4.05-4.24 (m, 3H); 4.68-4.75 (m, 1H); 5.81 (dd, J=1.0, 6.0 Hz, 1H); 5.87-5.91 (m, 2.5H); 6.02 (d, J=6.5 Hz, 0.5H); 7.43 (dd, J=7.5, 7.5 Hz, 2H); 7.57 (dd, J=7.5, 7.5 Hz, 1H); 8.01-8.07 (m, 2H).

$^{13}$C-NMR (CDCl$_3$): δ 13.48; 17.00; 17.02; 17.97; 21.70; 21.74; 26.90; 34.97; 35.62; 35.68; 35.92; 36.10; 36.81; 36.96; 39.94; 40.62; 44.02; 49.37; 54.23; 54.56; 55.59; 55.96; 56.18; 56.27; 59.87; 59.94; 65.89; 65.92; 72.74; 79.39; 80.11; 80.72; 124.89; 124.92; 128.44; 128.95; 128.97; 129.93; 130.01; 133.62; 149.94; 150.26; 151.82; 152.34; 159.21; 159.27; 165.33; 165.38; 170.32; 170.53; 172.03; 172.47; 172.55.

Compound 13: (4R,5S,6S)-(benzoyloxy)methyl 3-(((3S,5S)-1-(((butyryloxy)methoxy)carbonyl)-5-(dimethylcarbamoyl)pyrrolidin-3-yl)thio)-6-((R)-1-hydroxyethyl)-4-methyl-7-oxo-1-azabicyclo[3.2.0]hept-2-ene-2-carboxylate White solid, Spectral data given for the mixture of rotamers. $^1$H-NMR (CDCl$_3$): δ 0.92 (dd, J=7.0, 7.0 Hz, 3H), 1.22 (dd, J=7.0, 9.0 Hz, 3H); 1.30 (dd, J=6.0, 6.0 Hz, 3H); 1.58-1.66 (m, 2H); 1.86-1.94 (m, 1H); 2.27-2.35 (m, 2H); 2.58-2.86 (m, 2H); 2.92 (s, 1.5H); 2.95 (s, 1.5H); 3.03 (s, 1.5H); 3.07 (s, 1.5H); 3.17 (m, 1H); 3.32-3.42 (m, 2H); 3.58-3.67 (m, 1H); 3.99-4.13 (m, 1H); 4.15-4.24 (m, 2H); 4.69 (ddd, J=8.0, 8.0, 25.5 Hz, 1H); 5.60-5.66 (m, 1.5H); 5.77 (d, J=6.0 Hz, 0.5H); 6.11 (ddd, J=2.0, 6.0, 14.0 Hz, 2H); 7.40-7.45 (m, 2H); 7.53-7.58 (m, 1H); 8.03-8.06 (m, 2H).

$^{13}$C-NMR (CDCl$_3$): δ 13.47; 13.50; 17.00; 17.92; 17.99; 21.69; 21.76; 35.08; 35.67; 35.74; 35.76; 36.09; 36.80; 36.96; 39.97; 40.79; 44.06; 44.12; 54.09; 54.51; 55.60; 55.89; 56.17; 56.26; 59.86; 59.91; 65.84; 65.88; 80.01; 79.37; 80.02; 80.21; 124.79; 124.95; 128.41; 128.83; 130.03; 133.57; 150.23; 150.60; 151.89; 152.37; 159.27; 159.34; 164.93; 170.32; 170.49; 172.45; 172.52; 172.54; 172.55.

Compound 14: (4R,5S,6S)-(benzoyloxy)methyl 3-(((3S,5S)-1-(((((cyclobutanecarbonyl)oxy)methoxy)carbonyl)-5-(dimethylcarbamoyl)pyrrolidin-3-yl)thio)-6-((R)-1-hydroxyethyl)-4-methyl-7-oxo-1-azabicyclo[3.2.0]hept-2-ene-2-carboxylate White solid, m/z: 674 (M+1). Spectral data given for the mixture of rotamers. $^1$H-NMR (CDCl$_3$): δ 1.19-1.23 (m, 3H); 1.30 (dd, J=6.5, 6.5 Hz, 3H); 1.83-1.99 (m, 3H); 2.14-2.32 (m, 4H); 2.64-2.70 (m, 1H); 2.92 (s, 1.5H); 2.95 (s, 1.5H); 3.04 (s, 1.5H); 3.07 (s, 1.5H); 3.11-3.22 (m, 2H); 3.32-3.43 (m, 2H); 3.59-3.67 (m, 1H); 3.99-4.12 (m, 1H); 4.15-4.25 (m, 2H); 4.69 (ddd, J=8.5, 8.5, 23.0 Hz, 1H); 5.61-5.66 (m, 1.5H); 5.76 (d, J=5.5 Hz, 0.5H); 6.11 (ddd, J=2.0, 5.5, 19.0 Hz, 2H); 7.40-7.45 (m, 2H); 7.58 (m, 1H); 8.02-8.07 (m, 2H).

$^{13}$C-NMR (CDCl$_3$): δ 17.00; 18.23; 18.24; 21.67; 21.73; 24.87; 24.92; 24.95; 25.01; 35.09; 35.69; 35.98; 36.11; 36.83; 36.97; 37.58; 37.63; 39.99; 40.78; 44.07; 44.13; 54.07; 54.48; 55.58; 55.90; 56.18; 56.26; 59.85; 59.91; 65.85; 65.89; 76.73; 76.99; 77.25; 79.49; 80.01; 80.39; 124.78; 124.92; 128.41; 128.83; 130.02; 133.56; 150.28; 150.62; 151.88; 152.39; 159.27; 159.33; 164.94; 170.38; 170.53; 172.56; 172.59; 174.26; 174.29.

Compound 15: (4R,5S,6S)-(butyryloxy)methyl 3-(((3S,5S)-1-(((((cyclobutanecarbonyl)oxy)methoxy)carbonyl)-5-(dimethylcarbamoyl)pyrrolidin-3-yl)thio)-6-((R)-1-hydroxyethyl)-4-methyl-7-oxo-1-azabicyclo[3.2.0]hept-2-ene-2-carboxylate White solid, m/z: 640 (M+1). Spectral data given for the mixture of rotamers. $^1$H-NMR (CDCl$_3$): δ 0.93 (dd, J=7.0, 7.0 Hz, 3H), 1.24 (dd, J=7.5, 7.5 Hz, 3H); 1.32 (dd, J=6.0, 6.0 Hz, 3H); 1.61-1.68 (m, 2H); 1.84-2.00 (m, 3H); 2.15-2.31 (m, 4H); 2.34 (dd, J=6.5, 6.5 Hz, 31-1); 2.65-2.71 (m, 1H); 2.93 (s, 1.5H); 2.96 (s, 1.5H); 3.05 (s, 1.5H); 3.09 (s, 1.5H); 3.13-3.23 (m, 2H); 3.33-3.42 (m, 2H); 3.58-3.67 (m, 1H); 4.07 (ddd, J=7.0, 11.0, 42.5 Hz, 1H); 4.17-4.25 (m, 2H); 4.7 (ddd, J=8.0, 8.0, 23.0 Hz, 1H); 5.62-5.67 (m, 1.5H); 5.77 (d, J=6.0 Hz, 0.5H); 5.83 (d, J=9.0 Hz, 1H); 5.90 (d, J=5.5 Hz, 1H).

$^{13}$C-NMR (CDCl$_3$): δ 13.46; 17.03; 17.98; 18.25; 18.28; 21.73; 21.78; 24.90; 24.94; 24.97; 25.04; 35.08; 35.69; 35.98; 36.11; 36.84; 36.99; 37.61; 37.66; 40.01; 40.77; 44.06; 44.11; 54.15; 54.54; 55.57; 55.88; 56.20; 56.26; 59.88; 59.94; 65.90; 65.97; 79.40; 79.41; 79.50; 80.39; 124.96; 125.05; 149.95; 150.23; 151.90; 152.40; 159.22; 159.27; 170.36; 170.50; 172.06; 172.49; 174.28; 174.30.

Compound 16: (4R,5S,6S)-((4-fluorobenzoyl)oxy)methyl 3-(((3S,5S)-5-(dimethylcarbamoyl)-1-(((((4-fluorobenzoyl)oxy)methoxy)carbonyl)pyrrolidin-3-yl)thio)-6-((R)-1-hydroxyethyl)-4-methyl-7-oxo-1-azabicyclo[3.2.0]hept-2-ene-2-carboxylate White solid, m/z: 732 (M+1). Spectral data given for the mixture of rotamers. $^1$H-NMR (CDCl$_3$): δ 1.21 (dd, J=3.0, 6.6 Hz, 3H); 1.29 (dd, J=3.0, 6.6 Hz, 3H); 1.85-1.93 (m, 11H); 2.64-2.71 (in, 1.5H); 2.78-2.83 (m, 0.5H); 2.81 (s, 1.5H); 2.97 (s, 1.5H); 3.03 (s, 1.5H); 3.08 (s, 1.5H); 3.17-

3.21 (m, 2H); 3.32-3.45 (m, 2H); 3.58-3.67 (m, 1H); 4.03-4.25 (m, 2H); 4.71 (ddd, J=8.5, 8.5, 21.5 Hz, 1H); 5.87-5.91 (m, 1.5H); 5.90 (d, J=5.5 Hz, 0.5H); 6.06 (d, J=5.5 Hz, 1H); 6.11 (d, J=5.5 Hz, 1H); 7.06-7.14 (m, 4H); 8.02-8.10 (m, 4H).

$^{13}$C-NMR (CDCl$_3$): δ 17.01; 21.72; 21.78; 26.91; 35.01; 35.62; 35.91; 36.11; 36.79; 36.95; 39.96; 40.68; 44.05; 49.37; 54.18; 54.56; 55.64; 55.99; 56.18; 56.23; 59.89; 59.96; 55.99; 65.82; 65.90; 72.77; 80.01; 80.09; 80.75; 115.55; 115.59; 115.67; 115.73; 115.77; 124.87; 124.91; 125.10; 125.13; 125.21; 125.23; 125.26; 125.28; 132.55; 132.64; 132.67; 132.71; 132.74; 150.19; 150.47; 151.83; 152.32; 159.24; 159.29; 163.95; 164.35; 164.44; 165.07; 167.10; 170.29; 170.33; 170.44; 172.55; 172.60; 172.63.

Compound 17: (4R,5S,6S)-((4-chlorobenzoyl)oxy)methyl 3-(((3S,5S)-1-((((4-chlorobenzoyl)oxy)methoxy)carbonyl)-5-(dimethylcarbamoyl)pyrrolidin-3-yl)thio)-6-((R)-1-hydroxyethyl)-4-methyl-7-oxo-1-azabicyclo[3.2.0]hept-2-ene-2-carboxylate White solid, m/z: 764 (M). Spectral data given for the mixture of rotamers. $^1$H-NMR (CDCl$_3$): δ 1.20 (dd, J=6.5, 6.5 Hz, 3H); 1.27 (dd, J=6.5, 6.5 Hz, 3H); 1.83-1.92 (nm, 1H); 2.64-2.71 (m, 2H); 2.81 (s, 1.5H); 2.96 (s, 1.5H); 3.02 (s, 1.5H); 3.08 (s, 1.5H); 3.16-3.19 (m, 1H); 3.32-3.44 (m, 2H); 3.58-3.66 (m, 1H); 4.03-4.24 (m, 3H); 4.71 (ddd, J=7.5, 7.5, 22.0 Hz, 1H); 5.86-5.89 (m, 1.5H); 5.98 (d, J=5.5 Hz, 0.5H); 6.04 (d, J=5.5 Hz, 1H); 6.11 (d, J=5.5 Hz, 1H); 7.37-7.41 (m, 4H); 7.95-7.98 (m, 4H).

$^{13}$C-NMR (CDCl$_3$): δ 16.99; 21.65; 21.72; 34.95; 35.55; 35.90; 36.09; 36.76; 36.93; 39.86; 40.60; 44.01; 54.18; 54.56; 55.65; 55.99; 56.13; 56.20; 59.89; 59.94; 65.73; 65.78; 80.01; 80.03; 80.13; 80.79; 124.7; 124.77; 127.27; 127.36; 127.43; 128.76; 128.79; 131.28; 131.36; 131.39; 140.03; 140.08; 140.10; 150.31; 150.61; 151.77; 152.25; 159.18; 159.24; 164.07; 164.46; 164.54; 170.27; 170.43; 172.62; 172.68.

Compound 18: (4R,5S,6S)-((3-fluorobenzoyl)oxy)methyl 3-(((3S,5S)-5-(dimethylcarbamoyl)-1-((((3-fluorobenzoyl)oxy)methoxy)carbonyl)pyrrolidin-3-yl)thio)-6-((R)-1-hydroxyethyl)-4-methyl-7-oxo-1-azabicyclo[3.2.0]hept-2-ene-2-carboxylate White solid, m/z: 732 (M+1). Spectral data given for the mixture of rotamers. $^1$H-NMR (CDCl$_3$): δ 1.21 (dd, J=7.0 Hz, 3H); 1.28 (dd, J=2.0, 6.0 Hz, 3H); 1.28-1.95 (m, 1H); 2.65-2.71 (m, 1H); 2.84 (s, 1.5H); 2.97 (s, 1.5H); 3.04 (s, 1.5H); 3.10 (s, 1.5H); 3.18 (ddd, J=2.0, 7.0, 7.0 Hz, 1H); 3.33-3.46 (m, 2H); 3.60-3.68 (m, 1H); 4.04-4.24 (m, 3H); 4.72 (ddd, J=8.0, 8.0, 21.5 Hz, 1H); 5.86-5.89 (m, 2H); 6.01 (d, J=5.5 Hz, 1H); 6.07 (d, J=5.5 Hz, 1H); 6.12 (d, J=5.5 Hz, 1H); 7.23-7.29 (m, 2H); 7.38-7.44 (m, 2H); 7.69-7.73 (m, 2H); 7.82-7.86 (m, 2H).

$^{13}$C-NMR (CDCl$_3$): δ 17.02; 21.68; 21.74; 35.01; 35.60; 35.94; 36.11; 36.12; 36.79; 36.95; 39.93; 40.67; 44.07; 54.18; 54.56; 55.69; 56.01; 56.16; 56.26; 59.89; 59.95; 65.81; 65.85; 80.12; 80.26; 80.90; 116.65; 116.73; 116.76; 116.83; 116.89; 116.91; 116.92; 116.95; 120.58; 120.61; 120.75; 120.78; 124.70; 124.77; 125.70; 125.72; 125.76; 125.80; 125.82; 130.10; 130.14; 130.16; 130.20; 130.95; 131.01; 131.08; 131.13; 131.18; 150.43; 150.75; 151.75; 152.24; 159.19; 159.25; 161.41; 161.44; 163.38; 163.40; 163.82; 163.85; 164.20; 164.29; 164.30; 164,31; 170.28; 170.31; 170.44; 172.56; 172.62; 172.65.

Compound 19: (4R,5S,6S)-((3-chlorobenzoyl)oxy)methyl 3-(((3S,5S)-1-((((3-chlorobenzoyl)oxy)methoxy)carbonyl)-5-(dimethylcarbamoyl)pyrrolidin-3-yl)thio)-6-((R)-1-hydroxyethyl)-4-methyl-7-oxo-1-azabicyclo[3.2.0]hept-2-ene-2-carboxylate Pale yellow solid, m/z: 764 (M). Spectral data given for the mixture of rotamers. $^1$H-NMR (CDCl$_3$): δ 1.11 (dd, J=7.0, 7.0 Hz, 3H); 1.18 (dd, J=2.0, 6.0 Hz, 3H); 1.75-1.84 (m, 1H); 2.44-2.65 (m, 2H); 2.75 (s, 1.5H); 2.87 (s, 1.5H); 2.94 (s, 1.5H); 2.99 (s, 1.5H); 3.08 (ddd, J=2.5, 8.0, 8.0 Hz, 1H); 3.23-3.36 (m, 2H); 3.50-3.56 (m, 1H); 3.95-4.14 (m, 3H); 4.62 (ddd, J=8.0, 8.0, 23.0 Hz, 1H); 5.76-5.79 (m, 1.5H); 5.91 (d, J=6.0 Hz, 0.5H); 5.98 (d, J=6.0 Hz, 1H); 6.00 (d, J=5.0 Hz, 1H); 7.22-7.29 (m, 2H); 7.41-7.45 (m, 2H); 7.80-7.84 (m, 2H); 7.88-7.91 (m, 2H).

$^{13}$C-NMR (CDCl$_3$): δ 17.02; 21.69; 21.77; 35.00; 35.60; 35.96; 36.11; 36.80; 36.95; 39.92; 40.67; 44.07; 54.19; 54.57; 55.69; 56.01; 56.16; 56.24; 59.88; 59.93; 65.82; 65.86; 80.09; 80.28; 80.89; 124.69; 124.75; 128.07; 128.1; 128.17; 129.78; 129.81; 129.86; 129.94; 129.97; 130.59; 130.71; 130.77; 133.57; 133.60; 134.52; 134.57; 150.44; 150.74; 151.72; 152.22; 159.17; 159.24; 163.76; 164.15; 164.23; 170.24; 170.41; 172.48; 172.56.

Example 8. Pharmacokinetic Data of Meropenem after Dosing of I-A-1 in Guinea Pigs Guinea pigs were chosen to evaluate the concentrations of meropenem in the lung. The intra-tracheal (IT) route was selected in order to maximize exposure to the conducting airways, which is the intended target for humans. Dose selection was calculated using Aztreonam, a closely related β-lactam antibiotic and the only approved inhaled antibiotic, as a comparator. An Aztreonam human dose of 75 mg thrice daily (225 mg/day), or 3.75 mg/kg each day (assuming a 60-kg human), equates to a weight-adjusted dose of 1.6 mg meropenem for a 425-gram guinea pig. The dose of Compound I-A-1 (meropenem prodrug), 2.9 mg per animal, was reached using a 0.55× factor to account for the difference in molecular weight. Animals were given a single dose of either 8.0 mg/mL solution of meropenem (free parent) or 14.5 mg/mL suspension of Compound I-A-1 formulated as an MPP in accordance with Example 3 (equivalent to 8.0 mg/mL of meropenem) using an IT microsprayer. The dose volume was 0.2 mL per animal. At the designated time points (0.083, 0.25, 0.5, 1, 3, 6, 9, and 12 h), lungs were removed, snapped frozen and homogenized for bio-analytical analysis of meropenem and pro-drug. Three (3) animals were tested per group per time point. The drug concentrations were determined by tandem mass spectrometry.

Figure 7:
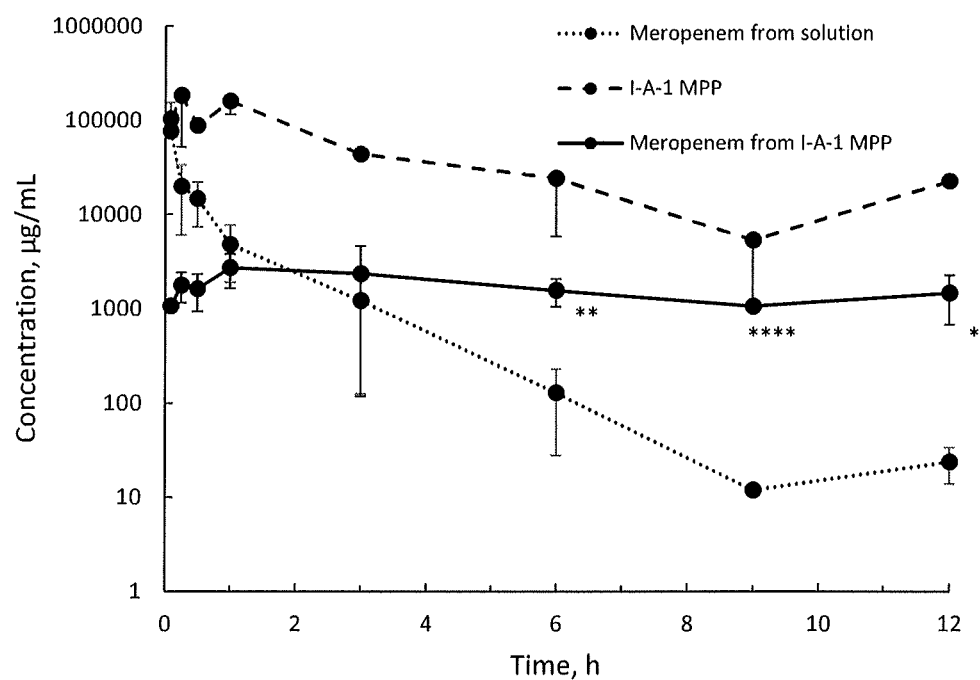
FIG. 7 is a plot showing the pharmacokinetics of meropenem in the lung of guinea pigs after intra-tracheal (IT) dosing from a solution of meropenem or Compound I-A-1 (a meropenem prodrug) formulated as a mucus-penetrating particle (MPP) prepared according to Example 3. Error bars show the standard errors of the mean (n=3 animals per time point).

FIG. 7 shows the pharmacokinetic profiles after IT dosing of Compound I-A-1 MPP of the present invention and meropenem, and levels of meropenem after dosing with Compound I-A-1, a meropenem prodrug, MPP.

The results of this study in guinea pigs demonstrate lung meropenem levels resulting from administration of Compound I-A-1 MPP, formulated as a plurality of particles coated with a surface altering agent as describe in Example 3, were sustained over time, and had enhanced duration in guinea pig lung compared with meropenem from a solution of free meropenem.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

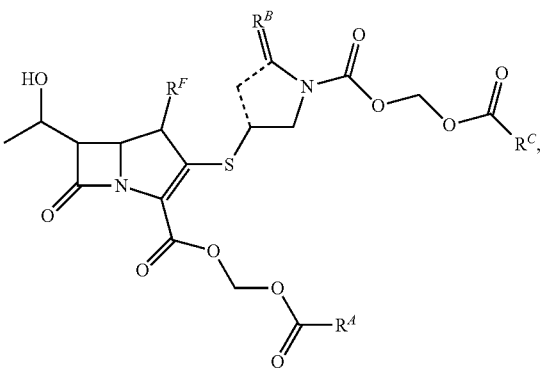

or a pharmaceutically acceptable salt, solvate, hydrate, polymorph, co-crystal, tautomer, stereoisomer, or isotopically labeled derivative thereof;
wherein:
------ is a single bond or null;
≈≈≈ is a single or double bond;
$R^A$ is substituted or unsubstituted aryl, or substituted or unsubstituted heteroaryl;
$R^B$ is —C(=O)—N(Me)$_2$, —CH$_2$—NH—S(=O)$_2$—NH$_2$,

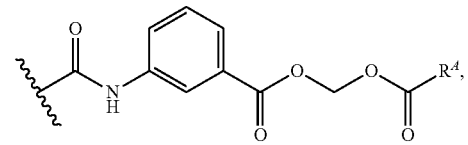

=NH, or

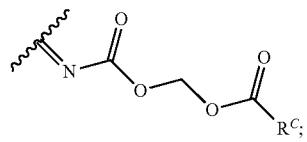

$R^C$ is substituted or unsubstituted aryl, or substituted or unsubstituted heteroaryl;
$R^F$ is hydrogen or methyl; and
provided that when $R^A$ is an unsubstituted C$_4$ aliphatic, then $R^C$ is an unsubstituted C$_6$-C$_{12}$ aliphatic, a substituted aliphatic, substituted or unsubstituted carbocyclyl, substituted or unsubstituted aryl, or substituted or unsubstituted heteroaryl.

2. The compound of claim 1, wherein $R^A$ is substituted or unsubstituted, 6- to 14-membered aryl.

3. The compound of claim 1, wherein $R^A$ is substituted phenyl.

4. The compound of claim 1, wherein $R^A$ is unsubstituted phenyl.

5. The compound of claim 1, wherein $R^C$ is substituted or unsubstituted, 6- to 14-membered aryl.

6. The compound of claim 1, wherein $R^C$ is substituted phenyl.

7. The compound of claim 1, wherein $R^C$ is unsubstituted phenyl.

8. The compound of claim 1, wherein the compound is of Formula (I-A):

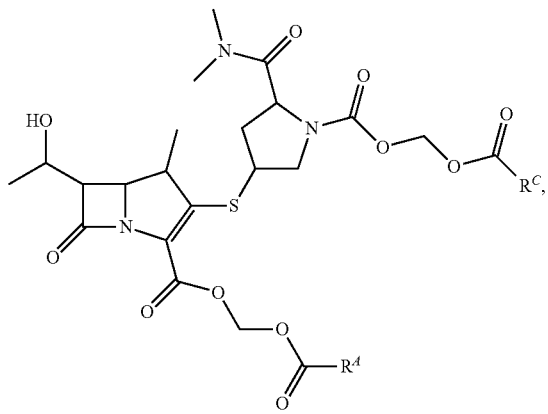

(I-A)

or a pharmaceutically acceptable salt, solvate, hydrate, polymorph, co-crystal, tautomer, stereoisomer, or isotopically labeled derivative thereof.

9. A compound of Formula (I-A-1):

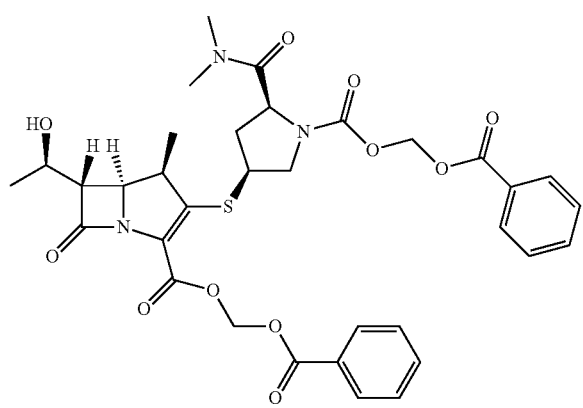

(I-A-1)

or a pharmaceutically acceptable salt, solvate, hydrate, polymorph, co-crystal, tautomer, stereoisomer, or isotopically labeled derivative thereof.

10. The compound of claim 1, wherein the compound is of Formula (I-B):

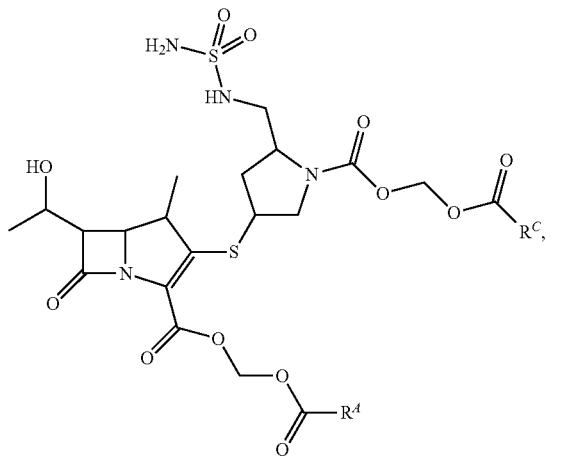

(I-B)

or a pharmaceutically acceptable salt, solvate, hydrate, polymorph, co-crystal, tautomer, stereoisomer, or isotopically labeled derivative thereof.

11. The compound of claim 1, wherein the compound is of Formula (I-C):

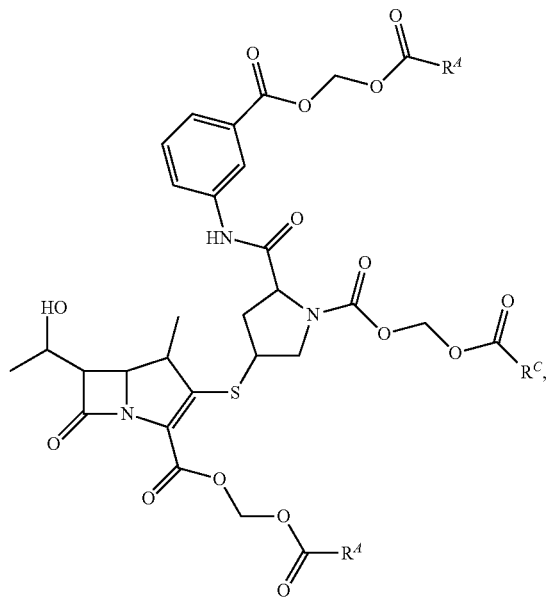

(I-C)

or a pharmaceutically acceptable salt, solvate, hydrate, polymorph, co-crystal, tautomer, stereoisomer, or isotopically labeled derivative thereof.

12. The compound of claim 1, wherein the compound is of Formula (I-D):

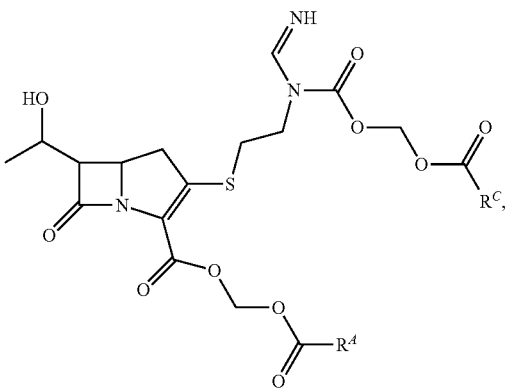

(I-D)

or a pharmaceutically acceptable salt, solvate, hydrate, polymorph, co-crystal, tautomer, stereoisomer, or isotopically labeled derivative thereof.

13. A pharmaceutical composition comprising a compound of claim 1, or a pharmaceutically acceptable salt, solvate, hydrate, polymorph, co-crystal, tautomer, stereoisomer, or isotopically labeled derivative thereof, and optionally a pharmaceutically acceptable excipient.

14. A pharmaceutical composition comprising:
a plurality of particles comprising:
a core comprising a compound of claim 1, or a pharmaceutically acceptable salt, solvate, hydrate, polymorph, co-crystal, tautomer, stereoisomer, or isotopically labeled derivative thereof, and
a coating of a surface altering agent surrounding the core,
wherein the surface altering agent is a triblock copolymer of the structure:
(hydrophilic block)-(hydrophobic block)-(hydrophilic block),
wherein the surface altering agent is present on the outer surface of the core at a density of at least 0.01 surface altering agent per $nm^2$; and
optionally a pharmaceutically acceptable excipient.

15. A pharmaceutical composition comprising:
a plurality of particles comprising:
a core comprising a compound of claim 1, or a pharmaceutically acceptable salt, solvate, hydrate, polymorph, co-crystal, tautomer, stereoisomer, or isotopically labeled derivative thereof, and
a coating of a surface altering agent surrounding the core,
wherein the surface altering agent is a synthetic polymer having pendant hydroxyl groups on the backbone of the polymer, the polymer having a molecular weight of at least about 1 kDa and less than or equal to about 1000 kDa, and wherein the polymer is at least about 30% hydrolyzed and less than about 95% hydrolyzed,
wherein the surface altering agent is present on the outer surface of the core at a density of at least 0.01 surface altering agent per $nm^2$; and
optionally a pharmaceutically acceptable excipient.

16. The pharmaceutical composition of claim 14, wherein the average size of the core ranges from about 50 nm to about 1 μm.

17. The pharmaceutical composition of claim 14, wherein the average size of the coated particle ranges from about 50 nm to about 1 μm.

18. The pharmaceutical composition of claim 14, wherein the average smallest cross-sectional dimension of the plurality of coated particles ranges from about 50 nm to about 1 μm.

19. The pharmaceutical composition of claim 14, wherein the polydispersity index of the cores and/or coated particles is less than about 0.2, less than about 0.15, less than about 0.1, or less than about 0.05.

20. The pharmaceutical composition of claim 14, wherein the compound, or the pharmaceutically acceptable salt thereof, constitutes at least about 50 wt %, at least about 60 wt %, at least about 70 wt %, at least about 80 wt %, at least about 90 wt %, at least about 95 wt %, or at least about 99 wt % of the core.

21. The pharmaceutical composition of claim 14, wherein the aqueous solubility of the compound, or the pharmaceutically acceptable salt thereof, is less than 1 mg/mL, less than 0.1 mg/mL, or less than 0.01 mg/mL at 25° C.

22. The pharmaceutical composition of claim 14, wherein the surface altering agent is present in the pharmaceutical composition in an amount of between about 0.05 wt % and about 5 wt % of the pharmaceutical composition.

23. The pharmaceutical composition of claim 14, wherein the surface altering agent is covalently attached to the core.

24. The pharmaceutical composition of claim 14, wherein the surface altering agent is non-covalently adsorbed to the core.

25. The pharmaceutical composition of claim 14, wherein the surface altering agent is present on the outer surface of the core at a density of at least about 0.01, at least about 0.03, at least about 0.1, at least about 0.3, at least about 1, at least about 3, at least about 10, or at least about 30 surface altering agents per $nm^2$.

26. The pharmaceutical composition of claim 15, wherein the polymer comprises pendant hydroxyl groups on the backbone of the triblock copolymer.

27. The pharmaceutical composition of claim 14, wherein at least one hydrophilic block of the triblock copolymer comprises poly(ethylene glycol).

28. The pharmaceutical composition of claim 14, wherein the hydrophobic block of the triblock copolymer is poly(propylene oxide).

29. The pharmaceutical composition of claim 14, wherein the triblock copolymer is poly(ethylene glycol)-poly(propylene oxide)-poly(ethylene glycol).

30. The pharmaceutical composition of claim 15, wherein the polymer is at least about 40% hydrolyzed, at least about 50% hydrolyzed, at least about 60% hydrolyzed, at least about 70% hydrolyzed, at least about 80% hydrolyzed, or at least about 90% hydrolyzed.

31. The pharmaceutical composition of claim 15, wherein the polymer is less than about 95%, less than about 90%, or less than about 80% hydrolyzed.

32. The pharmaceutical composition of claim 14, wherein the two hydrophilic blocks of the triblock copolymer constitute at least about 20 wt %, at least about 30 wt %, at least about 40 wt %, at least about 50 wt %, or at least about 60 wt % of the triblock polymer, and/or less than about 80 wt % of the triblock copolymer.

33. The pharmaceutical composition of claim 14, wherein the molecular weight of each block of the triblock copolymer is independently at least about 1.8 kDa, at least about 2 kDa, at least about 2.5 kDa, at least about 3 kDa, at least about 4 kDa, or at least about 5 kDa.

34. The pharmaceutical composition of claim 14, wherein the molecular weight of the hydrophobic block of the triblock copolymer is at least about 2 kDa, at least about 3 kDa, at least about 4 kDa, or at least about 6 kDa, and/or less than about 20 kDa, less than about 10 kDa, or less than about 8 kDa.

35. The pharmaceutical composition of claim 14, wherein the molecular weight of the triblock copolymer is at least about 2 kDa, at least about 5 kDa, at least about 10 kDa, at least about 20 kDa, at least about 50 kDa, at least about 80 kDa, at least about 100 kDa, or at least about 120 kDa.

36. The pharmaceutical composition of claim 14, wherein the molecular weight of the triblock copolymer is less than about 200 kDa, less than about 180 kDa, less than about 150 kDa, less than about 130 kDa, less than about 100 kDa, less than about 80 kDa, less than about 50 kDa, or less than about 30 kDa.

37. The pharmaceutical composition of claim 14, wherein:
the molecular weight of the hydrophobic block is at least about 2 kDa; and
the two hydrophilic blocks constitute at least about 15 wt % of the triblock copolymer.

38. The pharmaceutical composition of claim 14, wherein the triblock copolymer is a poloxamer.

39. The pharmaceutical composition of claim 14, wherein the triblock copolymer is poloxamer 407.

40. The pharmaceutical composition of claim 14, wherein the compound, or the pharmaceutically acceptable salt, solvate, hydrate, polymorph, co-crystal, tautomer, stereoisomer, or isotopically labeled derivative thereof, is encapsulated in a polymer, a lipid, a protein, or a combination thereof.

41. The pharmaceutical composition of claim 14 further comprising a pharmaceutical agent selected from the group consisting of antifungal agents, antiprotozoan agents, antibacterial agents, anti-viral agents, anti-inflammatory agents, anti-proliferative agents, and pain-relieving agents.

42. The pharmaceutical composition of claim 14, wherein the pharmaceutical composition is suitable for inhalational administration to a subject.

43. The pharmaceutical composition of claim 42, wherein pharmaceutical composition is for reversing, alleviating, delaying the onset of, or inhibiting the progress of a respiratory tract disease.

44. The pharmaceutical composition of claim 42, wherein the subject is a human.

45. The pharmaceutical composition of claim 43, wherein the respiratory tract disease is a respiratory tract infection.

46. The pharmaceutical composition of claim 45, wherein the respiratory tract infection is bronchitis or pneumonia.

47. The pharmaceutical composition of claim 45, wherein the respiratory tract infection is caused by a *Pseudomonas* species.

48. The pharmaceutical composition of claim 45, wherein the respiratory tract infection is caused by *Pseudomonas aeruginosa*.

49. The pharmaceutical composition of claim 43, wherein the respiratory tract disease is cystic fibrosis.

50. The pharmaceutical composition of claim 43, wherein the coating on the core is present in a sufficient amount to increase the exposure of the compound, or the pharmaceutically acceptable salt thereof, by at least 10% when administered in the pharmaceutical composition compared to the exposure of the compound, or the pharmaceutically acceptable salt, solvate, hydrate, polymorph, co-crystal, tautomer, stereoisomer, or isotopically labeled derivative thereof, when administered as a core without the coating.

51. The pharmaceutical composition of claim 43, wherein the coating on the core is present in a sufficient amount to increase the concentration of the compound by at least 10% in the subject when administered in the pharmaceutical composition, compared to the concentration of the compound in the subject when administered as a core without the coating.

52. A kit comprising:
    a compound of claim 1, or a pharmaceutically acceptable salt, solvate, hydrate, polymorph, co-crystal, tautomer, stereoisomer, or isotopically labeled derivative thereof, or a pharmaceutical composition thereof; and
    instructions for administering the compound, the pharmaceutically acceptable salt, solvate, hydrate, polymorph, co-crystal, tautomer, stereoisomer, or isotopically labeled derivative thereof, or the pharmaceutical composition.

53. A method of treating a respiratory tract disease in a subject having such a disease comprising:
    inhalationally administering to the subject a therapeutically effective amount of a compound of claim 1, or a pharmaceutically acceptable salt, solvate, hydrate, polymorph, co-crystal, tautomer, stereoisomer, or isotopically labeled derivative thereof, or a pharmaceutical composition thereof.

54. The method of claim 53, wherein the step of administering comprises administering one or more doses comprising independently at least about 0.003 mg, at least about 0.01 mg, at least about 0.03 mg, at least about 0.1 mg, at least about 0.3 mg, at least about 1 mg, at least about 3 mg, at least about 10 mg, or at least about 30 mg of the compound, or the pharmaceutical acceptable salt, solvate, hydrate, polymorph, co-crystal, tautomer, stereoisomer, or isotopically labeled derivative thereof, per kg of body weight of the subject.

55. The method of claim 53, wherein the step of administering comprises administering two or more doses, wherein the time period between consecutive doses is at least about 6 hours, at least about 8 hours, at least about 12 hours, at least about 36 hours, or at least about 48 hours.

56. The method of claim 53, further comprising sustaining an efficacious level of the compound, or an active metabolite thereof, in the subject for at least 12 hours after administration.

57. The method of claim 53, wherein the subject is a human.

58. The method of claim 53, wherein the respiratory tract disease is a respiratory tract infection.

59. The method of claim 58, wherein the respiratory tract infection is bronchitis or pneumonia.

60. The method of claim 58, wherein the respiratory tract infection is caused by a *Pseudomonas* species.

61. The method of claim 58, wherein the respiratory tract infection is caused by *Pseudomonas aeruginosa*.

62. The method of claim 53, wherein the respiratory tract disease is cystic fibrosis.

63. The method of claim 53, wherein the coating on the core is present in a sufficient amount to increase the exposure of the compound, or the pharmaceutically acceptable salt thereof, by at least 10% when administered in the pharmaceutical composition compared to the exposure of the compound, or the pharmaceutically acceptable salt, solvate, hydrate, polymorph, co-crystal, tautomer, stereoisomer, or isotopically labeled derivative thereof, when administered as a core without the coating.

64. The method of claim 53, wherein the coating on the core is present in a sufficient amount to increase the concentration of the compound by at least 10% in the subject when administered in the pharmaceutical composition, compared to the concentration of the compound in the subject when administered as a core without the coating.

65. A method of preparing a compound of Formula (I), or a pharmaceutically acceptable salt thereof, comprising:
    reacting a compound of Formula (i-A), or a salt thereof, with a compound of Formula (i-B) to provide a compound of Formula (i-C), or a salt thereof:

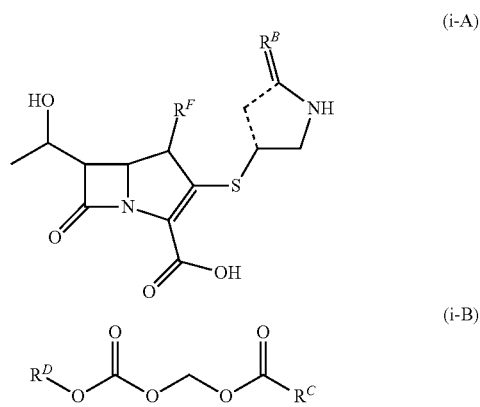

-continued (i-C)

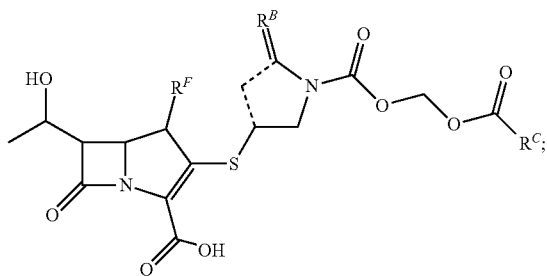

reacting the compound of Formula (i-C), or the salt thereof, with a base and a compound of Formula (i-D) to provide the compound of Formula (I), or the pharmaceutically acceptable salt, solvate, hydrate, polymorph, co-crystal, tautomer, stereoisomer, or isotopically labeled derivative thereof:

(i-D)

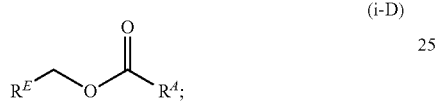

wherein:
$R^D$ is an electron-withdrawing group; and
$R^E$ is a leaving group.

66. The method of claim 65, wherein:
$R^D$ is

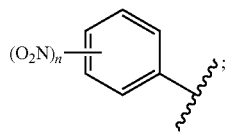

and n is 1 or 2.

67. The method of claim 65, wherein:
$R^E$ is Cl, Br, I, or —OS(=O)$_w R^{E1}$;
w is 1 or 2; and
$R^{E1}$ is substituted or unsubstituted aliphatic, substituted or unsubstituted carbocyclyl, substituted or unsubstituted heterocyclyl, substituted or unsubstituted aryl, or substituted or unsubstituted heteroaryl.

* * * * *

UNITED STATES PATENT AND TRADEMARK OFFICE
CERTIFICATE OF CORRECTION

PATENT NO. : 9,725,451 B2 Page 1 of 7
APPLICATION NO. : 14/777018
DATED : August 8, 2017
INVENTOR(S) : Winston Zapanta Ong et al.

It is certified that error appears in the above-identified patent and that said Letters Patent is hereby corrected as shown below:

On the Title Page

Item (57) under abstract, replace " 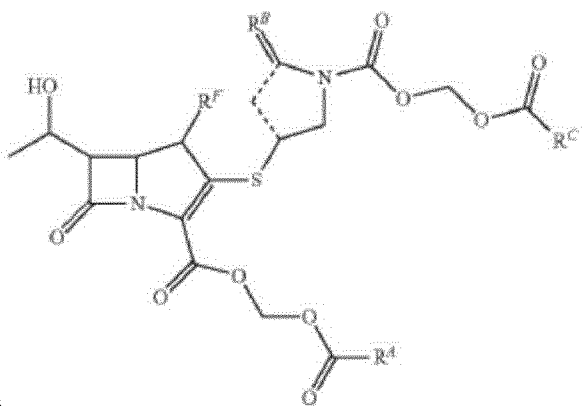 " with 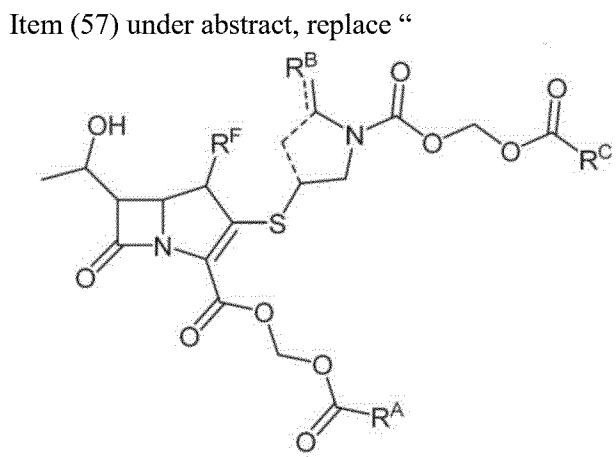 --.

Signed and Sealed this
Second Day of June, 2020

Andrei Iancu
*Director of the United States Patent and Trademark Office*

CERTIFICATE OF CORRECTION (continued)
U.S. Pat. No. 9,725,451 B2

In the Specification (Column 3, Lines 35–45), please replace " 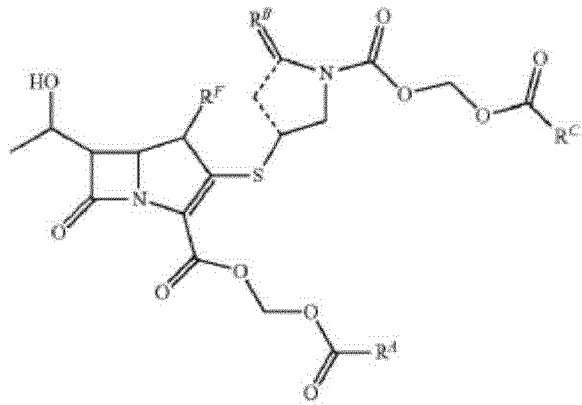 " with 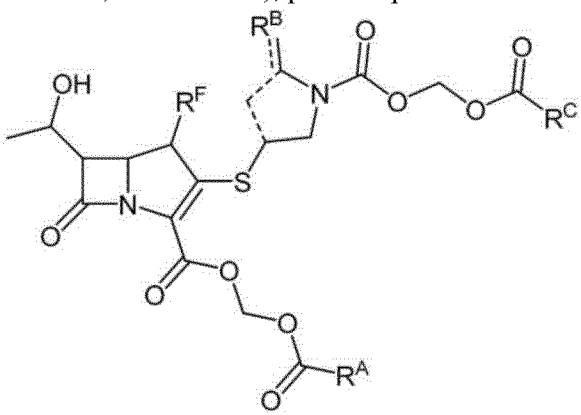 --.

(Column 4, Lines 40–50), please replace " 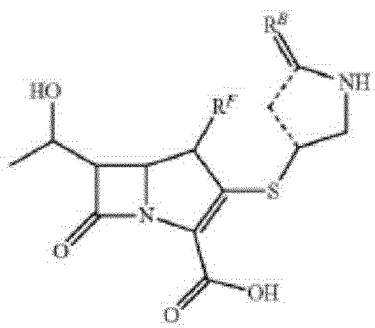 " with 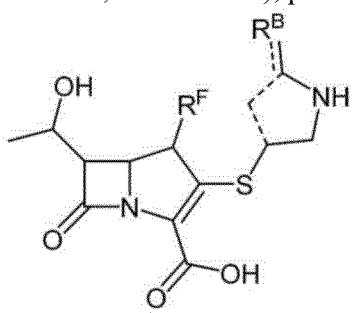 --.

(Column 4, Lines 55–65), please replace " 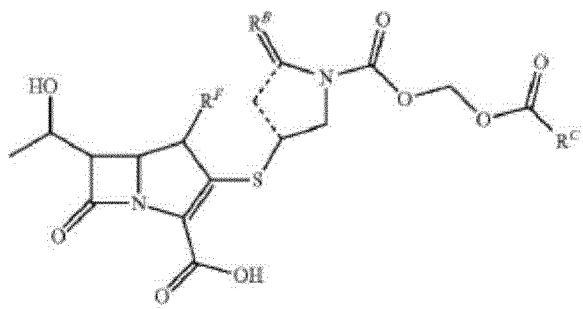 " with
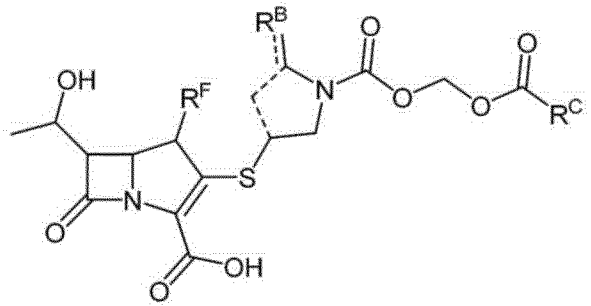
--.
(Column 32, Lines 20–35), please replace " 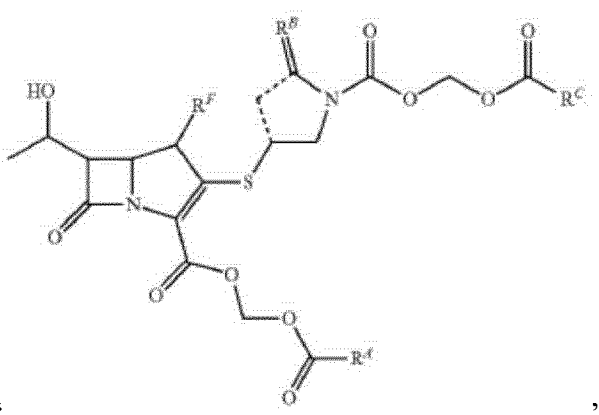 " with
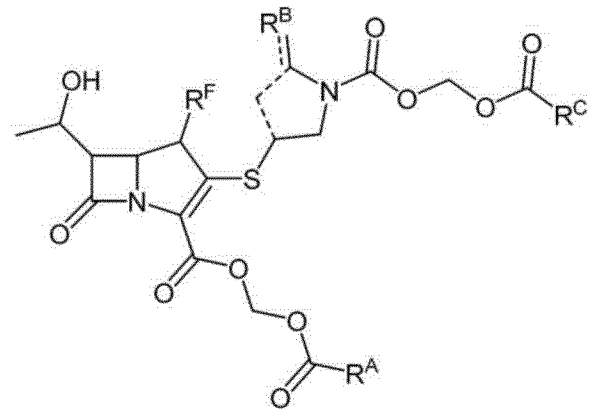
--.

CERTIFICATE OF CORRECTION (continued)
U.S. Pat. No. 9,725,451 B2

(Column 33, Lines 10–20), please replace " 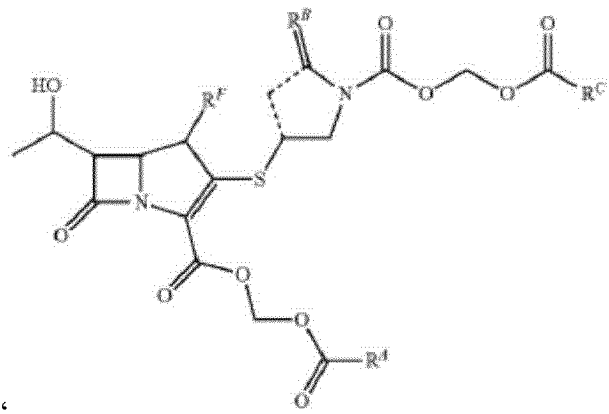 " with

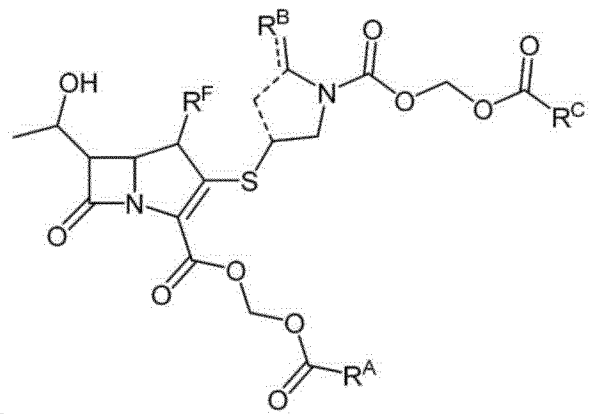

-- --.

(Column 42, Lines 25–35), please replace " 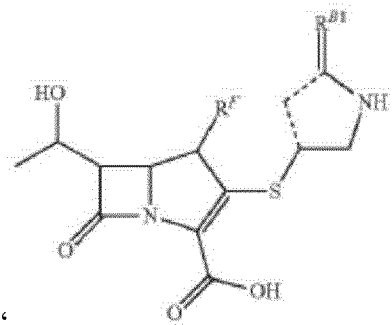 " with

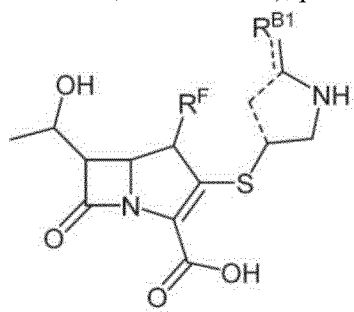

-- --.

CERTIFICATE OF CORRECTION (continued)
U.S. Pat. No. 9,725,451 B2

(Column 43, Lines 35–45), please replace " 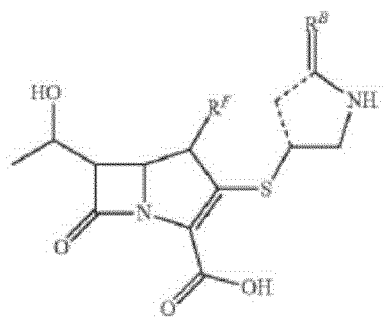 " with

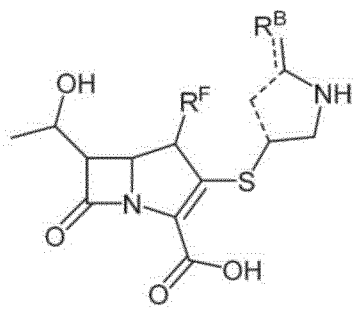

-- --.

(Column 43, Lines 50–60), please replace " 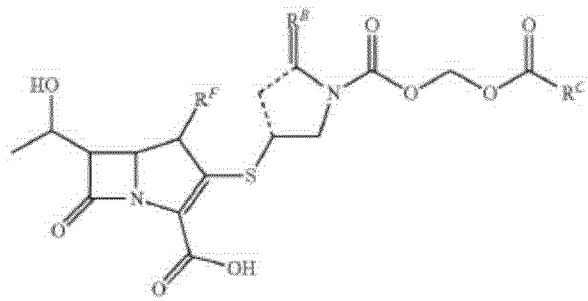 " with

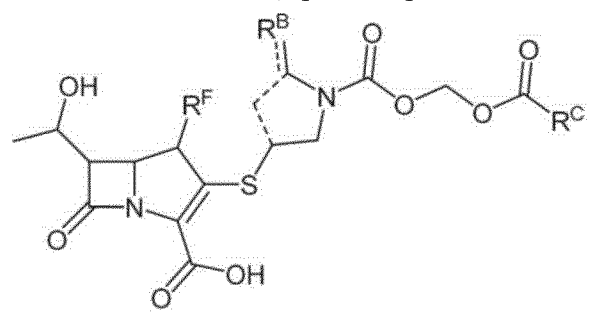

-- --.

CERTIFICATE OF CORRECTION (continued)
U.S. Pat. No. 9,725,451 B2

In the Claims

In Claim 1 (Column 114, Lines 5–15), please replace

" 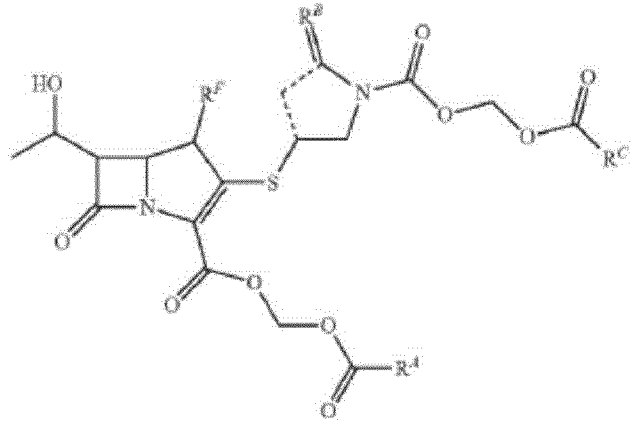 " with

-- 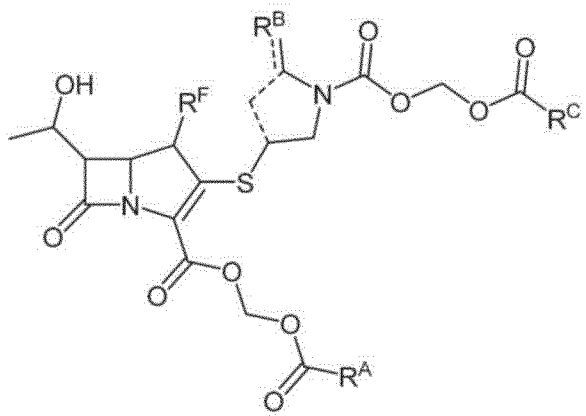 --.

In Claim 65 (Column 120, Lines 50–60), please replace " 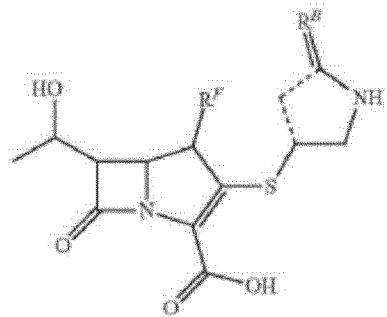 " with

CERTIFICATE OF CORRECTION (continued)
U.S. Pat. No. 9,725,451 B2

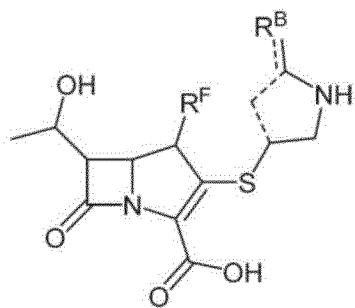

-- --.

In Claim 65 (Column 121, Lines 5–15), please replace

" 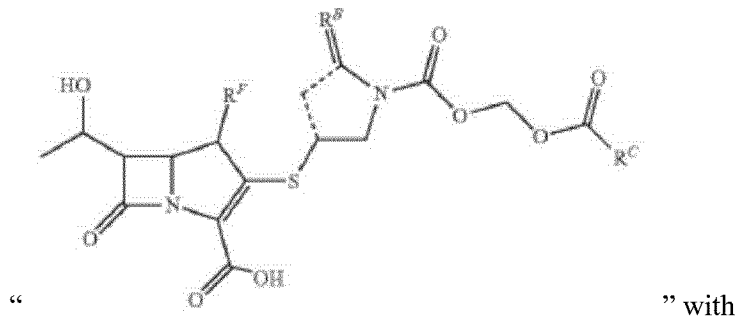 " with

-- 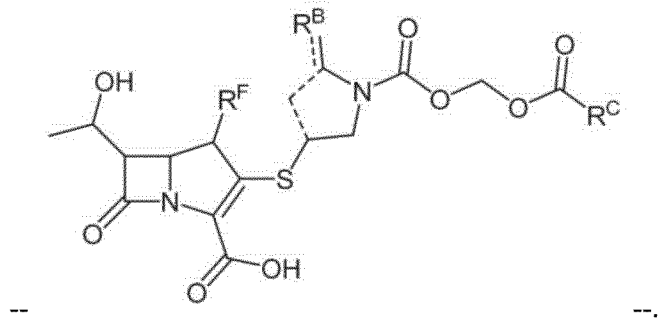 --.